United States Patent [19]

Remold-O'Donnell

[11] Patent Number: 5,827,672
[45] Date of Patent: Oct. 27, 1998

[54] HUMAN MONOCYTE ELASTASE INHIBITOR ANTIBODIES

[75] Inventor: Eileen Remold-O'Donnell, Brookline, Mass.

[73] Assignee: Center for Blood Research, Inc., Boston, Mass.

[21] Appl. No.: 662,318

[22] Filed: Jun. 13, 1996

Related U.S. Application Data

[63] Continuation of Ser. No. 315,831, Sep. 30, 1994, Pat. No. 5,663,299, which is a continuation-in-part of Ser. No. 755, 461, Sep. 6, 1991, Pat. No. 5,370,991, which is a continuation-in-part of Ser. No. 314,383, Feb. 23, 1989, abandoned.

[51] Int. Cl.$^6$ .......................... C07K 16/00; C12P 21/08; G01N 33/53; G01N 33/537
[52] U.S. Cl. ...................... 435/7.92; 435/7.1; 530/387.9; 530/338.15; 530/388.26
[58] Field of Search .......................... 530/387.9, 388.15, 530/388.26; 435/7.1, 7.92

[56] References Cited

U.S. PATENT DOCUMENTS 5,364,619  11/1994  Packard et al. .......................... 424/85.1

FOREIGN PATENT DOCUMENTS

| | | |
|---|---|---|
| A-896-543 | 8/1983 | Belgium . |
| A-103-409 | 3/1984 | European Pat. Off. . |
| A-304971 | 3/1989 | European Pat. Off. . |
| 9009737 | 9/1990 | WIPO . |
| WO 96/10418 | 4/1996 | WIPO . |

OTHER PUBLICATIONS

Baggiolini et al. Agents and Actions, 1978, 8:3–10.
Vaitukaitis, J. Methods in Enzymology, 1981, 73:46–52.
Giri, I., et al.., Proc. Natl. Acad. Sci. USA, 1985, 82:1580–1584.
Sofer, G. and V. Britton, Biotechniques, Nov/Dec 1983, 198–203.
Janoff, A., et al., Proc. Soc. Biol. Med., 1971, 136:1050–1053.
Blondin, J., et al., Am. Rev. Resp. Dis., 1972. 106:477–479.
Dubin, A., Eur, J. Biochem., 1977, 73:429–435.
Remold–O'Donnell, E., et al., J. Biol. Chem., 1983, 258:3251–3257.
Kopitar, M., et al., Acta Pharm., Jugosl., 1985, 35:203–212.
Valentine, R., et al., Proc. Soc. Exp. Biol. Med., 1981, 168:238–244.
Potempa, J., et al., J. Biol. Chem., 1988, 263:7364–7369.
Hintz, P., et al., Biol. Chem. Hoppe–Seyler, 1987, 368:1333–1342 and "Biol. Abstracts", vol. 85, No. 3, 1988, Ref. No. 27273.
Remold–O'Donnell et al. J. Exp. Med., 1989, 169:1071–1986.
Welgus, H., et al., J. Clin. Invest., 1986, 77:1675–1681.
Senoir, R., et al., J. Clin. Invest., 1982, 69:384–393.
Sinha, S., Proc. Natl. Acad. Sci. USA, 1987, 84:2228–2232.
Takahashi, H., et al., J. Biol. Chem., 1988, 263(5):2543–2547.
Suggs, S., et al., Proc. Natl. Acad. Sci. USA, 1981, 78(11);6613–6617.
Garvey et al., Methods in immunology, 3rd Edition, March 1977, pp. 194–231.
Junger, W., Biol. Chemistry Hoppe–Seyler, 369:63–68, supplement (1988).
Thomas, R., et al. FASEB Journal, 4:A2156, Abstract No. 2682 (1990).
Takeuchi, K., et al. J. Biol. Chem., 264:7431–7436 (1989).
Thomas, R., et al., J. Leukocyte Biology, 50:568–579 (1991).
DBA Abstract, Accession No. 88–04290, European Patent No. EP 255011, Feb. 3, 1988.
Biosis Abstract, Accession No. 83054104, Von Wilcken–Bergmann et al, EMBO 55(12):3219–3226 (1986).
Jallat, S. et al., "Altered specificities of genetically engineering alpha 1–antitrypsin variants" Prot. Engr. 1 (1):29–35 (1986).
Patston, P.A. et al., "Reactivity of alpha1–antitrypsin mutants against proteolytic enzymes of the kallikrein–kinin, complement, and fibrinolytic sustems" J. Biol. Chem. 265(18):10786–10791 (1989).
Bishoff, R. et al., "Purification and biochemical characterization of recombinant alpha1–antitrypsin variants expressed in *Escherichia coli*" Biochem. 30:3464–2472 (1991).
Schulze, A.J. et al., "Inhibitory activity and conformational translation of alpha 1–proteinase inhibitor variants" Eur. J. Biochem. 202:1147–1156 (1991).
Stephens, A.W. et al., "Site–directed mutagenesis of the reactive center (Series 394) of antithrombin III" J. Biol. Chem. 263(31):15849–15852 (1988).
George, P.M. et al., "Charaterization of antithrombins produced by active site mutagenesis of human alpha–1–antitrypsin expressed in yeast" Blood 73(2):490–496 (1989).
Brennan, S.O. et al., "Alpha–1–antitrypsin Christchrich, 369 Glu to Lys: mutation at the P5$^1$ position does not affect inhibitory activity" Biochim. Biophys. Acta 873:13–19 (1986).
Remold–O'Donnell, E. "The ovalbumin family of serpin proteins" FEBS Lett. 315(2):105–108 (1993).
Stein, P.E. et al., "Crystal structure of ovalbumin as in model for the reactive centre of serpins", Nature 347:99–102 (1990).

(List continued on next page.)

*Primary Examiner*—Frank C. Eisenschenk
*Assistant Examiner*—Patrick Nolan
*Attorney, Agent, or Firm*—Wolf, Greenfield & Sacks, PC

[57] ABSTRACT

A new human elastase inhibitor is provided. The human monocyte elastase inhibitor is isolated, purified, characterized at the molecular level and cloned. The human monocyte elastase inhibitor is capable of forming a covalent complex with elastase or Proteinase-3 and is capable of inhibiting elastase.

10 Claims, 15 Drawing Sheets

OTHER PUBLICATIONS

Stein, P.E. et al., "Crystal structure of uncleaved ovalbumin at 1.95 Åresolution" J. Mol. Biol. 221: 941–959 (1991).

Takahashi, N. et al., "Role of an intrachain disulfide bond in the conformation and stability of ovalbumin" J. Biochem, 109:846–851 (1991).

Remold–O'Donnell, E., "Sequence and molecular characterization of human monocyte/neutrophil elastase inhibitor" PNAS, USA 89:5635–5639 (1992).

Remold–O'Donnell (1985) A Fast–acTing elastase inhibitor in human monocytes J. Exp. Med. 162(6): 2142–2155.

Johnstone et al. (1988) Immunohistochemistry in practice. Blackwell Scientific Publications, Oxford second editor.

AMINO ACID COMPOSITIONS

| | No. Residues/100 Amino Acids | | | No. of Residues/Molecule | |
|---|---|---|---|---|---|
| Residue | Avg. of 200 proteins | EI | a1-AT | EI | a1-AT |
| Asx | 10.7 | 11.1 | 10.9 | 40 | 43 |
| Glx | 10.6 | 12.3 | 12.4 | 44 | 50 |
| His | 2.2 | 1.9 | 3.5 | 7 | 13 |
| Lys | 6.5 | 7.1 | 8.6 | 26 | 34 |
| Arg | 4.4 | 3.8 | 1.8 | 14 | 7 |
| Ser | 6.3 | 8.1 | 5.3 | 29 | 21 |
| Thr | 5.7 | 5.7 | 7.6 | 21 | 30 |
| Pro | 4.8 | 5.4 | 4.3 | 20 | 17 |
| Ala | 8.5 | 8.1 | 6.1 | 29 | 24 |
| Cys | 2.3 | 1.5 | 0.2 | 5 | 1 |
| Gly | 8.1 | 7.0 | 5.6 | 25 | 22 |
| Tyr | 3.3 | 2.1 | 1.5 | 8 | 6 |
| Val | 6.8 | 5.2 | 6.1 | 19 | 24 |
| Ile | 5.0 | 3.0 | 4.8 | 11 | 19 |
| Leu | 8.1 | 9.2 | 11.4 | 33 | 45 |
| Phe | 3.7 | 4.9 | 6.8 | 18 | 27 |
| Met | 1.9 | 2.0 | 2.3 | 7 | 9 |
| Trp | 1.3 | ND | 0.5 | ND | 2 |
| Total | | | | .360 | 394 |

FIG. 4

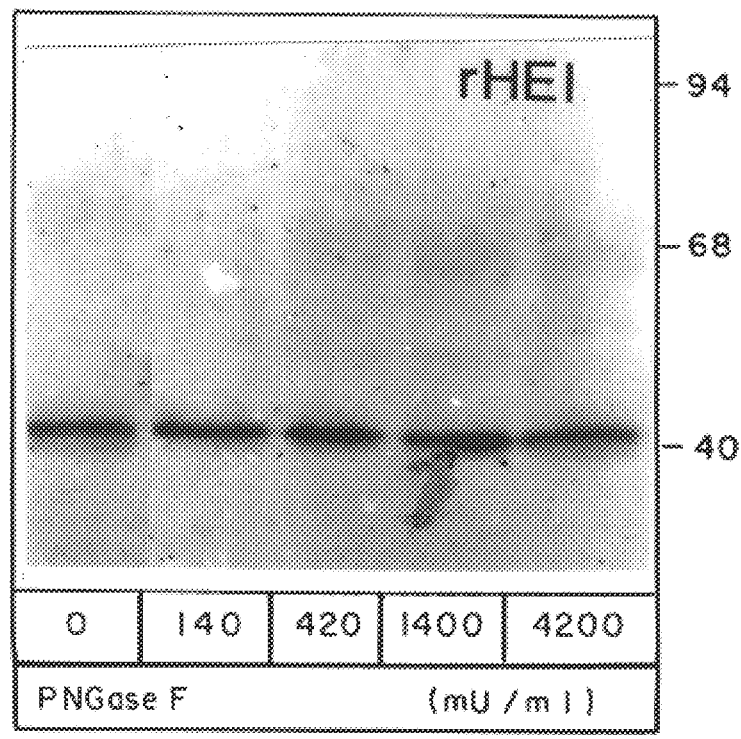
FIG. IIA
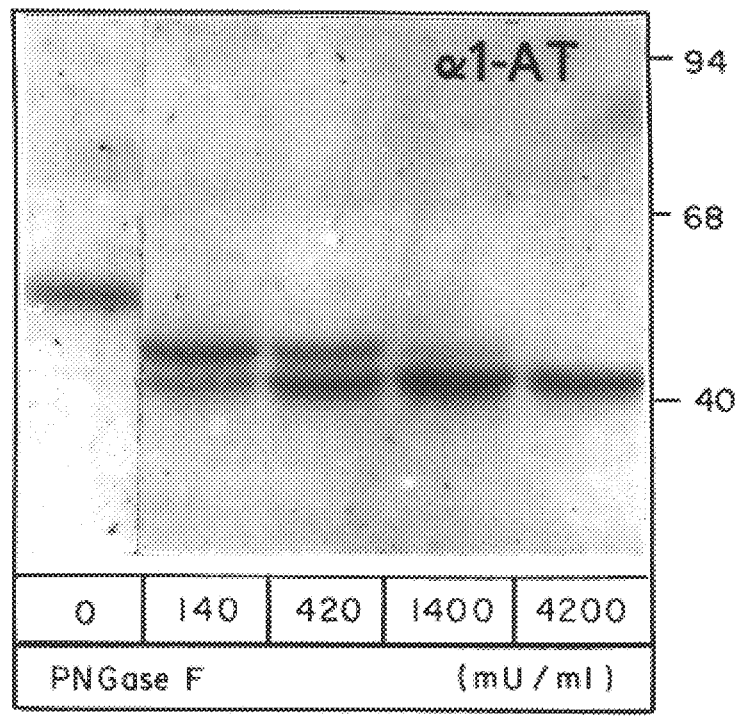
FIG. IIB

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: Homo sapiens
        ( G ) CELL TYPE: histiocytic lymphoma
        ( H ) CELL LINE: U937-EI (ATCC#CRL10026)

( x i ) SEQUENCE DESCRIPTION: SEQ ID NO:1:

```
Glu  Ala  Thr  Thr  Asn  Ala  Pro  Phe  Arg
1                  5
```

( 2 ) INFORMATION FOR SEQ ID NO:2:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Homo sapiens
        ( G ) CELL TYPE: histiocytic lymphoma
        ( H ) CELL LINE: U937-EI (ATCC#CRL10026)

( x i ) SEQUENCE DESCRIPTION: SEQ ID NO:2:

```
Lys  Thr  Ile  Asn  Gln  Xaa  Val  Lys
1                  5
```

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO (v i) ORIGINAL SOURCE:
  (A) ORGANISM: Homo sapiens
  (G) CELL TYPE: histiocytic lymphoma
  (H) CELL LINE: U937-EI (ATCC#CRL10026)

(x i) SEQUENCE DESCRIPTION: SEQ ID NO:3:

Phe His Pro Asn Thr Val Glu Glu Val His
1               5                   10

(2) INFORMATION FOR SEQ ID NO:4:

(i) SEQUENCE CHARACTERISTICS:
    (A) LENGTH: 17 amino acids
    (B) TYPE: amino acid
    (C) STRANDEDNESS: single
    (D) TOPOLOGY: linear (i i) MOLECULE TYPE: peptide (i i i) HYPOTHETICAL: NO (i v) ANTI-SENSE: NO (v i) ORIGINAL SOURCE:
    (A) ORGANISM: Homo sapiens
    (G) CELL TYPE: histiocytic lymphoma
    (H) CELL LINE: U937-EI (ATCC#CRL10026)

(x i) SEQUENCE DESCRIPTION: SEQ ID NO:4:

Tyr Gly Ala Asp Leu Ala Ser Val Asp Phe Gln His Ala Ser Glu Asp
1               5                   10                  15

Ala (2) INFORMATION FOR SEQ ID NO:5:

(i) SEQUENCE CHARACTERISTICS:
    (A) LENGTH: 9 amino acids
    (B) TYPE: amino acid
    (C) STRANDEDNESS: single
    (D) TOPOLOGY: linear (i i) MOLECULE TYPE: peptide (i i i) HYPOTHETICAL: NO (i v) ANTI-SENSE: NO (v i) ORIGINAL SOURCE:
    (A) ORGANISM: Homo sapiens
    (G) CELL TYPE: histiocytic lymphoma
    (H) CELL LINE: U937-EI (ATCC#CRL10026)

(x i) SEQUENCE DESCRIPTION: SEQ ID NO:5:

Leu Gly Val Gln Asp Leu Phe Asn Ser
1               5

(2) INFORMATION FOR SEQ ID NO:6:

(i) SEQUENCE CHARACTERISTICS:
    (A) LENGTH: 14 amino acids
    (B) TYPE: amino acid
    (C) STRANDEDNESS: single
    (D) TOPOLOGY: linear (i i) MOLECULE TYPE: peptide (i i i) HYPOTHETICAL: NO (i v) ANTI-SENSE: NO (v i) ORIGINAL SOURCE:
    (A) ORGANISM: Homo sapiens ( G ) CELL TYPE: histiocytic lymphoma
                    ( H ) CELL LINE: U937-EI (ATCC#CRL10026)

( x i ) SEQUENCE DESCRIPTION: SEQ ID NO:6:

Pro  Glu  Asn  Leu  Asp  Phe  Ile  Glu  Val  Asn  Val  Ser  Leu  Pro
1                   5                        10

( 2 ) INFORMATION FOR SEQ ID NO:7:

( i ) SEQUENCE CHARACTERISTICS:
                    ( A ) LENGTH: 13 amino acids
                    ( B ) TYPE: amino acid
                    ( C ) STRANDEDNESS: single
                    ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
                    ( A ) ORGANISM: Homo sapiens
                    ( G ) CELL TYPE: histiocytic lymphoma
                    ( H ) CELL LINE: U937-EI (ATCC#CRL10026)

( x i ) SEQUENCE DESCRIPTION: SEQ ID NO:7:

Tyr  Asn  Phe  Leu  Pro  Glu  Phe  Leu  Val  Ser  Thr  Gln  Lys
1                   5                        10

( 2 ) INFORMATION FOR SEQ ID NO:8:

( i ) SEQUENCE CHARACTERISTICS:
                    ( A ) LENGTH: 22 amino acids
                    ( B ) TYPE: amino acid
                    ( C ) STRANDEDNESS: single
                    ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
                    ( A ) ORGANISM: Homo sapiens
                    ( G ) CELL TYPE: histiocytic lymphoma
                    ( H ) CELL LINE: U937-EI (ATCC#CRL10026)

( x i ) SEQUENCE DESCRIPTION: SEQ ID NO:8:

Val  Leu  Glu  Leu  Pro  Tyr  Gln  Gly  Glu  Glu  Leu  Ser  Met  Val  Ile  Leu
1                   5                        10                       15

Leu  Pro  Asp  Asp  Ile  Glu
                    20

( 2 ) INFORMATION FOR SEQ ID NO:9:

( i ) SEQUENCE CHARACTERISTICS:
                    ( A ) LENGTH: 10 amino acids
                    ( B ) TYPE: amino acid
                    ( C ) STRANDEDNESS: single
                    ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
                    ( A ) ORGANISM: Homo sapiens
                    ( G ) CELL TYPE: histiocytic lymphoma
                    ( H ) CELL LINE: U937-EI (ATCC#CRL10026)

( x i ) SEQUENCE DESCRIPTION: SEQ ID NO:9:

Lys Ile Glu Glu Gln Leu Thr Leu Glu Lys
1               5                   1 0

( 2 ) INFORMATION FOR SEQ ID NO:10:

( i ) SEQUENCE CHARACTERISTICS:
       ( A ) LENGTH: 14 amino acids
       ( B ) TYPE: amino acid
       ( C ) STRANDEDNESS: single
       ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
       ( A ) ORGANISM: Homo sapiens
       ( G ) CELL TYPE: histiocytic lymphoma
       ( H ) CELL LINE: U937-EI (ATCC#10026)

( x i ) SEQUENCE DESCRIPTION: SEQ ID NO:10:

Phe Lys Leu Glu Glu Ser Tyr Thr Leu Asn Ser Asp Leu Ala
1               5                   1 0

( 2 ) INFORMATION FOR SEQ ID NO:11:

( i ) SEQUENCE CHARACTERISTICS:
       ( A ) LENGTH: 10 amino acids
       ( B ) TYPE: amino acid
       ( C ) STRANDEDNESS: single
       ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
       ( A ) ORGANISM: Homo sapiens
       ( G ) CELL TYPE: histiocytic lymphoma
       ( H ) CELL LINE: U937-EI (ATCC#CRL10026)

( x i ) SEQUENCE DESCRIPTION: SEQ ID NO:11:

Phe Ala Tyr Gly Tyr Ile Glu Asp Leu Lys
1               5                   1 0

( 2 ) INFORMATION FOR SEQ ID NO:12:

( i ) SEQUENCE CHARACTERISTICS:
       ( A ) LENGTH: 1316 base pairs
       ( B ) TYPE: nucleic acid
       ( C ) STRANDEDNESS: single
       ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
       ( A ) ORGANISM: Homo sapiens ( i x ) FEATURE:
       ( A ) NAME/KEY: CDS
       ( B ) LOCATION: 49..1188
       ( D ) OTHER INFORMATION: /codon_start= 49

( i x ) FEATURE:

(A) NAME/KEY: mat_peptide
(B) LOCATION: 49..1185

(xi) SEQUENCE DESCRIPTION: SEQ ID NO:12:

```
CCCGCAGCTC GGAGCCCGGA GCGTCCTCGG CGGCTGTCGG TTTTCACC ATG GAG CAG      57
                                                       Met Glu Gln
                                                         1

CTG AGC TCA GCA AAC ACC CGC TTC GCC TTG GAC CTG TTC CTG GCG TTG      105
Leu Ser Ser Ala Asn Thr Arg Phe Ala Leu Asp Leu Phe Leu Ala Leu
      5              10                  15

AGT GAG AAC AAT CCG GCT GGA AAC ATC TTC ATC TCT CCC TTC AGC ATT      153
Ser Glu Asn Asn Pro Ala Gly Asn Ile Phe Ile Ser Pro Phe Ser Ile
 20              25                  30                  35

TCA TCT GCT ATG GCC ATG GTT TTT CTG GGG ACC AGA GGT AAC ACG GCA      201
Ser Ser Ala Met Ala Met Val Phe Leu Gly Thr Arg Gly Asn Thr Ala
             40                  45                  50

GCA CAG CTG TCC AAG ACT TTC CAT TTC AAC ACG GTT GAA GAG GTT CAT      249
Ala Gln Leu Ser Lys Thr Phe His Phe Asn Thr Val Glu Glu Val His
                 55                  60                  65

TCA AGA TTC CAG AGT CTG AAT GCT GAT ATC AAC AAA CGT GGA GCG TCT      297
Ser Arg Phe Gln Ser Leu Asn Ala Asp Ile Asn Lys Arg Gly Ala Ser
             70                  75                  80

TAT ATT CTG AAA CTT GCT AAT AGA TTA TAT GGA GAG AAA ACT TAC AAT      345
Tyr Ile Leu Lys Leu Ala Asn Arg Leu Tyr Gly Glu Lys Thr Tyr Asn
 85                  90                  95

TTC CTT CCT GAG TTC TTG GTT TCG ACT CAG AAA ACA TAT GGT GCT GAC      393
Phe Leu Pro Glu Phe Leu Val Ser Thr Gln Lys Thr Tyr Gly Ala Asp
100              105                 110                 115

CTG GCC AGT GTG GAT TTT CAG CAT GCC TCT GAA GAT GCA AGG AAG ACC      441
Leu Ala Ser Val Asp Phe Gln His Ala Ser Glu Asp Ala Arg Lys Thr
             120                 125                 130

ATA AAC CAG TGG GTC AAA GGA CAG ACA GAA GGA AAA ATT CCG GAA CTG      489
Ile Asn Gln Trp Val Lys Gly Gln Thr Glu Gly Lys Ile Pro Glu Leu
             135                 140                 145

TTG GCT TCG GGC ATG GTT GAT AAC ATG ACC AAA CTT GTG CTA GTA AAT      537
Leu Ala Ser Gly Met Val Asp Asn Met Thr Lys Leu Val Leu Val Asn
         150                 155                 160

GCC ATC TAT TTC AAG GGA AAC TGG AAG GAT AAA TTC ATG AAA GAA GCC      585
Ala Ile Tyr Phe Lys Gly Asn Trp Lys Asp Lys Phe Met Lys Glu Ala
165                 170                 175

ACG ACG AAT GCA CCA TTC AGA TTG AAT AAG AAA GAC AGA AAA ACT GTG      633
Thr Thr Asn Ala Pro Phe Arg Leu Asn Lys Lys Asp Arg Lys Thr Val
180                 185                 190                 195

AAA ATG ATG TAT CAG AAG AAA AAA TTT GCA TAT GGC TAC ATC GAG GAC      681
Lys Met Met Tyr Gln Lys Lys Lys Phe Ala Tyr Gly Tyr Ile Glu Asp
                 200                 205                 210

CTT AAG TGC CGT GTG CTG GAA CTG CCT TAC CAA GGC GAG GAG CTC AGC      729
Leu Lys Cys Arg Val Leu Glu Leu Pro Tyr Gln Gly Glu Glu Leu Ser
             215                 220                 225

ATG GTC ATC CTG CTG CCG GAT GAC ATT GAG GAC GAG TCC ACG GGC CTG      777
Met Val Ile Leu Leu Pro Asp Asp Ile Glu Asp Glu Ser Thr Gly Leu
             230                 235                 240

AAG AAG ATT GAG GAA CAG TTG ACT TTG GAA AAG TTG CAT GAG TGG ACT      825
Lys Lys Ile Glu Glu Gln Leu Thr Leu Glu Lys Leu His Glu Trp Thr
245                 250                 255

AAA CCT GAG AAT CTC GAT TTC ATT GAA GTT AAT GTC AGC TTG CCC AGG      873
Lys Pro Glu Asn Leu Asp Phe Ile Glu Val Asn Val Ser Leu Pro Arg
260                 265                 270                 275

TTC AAA CTG GAA GAG AGT TAC ACT CTC AAC TCC GAC CTC GCC CGC CTA      921
Phe Lys Leu Glu Glu Ser Tyr Thr Leu Asn Ser Asp Leu Ala Arg Leu
                 280                 285                 290
```

| | | | | | | | | | | | | | | | | |
|---|---|---|---|---|---|---|---|---|---|---|---|---|---|---|---|---|
|GGT|GTG|CAG|GAT|CTC|TTT|AAC|AGT|AGC|AAG|GCT|GAT|CTG|TCT|GGC|ATG|969|
|Gly|Val|Gln|Asp|Leu|Phe|Asn|Ser|Ser|Lys|Ala|Asp|Leu|Ser|Gly|Met| |
| | |295| | | | |300| | | | |305| | | | |
|TCA|GGA|GCC|AGA|GAT|ATT|TTT|ATA|TCA|AAA|ATT|GTC|CAC|AAG|TCA|TTT|1017|
|Ser|Gly|Ala|Arg|Asp|Ile|Phe|Ile|Ser|Lys|Ile|Val|His|Lys|Ser|Phe| |
| | |310| | | | |315| | | | |320| | | | |
|GTG|GAA|GTG|AAT|GAA|GAG|GGA|ACA|GAG|GCG|GCA|GCT|GCC|ACA|GCA|GGC|1065|
|Val|Glu|Val|Asn|Glu|Glu|Gly|Thr|Glu|Ala|Ala|Ala|Ala|Thr|Ala|Gly| |
| |325| | | | |330| | | | |335| | | | | |
|ATC|GCA|ACT|TTC|TGC|ATG|TTG|ATG|CCC|GAA|GAA|AAT|TTC|ACT|GCC|GAC|1113|
|Ile|Ala|Thr|Phe|Cys|Met|Leu|Met|Pro|Glu|Glu|Asn|Phe|Thr|Ala|Asp| |
|340| | | | |345| | | | |350| | | | |355| |
|CAT|CCA|TTC|CTT|TTC|TTT|ATT|CGG|CAT|AAT|TCC|TCA|GGT|AGC|ATC|CTA|1161|
|His|Pro|Phe|Leu|Phe|Phe|Ile|Arg|His|Asn|Ser|Ser|Gly|Ser|Ile|Leu| |
| | | | |360| | | | |365| | | | |370| | |
|TTC|TTG|GGG|AGA|TTT|TCT|TCC|CCT|TAGAAGAAAG|AGACTGTAGC|AATACAAAAA| | | | |1215|
|Phe|Leu|Gly|Arg|Phe|Ser|Ser|Pro| | | | | | | | | |
| | |375| | | | |380| | | | | | | | | |

TCAAGCTTAG TGCTTTATTA CCTGAGTTTT TAATAGAGCC AATATGTCTT ATATCTTTAC        1275

CAATAAAACC ACTGTCCAGA AACAAAAAAA AAAAAAAAA A        1316

( 2 ) INFORMATION FOR SEQ ID NO:13:

( i ) SEQUENCE CHARACTERISTICS:
        ( A ) LENGTH: 1152 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens ( i x ) FEATURE:
        ( A ) NAME/KEY: CDS
        ( B ) LOCATION: 13..1152
        ( D ) OTHER INFORMATION: /codon_start= 49

( i x ) FEATURE:
        ( A ) NAME/KEY: mat_peptide
        ( B ) LOCATION: 13..1149

( x i ) SEQUENCE DESCRIPTION: SEQ ID NO:13:

| | | | | | | | | | | | | | | | | |
|---|---|---|---|---|---|---|---|---|---|---|---|---|---|---|---|---|
|TCGGTTTTCA|CC|ATG|GAG|CAG|CTG|AGC|TCA|GCA|AAC|ACC|CGC|TTC|GCC| | |48|
| | |Met|Glu|Gln|Leu|Ser|Ser|Ala|Asn|Thr|Arg|Phe|Ala| | | |
| | |1| | |5| | | | |10| | | | | | |
|TTG|GAC|CTG|TTC|CTG|GCG|TTG|AGT|GAG|AAC|AAT|CCG|GCT|GGA|AAC|ATC|96|
|Leu|Asp|Leu|Phe|Leu|Ala|Leu|Ser|Glu|Asn|Asn|Pro|Ala|Gly|Asn|Ile| |
| | |15| | | | |20| | | | |25| | | | |
|TTC|ATC|TCT|CCC|TTC|AGC|ATT|TCA|TCT|GCT|ATG|GCC|ATG|GTT|TTT|CTG|144|
|Phe|Ile|Ser|Pro|Phe|Ser|Ile|Ser|Ser|Ala|Met|Ala|Met|Val|Phe|Leu| |
| |30| | | | |35| | | | |40| | | | | |
|GGG|ACC|AGA|GGT|AAC|ACG|GCA|GCA|CAG|CTG|TCC|AAG|ACT|TTC|CAT|TTC|192|
|Gly|Thr|Arg|Gly|Asn|Thr|Ala|Ala|Gln|Leu|Ser|Lys|Thr|Phe|His|Phe| |
|45| | | | |50| | | | |55| | | | |60| |
|AAC|ACG|GTT|GAA|GAG|GTT|CAT|TCA|AGA|TTC|CAG|AGT|CTG|AAT|GCT|GAT|240|
|Asn|Thr|Val|Glu|Glu|Val|His|Ser|Arg|Phe|Gln|Ser|Leu|Asn|Ala|Asp| |
| | | | |65| | | | |70| | | | |75| | |
|ATC|AAC|AAA|CGT|GGA|GCG|TCT|TAT|ATT|CTG|AAA|CTT|GCT|AAT|AGA|TTA|288|
|Ile|Asn|Lys|Arg|Gly|Ala|Ser|Tyr|Ile|Leu|Lys|Leu|Ala|Asn|Arg|Leu| |

-continued

```
                        80                            85                              90
TAT  GGA  GAG  AAA  ACT  TAC  AAT  TTC  CTT  CCT  GAG  TTC  TTG  GTT  TCG  ACT              336
Tyr  Gly  Glu  Lys  Thr  Tyr  Asn  Phe  Leu  Pro  Glu  Phe  Leu  Val  Ser  Thr
          95                       100                      105

CAG  AAA  ACA  TAT  GGT  GCT  GAC  CTG  GCC  AGT  GTG  GAT  TTT  CAG  CAT  GCC              384
Gln  Lys  Thr  Tyr  Gly  Ala  Asp  Leu  Ala  Ser  Val  Asp  Phe  Gln  His  Ala
     110                      115                      120

TCT  GAA  GAT  GCA  AGG  AAG  ACC  ATA  AAC  CAG  TGG  GTC  AAA  GGA  CAG  ACA              432
Ser  Glu  Asp  Ala  Arg  Lys  Thr  Ile  Asn  Gln  Trp  Val  Lys  Gly  Gln  Thr
125                      130                      135                      140

GAA  GGA  AAA  ATT  CCG  GAA  CTG  TTG  GCT  TCG  GGC  ATG  GTT  GAT  AAC  ATG              480
Glu  Gly  Lys  Ile  Pro  Glu  Leu  Leu  Ala  Ser  Gly  Met  Val  Asp  Asn  Met
                    145                      150                      155

ACC  AAA  CTT  GTG  CTA  GTA  AAT  GCC  ATC  TAT  TTC  AAG  GGA  AAC  TGG  AAG              528
Thr  Lys  Leu  Val  Leu  Val  Asn  Ala  Ile  Tyr  Phe  Lys  Gly  Asn  Trp  Lys
               160                      165                      170

GAT  AAA  TTC  ATG  AAA  GAA  GCC  ACG  ACG  AAT  GCA  CCA  TTC  AGA  TTG  AAT              576
Asp  Lys  Phe  Met  Lys  Glu  Ala  Thr  Thr  Asn  Ala  Pro  Phe  Arg  Leu  Asn
          175                      180                      185

AAG  AAA  GAC  AGA  AAA  ACT  GTG  AAA  ATG  ATG  TAT  CAG  AAG  AAA  AAA  TTT              624
Lys  Lys  Asp  Arg  Lys  Thr  Val  Lys  Met  Met  Tyr  Gln  Lys  Lys  Lys  Phe
     190                      195                      200

GCA  TAT  GGC  TAC  ATC  GAG  GAC  CTT  AAG  TGC  CGT  GTG  CTG  GAA  CTG  CCT              672
Ala  Tyr  Gly  Tyr  Ile  Glu  Asp  Leu  Lys  Cys  Arg  Val  Leu  Glu  Leu  Pro
205                      210                      215                      220

TAC  CAA  GGC  GAG  GAG  CTC  AGC  ATG  GTC  ATC  CTG  CTG  CCG  GAT  GAC  ATT              720
Tyr  Gln  Gly  Glu  Glu  Leu  Ser  Met  Val  Ile  Leu  Leu  Pro  Asp  Asp  Ile
                    225                      230                      235

GAG  GAC  GAG  TCC  ACG  GGC  CTG  AAG  AAG  ATT  GAG  GAA  CAG  TTG  ACT  TTG              768
Glu  Asp  Glu  Ser  Thr  Gly  Leu  Lys  Lys  Ile  Glu  Glu  Gln  Leu  Thr  Leu
               240                      245                      250

GAA  AAG  TTG  CAT  GAG  TGG  ACT  AAA  CCT  GAG  AAT  CTC  GAT  TTC  ATT  GAA              816
Glu  Lys  Leu  His  Glu  Trp  Thr  Lys  Pro  Glu  Asn  Leu  Asp  Phe  Ile  Glu
          255                      260                      265

GTT  AAT  GTC  AGC  TTG  CCC  AGG  TTC  AAA  CTG  GAA  GAG  AGT  TAC  ACT  CTC              864
Val  Asn  Val  Ser  Leu  Pro  Arg  Phe  Lys  Leu  Glu  Glu  Ser  Tyr  Thr  Leu
     270                      275                      280

AAC  TCC  GAC  CTC  GCC  CGC  CTA  GGT  GTG  CAG  GAT  CTC  TTT  AAC  AGT  AGC              912
Asn  Ser  Asp  Leu  Ala  Arg  Leu  Gly  Val  Gln  Asp  Leu  Phe  Asn  Ser  Ser
285                      290                      295                      300

AAG  GCT  GAT  CTG  TCT  GGC  ATG  TCA  GGA  GCC  AGA  GAT  ATT  TTT  ATA  TCA              960
Lys  Ala  Asp  Leu  Ser  Gly  Met  Ser  Gly  Ala  Arg  Asp  Ile  Phe  Ile  Ser
                    305                      310                      315

AAA  ATT  GTC  CAC  AAG  TCA  TTT  GTG  GAA  GTG  AAT  GAA  GAG  GGA  ACA  GAG             1008
Lys  Ile  Val  His  Lys  Ser  Phe  Val  Glu  Val  Asn  Glu  Glu  Gly  Thr  Glu
               320                      325                      330

GCG  GCA  GCT  GCC  ACA  GCA  GGC  ATC  GCA  ACT  TTC  TGC  ATG  TTG  ATG  CCC             1056
Ala  Ala  Ala  Ala  Thr  Ala  Gly  Ile  Ala  Thr  Phe  Cys  Met  Leu  Met  Pro
          335                      340                      345

GAA  GAA  AAT  TTC  ACT  GCC  GAC  CAT  CCA  TTC  CTT  TTC  TTT  ATT  CGG  CAT             1104
Glu  Glu  Asn  Phe  Thr  Ala  Asp  His  Pro  Phe  Leu  Phe  Phe  Ile  Arg  His
     350                      355                      360

AAT  TCC  TCA  GGT  AGC  ATC  CTA  TTC  TTG  GGG  AGA  TTT  TCT  TCC  CCT  TAA             1152
Asn  Ser  Ser  Gly  Ser  Ile  Leu  Phe  Leu  Gly  Arg  Phe  Ser  Ser  Pro
365                      370                      375                      380
```

( 2 ) INFORMATION FOR SEQ ID NO:14:

( i ) SEQUENCE CHARACTERISTICS:
        ( A ) LENGTH: 24 base pairs
        ( B ) TYPE: nucleic acid ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:14:

CGGAATTCGG TTTTCACCAT GGAG 24

( 2 ) INFORMATION FOR SEQ ID NO:15:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:15:

GGAGATCTAA GGGGAAGAAA ATCTCCC 27

( 2 ) INFORMATION FOR SEQ ID NO:16:

( i ) SEQUENCE CHARACTERISTICS:
        ( A ) LENGTH: 83 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( i x ) FEATURE:
        ( A ) NAME/KEY: intron ( x i ) SEQUENCE DESCRIPTION: SEQ ID NO:16:

GTGAGGTGAG GTAACTGTAC AGAGTCATGC ATTGCTCTAA AAGAATGCAG AGAATAATTT 60

CAGTGATTTT TAAATCTGTT CAG 83

HUMAN MONOCYTE ELASTASE INHIBITOR ANTIBODIES

RELATED APPLICATIONS

The present application is a continuation of application Ser. No. 08/315,831, filed Sep. 30, 1994, now issued as U.S. Pat. No. 5,663,299 which is a continuation-in-part of application Ser. No. 07/755,461, filed Sep. 6, 1991 now issued as U.S. Pat. No. 5,370,991, which is a continuation-in-part of application Ser. No. 07/314,383, filed Feb. 23, 1989, now abandoned. The entire contents of the above-identified patent applications are incorporated herein by reference.

GOVERNMENT SUPPORT

The invention described herein was supported in part by grants AI-20185 and HL-41579 from the National Institutes of Health.

BACKGROUND OF THE INVENTION

This invention relates in general to molecular biology, pharmacology and medicine and in particular to the isolation, purification and cloning of a human elastase inhibitor.

Preservation of the integrity of local organ function requires a delicate balance of the activities of phagocytic cell proteinases and the action of proteinase inhibitors. Loss of this balance is believed to be a major causative factor in the pathogenesis of asthma, chronic bronchitis, cystic fibrosis, emphysema, sarcoidosis, respiratory distress syndromes, arthritis, certain skin diseases and possibly malignancies. For example, excess release of elastase by neutrophils and monocytes, as well as excess accumulation of monocytes and neutrophils, are believed to be responsible for tissue injury in inflammatory conditions (e.g., arthritis, emphysema) and in neutrophil mediated injury to endothelial cells. The ability to monitor and control the proteinase-proteinase inhibitor balance requires that the relevant proteins be identified, isolated and purified.

An important phagocytic cell proteinase is the serine active site proteinase that is commonly referred to as "neutrophil elastase". Human neutrophil elastase is a glycosylated, 218 amino acid protein that is particularly abundant in neutrophils (0.5% of total protein) and is also found in monocytes and macrophages. The elastase cleaves extracellular matrix proteins, including elastin, proteoglycans, fibronectin, type III and type IV collagen, and certain soluble proteins. The enzyme also is required for neutrophil migration through cell barriers in vitro. The existence of elastase inhibitors in vivo is evident from the neutrophil turnover rate. Despite the fact that neutrophils enter most body sites, a turnover of about $10^{11}$ neutrophils (with a content of about 50 mg elastase) occurs daily in humans without evidence of uncontrolled tissue degradation.

α1-antitrypsin (α1-AT) is a fast-acting elastase inhibitor. Individuals with genetically reduced levels of α1-AT (homozygous Z-variant) are predisposed to develop pulmonary emphysema due to uncontrolled elastase action in the third or fourth decade of life. Human α1-AT currently is used to treat congenital α1-AT deficiency.

In addition to α1-AT, other naturally-occurring inhibitors of neutrophil elastase activity have been detected in monocytes and neutrophils in several species. An endogenous elastase inhibitor has been reported in the cytosolic fraction of human blood leukocytes and human lung macrophages (Janoff, A. and Blondin, J., *Proc. Soc. Exp. Biol. Med.* 136:1050–1053 (1971); Blondin, J. et al., *Am. Rev. Resp. Dis.* 106:477–479 (1972)). Cytosolic proteins that inhibit elastase have been identified and purified from horse blood neutrophils (Dubin, A., *Eur. J. Biochem*, 73:429–435 (1977); Potempa, J. et al., *J. Biol. Chem*, 263:7364 (1988)), pig blood leukocytes (Kopitar, M. and M. Bozic, *Acta Pharm. Jugosl.* 35:203–212 (1985)) and bovine lung macrophages (Valentine, R. et al., *Proc. Soc. Exp. Biol. Med.* 168:238–244 (1981)). An elastase inhibitor in the extracellular fluid of cultured guinea pig macrophages has been identified based upon its ability to form a covalent complex with elastase (Remold-O'Donnell, E. and K. Lewandrowski, *J. Biol. Chem.* 258:3251–3257 (1983)). Larger quantities of the guinea pig elastase inhibitor have been found in macrophage lysates (Remold-O'Donnell, E. and K. Lewandrowski, *J. Biol. Chem.* 258:3251–3257 (1983)). More recently, a prevalent, fast-acting endogenous elastase inhibitor protein has been detected in mature human monocytes and monocyte-like cells (Remold-O'Donnell, E., *J. Exp. Med.* 162:2142–2155 (1985)). However, isolation, purification, characterization and cloning of the human monocyte elastase inhibitor has not been reported.

SUMMARY OF THE INVENTION

According to one aspect of the invention, Human Monocyte Elastase Inhibitor (alternatively referred to herein as Human EI or HEI) has been isolated, purified, cloned and characterized at the molecular level. The cytosolic Human EI has a molecular weight of about 42 kD, is stable to reducing agents, non-glycosylated, forms a covalent complex with elastase and inhibits the elastinolytic activity of elastase. The inhibitor includes a cysteine residue that is essential for interaction with elastase and appears to have a blocked amino-terminus.

Human EI has been digested, purified and partially sequenced and includes Sequence I.D. Numbers 1–11. Human EI also has been cloned by recombinant DNA techniques and sequenced (Sequence I.D. Number 12). The coding sequence of the Human EI cDNA (Sequence I.D. Number 13) has been expressed using a baculovirus expression system in insect cells. Thus, in addition to purified (isolated) or substantially purified Human EI from monocytes and/or a monocyte-like cell line, the invention also provides recombinantly derived Human EI and its functional variants that are capable of forming a complex with an elastase and/or inhibiting the elastinolytic activity of elastase. Such functionally equivalent variants include peptides derived from the Human EI by enzymatic cleavage (e.g., trypsin), peptides/proteins derived from the Human EI by enzymatic or chemical cleavage of amino acids from the 5' and/or 3' terminal end of the Human EI and analogs of these peptides/proteins (e.g., peptides including conservative amino acid substitutions), provided that the functionally equivalent variants are capable of forming a complex with elastase and/or inhibiting the elastinolytic activity of elastase.

A human cDNA library from a monocyte-like cell line was expressed in *E. coli* using conventional expression vectors to yield plaques, each plaque expressing a different portion of the cDNA library. The plaques were screened using an oligonucleotide encoding at least a portion of one of Sequence I.D. Numbers 1–11. Thereafter, recombinant expression vectors were isolated from selected plaques, each vector containing a portion of the cDNA sequence for Human EI. The sequences were excised and sequenced. The DNA sequence for the human elastase inhibitor was obtained by identifying overlapping sequences in the DNA fragments and in DNA amplified from monocyte-like and neutrophil-like cDNA libraries. Unique restriction sites were identified in the composite cDNA sequence for human EI, thereby providing a convenient mechanism for making the full length cDNA clone and for insertion of the cDNA into a suitable expression system.

The coding sequence of the Human EI cDNA was expressed using a baculovirus/insect cell expression system. Surprisingly, most of the expressed protein was found in the extracellular fluid and expression was greatest at five to six days following infection.

A functionally active elastase inhibitor of the invention is selected from the group consisting of:

(1) Human Monocyte Elastase Inhibitor;

(2) functionally equivalent polypeptides of Human Monocyte EI (i.e., peptides/proteins that are derived from Human EI and which are capable of forming a covalent complex with elastase and/or inhibiting the elastinolytic activity of elastase); and (3) functionally equivalent polypeptide analogs of Human monocyte EI (i.e., peptides/proteins that are derived from Human EI but which contain conservative amino acid substitutions and which are capable of forming a complex with elastase and/or inhibiting the elastinolytic activity of elastase.

Isolated and substantially pure preparations of oligonucleotides encoding Human Monocyte EI peptides and/or functionally equivalent peptide analogs of Human EI also are provided. These oligonucleotides may be the product of natural, synthetic or recombinant methods. In addition, sense or antisense DNA or RNA corresponding to the disclosed oligonucleotides are provided. Likewise, preparation(s) of antibodies with selective specificity for Human EI, its functionally equivalent peptides and functionally equivalent peptide analogs also are provided.

The invention also provides a method for producing functionally equivalent peptides and peptide analogs of the Human EI protein. The method includes providing a modified DNA sequence encoding a putative functionally equivalent peptide of Human EI, inserting the modified DNA sequence into a suitable expression system; expressing the modified Human EI; and testing the ability of the modified Human EI to bind to and inhibit the elastinolytic activity of elastase. The modified Human EI also can be tested for its ability to bind to and/or inhibit the proteolytic activity of other proteases such as proteinase-3.

The successful expression of recombinant Human EI is disclosed herein. Sf9 insect cells infected with the recombinant baculovirus AcNPV-HEI expressed Human EI (HEI) as a cytoplasmic protein early (2–4 days) and synthesized and released high levels of the protein late (5–7 days) after infection. The amount of released recombinant HEI was ~50 ug per $10^6$ cells. Released recombinant HEI (i.e., HEI found in the extracellular fluid) was indistinguishable from naturally occurring EI isolated from human monocytes in its physicochemical features, molecular weight, isoelectric focusing, reactivity with antiserum and absence of glycosylation. Released recombinant Human EI also was indistinguishable from monocyte Human EI in its ability to form a covalent complex with and inactivate human neutrophil elastase and porcine pancreatic elastase, the two known activities of the naturally occurring inhibitor.

Recombinant Human EI also inhibited the peptidase activity of and formed a covalent complex with, proteinase-3. Proteinase-3 shares with elastase the capacity to cleave elastin and cause lung matrix destruction and experimental emphysema (Janoff, A. (1985) *Ann. Rev. Med.* 36:2207–2216; Kao, R. et al. (1988) *J. Clin. Invest.* 82:1963–1973). Recombinant Human EI also appeared to form a covalent complex with cathepsin G; however, the inhibitor did not inhibit u-plasminogen activator. Cumulatively, these results suggest an important role for Human EI in regulating multiple serine proteases found at inflammatory sites in situ.

The above-described Human EI, antibodies to Human EI, oligonucleotides and vectors encoding Human EI, its functionally equivalent peptides and peptide analogs can be used alone or coupled with other moieties to treat various medical conditions and/or as diagnostic tools in determining the existence and degree of such conditions. The various utilities of the invention will become more apparent in view of the accompanying drawings and detailed description which follows.

BRIEF DESCRIPTION OF THE DRAWINGS

FIG. 4 shows the amino acid composition as determined for pure EI as compared to that of α1-AT, wherein the mean amino acid composition of >200 proteins is taken from Reeck, G. R. and Fisher, L. Int. *J. Peptide Protein Res.*, 1973, 5:109–117; EI values are means of data from three preparations. The number of residues per molecule EI were calculated based on Mr=42,000; the α-1AT composition is calculated based on Carrell, R. W. et al. *Nature*, 1982, 298:329–334 (N.D.=not determined);

(FIG. 7A) Human monocyte-like cells: Partially purified HEI from $5 \times 10^6$ cells U937 cells was fractionated by SDS/PAGE (reducing conditions) and transferred to nitrocellulose. The blot was probed with 1 to 250 dilutions of preimmune rabbit serum or serum obtained after immunization with pure U937 cell HEI, followed by $^{125}$I-labeled anti-rabbit IgG. Molecular mass marker proteins (kD) are indicated on the left. (FIG. 7B) Insect cell cultures: Sf9 cells were infected with wildtype (AcNPV) or recombinant (AcNPV-HEI) virus. After 4 days, aliquots of the culture (cells and media) derived from $2.5 \times 10^4$ starting cells were analyzed as above with 1 to 1000 dilutions of sera;

FIG. 9A shows Coomassie blue staining; FIG. 9B shows Western blot results. Harvest times and other details are as in FIGS. 8A–8D except that the samples represent $4\times10^4$ starting cells, i.e., a 7-fold smaller portion of the culture relative to the fractions in FIGS. 8A–8D. The small amount of rHEI observed at the earliest time points was attributable to the viral stock;

FIGS. 11A–11B show the effect of PNGase F on recombinant HEI from media of Sf9 cells infected with AcNPV-HEI. HEI was partially purified from 7 day serum-containing media of infected cells. Recombinant HEI (FIG. 11A) and α1-AT (FIG. 11B) were denatured and treated with the indicated concentrations of PNGase F. Shown is a "gold stained" transfer of an SDS/PAGE gel with molecular mass marker positions indicated on the right;

(FIG. 12A) Western blot with rabbit anti-HEI antiserum: The autoradiograph shows: A, 3.8 μg pure HEI from U937 cells; B, rHEI in day 6 media from $1.6\times10^4$ starting infected Sf9 cells; C, rHEI in the NP40-soluble fraction prepared on day 6 from $1.1\times10^5$ starting Sf9 cells. (FIG. 12B) Two-dimensional electrophoresis: Natural HEI (lysate of $3\times10^5$ U937 cells) or recombinant HEI (7 day media of $3.6\times10^3$ infected Sf9 cells) was preincubated with $^{125}$I-labeled pancreatic elastase to form the $^{125}$I-elastase-HEI covalent complex, which was examined by isoelectric focusing (horizontal axes; nearly linear pH gradient) and SDS/PAGE (vertical axes). The left panel of the autoradiograph shows the complex of U937 HEI; the right panel shows the complex of rHEI. The dotted lines trace the position of the complex of α1-AT;

FIG. 13C and 13D show the complex formation assay: Shown are gold-stained SDS/PAGE gels of 75 ng HNE (FIG. 13C, left lane) or PPE (FIG. 13D, left lane) and 6 μl rHEI (6 day media of infected Sf9 cells) (each middle lane) and the products of a 3 min co-incubation at 37° C. (each right lane). In each case, the new covalent complex is detected at 66 kD (arrows on the right) as previously shown for naturally occurring HEI;

FIG. 14C and 14D show the complex formation assay: Shown are gold-stained SDS/PAGE gels of 250 ng proteinase-3 (FIG. 14C, left lane) or cathepsin G (FIG. 14D, left lane) and 6 μl rHEI (6 day media of infected Sf9 cells) (each middle lane) and the products of a 3 min co-incubation at 47° C. (each right lane). In the case of proteinase-3, a new covalent complex of proteinase-3 and HEI is detected at 66 kD (arrow on the right); in the case of cathepsin G, a broad, higher molecular weight protein product was detected;

DETAILED DESCRIPTION OF THE INVENTION

Figure 1A:
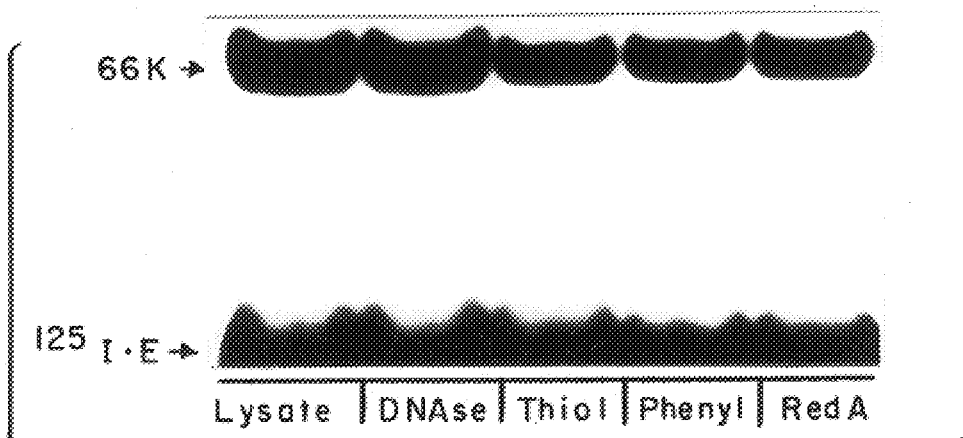
FIGS. 1A–1B are autoradiographs (FIG. 1A) showing the presence of Human EI at certain steps during purification and a protein-stained electrophoresis gel (FIG. 1B)

Human EI is a fast acting, cell-associated, essentially irreversible inhibitor of porcine pancreatic elastase and human neutrophil elastase, both serine active-site protein elastases (hereinafter "elastase"). It is found at high levels in neutrophils, monocytes and macrophages. Human EI reacts quantitatively with elastase to form an EI-elastase complex and to inhibit the elastinolytic activity of elastase. The complex is stable in boiling SDS (sodium dodecyl sulfate), indicating a covalent bond between the EI and the elastase.

Based on functional criteria, Human EI can be grouped with the serine proteinase inhibitors of the Serpin family. Human EI does not react with elastase that has been inactivated with the serine active site reagent DFP (diisopropyl fluorophosphate). The covalent complex is stable in boiling SDS and is susceptible to base-catalyzed cleavage. These mechanisms of action are characteristic of serine proteinase-inhibitors of the Serpin family. Human EI differs from other serine proteinase inhibitors in that treatment of Human EI with iodoacetamide abrogates its ability to form a complex with elastase, thus suggesting an essential cysteine residue. Human EI also differs from all other molecules based on searches of databases for the amino acid sequence derived from the cDNA encoding human EI.

Cytosolic Human EI is a single polypeptide having a molecular weight of about 42,000. The negligible levels of carbohydrate detected on gas-liquid chromatography and the insensitivity of Human EI to treatment with the glycosidase PNGase F (peptide:N-glycosidase F) indicate that cytosolic Human EI is non-glycosylated. The amino-terminus of purified Human EI appears to be blocked. Purification and partial sequence analysis demonstrated that the purified Human EI includes Sequence I.D. Numbers 1 through 11. A cDNA which includes the nucleic acid sequence encoding Human EI is disclosed in Sequence I.D. Number 12. A truncated cDNA (which encodes the coding region of Human EI) is disclosed in Sequence I.D. Number 13.

In addition to providing the primary structure for cytosolic Human EI, two discoveries disclosed herein have made possible the study of human EI in extracellular fluids. These developments include: (1) the generation in rabbits and mice of antibodies having specificity for Human EI (the antibodies are useful for detecting Human EI even in the presence of elastase) and (2) the discovery that exposure of monocytes to lipopolysaccharides (LPS) increases monocyte levels of the Human EI mRNA, These discoveries, coupled with the observation that Human EI includes five amino acid segments having the sequence, Asn-Xaa-Ser/Thr (the signal for addition of N-glycans by golgi region enzymes) and the relatedness of Human EI to known secreted proteins suggest that Human EI also can exist in an extracellular (possibly glycosylated) form.

The abundance of Human EI in monocytes, monocyte-like U937 cells, neutrophils and lung macrophages and its apparent absence in the lymphocyte-like cell line CEM suggests that expression of Human EI in situ is tightly regulated. Northern analysis of total RNA and poly(A)-purified mRNA revealed three Human EI-encoding mRNA species of 2.6, 1.9 and 1.5 kb in U937 cells and no detectable mRNA in the CEM lymphoblastoid cells. The Human EI-encoding mRNA in activated monocytes was characterized by allowing isolated, normal monocytes to mature in culture as adherent cells in serum-containing media for seven days, during which time they lost monocyte components and gained macrophage-like enzymes and properties. The Human EI-encoding mRNA in activated macrophages was characterized by treating macrophages with activating agents for four hours.

Following activation, RNA was isolated and examined by Northern analysis in accordance with standard procedures using $^{32}$P-labelled probes for plasminogen activator inhibitor-2 (PAI-2, as an internal control) and Human EI. The levels of PAI-2 mRNA were low in unstimulated macrophages, were increased by lipopolysaccharides (LPS) and were substantially increased by exposure to IFN-gamma, GM-CSF and/or infection with *Mycobacterium avium*. Levels of Human EI mRNA were substantial in untreated macrophages, greatly increased upon exposure to LPS and were not altered by the above-identified cytokines and *M. avium*. These results suggested that the closely related monocyte protease inhibitors, Human EI and PAI-2, are differently regulated. More significantly, LPS was identified as an agent which can increase transcription of the Human EI gene. This discovery permits examination of induction of Human EI gene expression and provides a method for modulating production of Human EI in a clinical setting, e.g., by identifying other agents which increase HEI expression as potential therapeutic agents.

The evidence presented herein suggests the existence of an extracellular form of Human EI including, for example, that Human EI is a member of the Ovalbumin family of serpins ("Ov-serpin" family). The Ov-serpin family was identified based upon a comparative study of serpin superfamily proteins (described in *FEBS Letter* 315:105–108 (1993)). The study included comparisons of amino acid sequence, protein characteristics and gene organization and defined a family grouping that would not have been recognizable on the basis of sequence identities alone. Because the Ov-serpin family includes some extremely well-characterized proteins and because there is a high level of relatedness between members of the Ov-serpin family, recognition of HEI as a member of the Ov-serpin family permitted several functional properties of human EI to be predicted. A brief review of the most relevant Ov-serpin family members follows.

Six Ov-serpins are known, including two chicken proteins and three proteins derived from human sources. The human Ov-serpins include HEI (disclosed herein), plasminogen activator inhibitor-2 (PAI-2), squamous cell carcinoma antigen (SCCA) and placental thrombin inhibitor (PTI) (Coughlin, P. et al., PNAS USA 90:9417–9421 (1993). The common features of these molecules include amino acid sequence identities (50% for each human pair) and nearly identical gene organization. Significantly, the most distinguishing feature at the protein level is the absence of the typical N-terminal cleavable signal sequence in Ov-serpins and the presence in some Ov-serpin of a non-cleavable internal hydrophobic signal sequence that mediates secretion. As discussed below, these common features suggest that human EI also can exist in an extracellular (possibly glycosylated) form.

Ovalbumin was the first secreted molecule to be identified in which a non-cleavable internal hydrophobic signal sequence was used to access the endoplasmic reticulum/golgi region glycosylating enzymes in the secretory pathway. Although the uncleaved signal sequence of ovalbumin has been reported to be located near the NH$_2$-terminus, the exact signal sequence has not been identified.

Plasminogen Activator-2 (PAI-2) is a cytoplasmic molecule found in monocytes, placenta and U937 cells. Upon stimulation of monocytes with lipopolysaccharides, or differentiation of U937 cells with phytohemagglutinin (PHA), the level of PAI-2 mRNA and extracellular expression of the protein reportedly increased significantly. Although the cytoplasmic PAI-2 protein is non-glycosylated, most of the extracellular PAI-2 of stimulated cells is glycosylated. The exact mechanism by which PAI-2 translation changes from the cytoplasmic to the secretory pathway has not been elucidated, however, a possible role for "heat shock proteins" has been proposed. This process is referred to as "facultative polypeptide translation", i.e., a single mRNA supports either synthesis of a non-glycosylated cytoplasmic protein or a secreted N-glycosylated protein, depending on the activation status of the cell.

Squamous Cell Carcinoma Antigen (SCCA) is a 45 kDa protein that is found as a non-glycosylated protein in the cytoplasm of normal squamous epithelial cells of the uterine cervix. Transformation of the normal cells in vivo produces carcinoma cells that secrete large amounts of SCCA. The SCCA protein reportedly also has been found at high levels in the serum of patients with squamous cell carcinoma of the uterine cervix and has been correlated to the disease progression. Like PAI-2, the SCCA protein is synthesized in either of two forms, a non-glycosylated cytoplasmic protein or a secreted acidic (possibly glycosylated) form, depending upon the state of the cell.

Each member of the Ov-serpin family includes one or more well known potential N-glycosylation amino acid sites. For example, ovalbumin has two N-glycosylation sites which are glycosylated (McReynolds L. et al., (1978) *Nature* 278:723–728; Woo S. et al., (1981) *Biochem.* 20:6437–6446), gene Y has four potential glycosylation sites that have not yet been studied (Heilig R. et al., (1982) *Nucl Acid Res.* 10:4363–4382), SCCA has four potential glycosylation sites and PAI-2 has three N-glycosylation sites (Ye R. et al., (1989) *J. Biol. Chem.* 264:5495–5502; Samia J. et al., 1990 *Genomics* 6:159–167). Secreted PAI-2 is a mixture of molecules including one, two or three N-glycans (Ye R. et al., (1988) *J. Biol. Chem.* 263:4869–4875).

Huber and Carrell have reported that although glycosylation positions vary extensively among serpin superfamily molecules, these sites invariably are present at the protein surface with asparagine residues projecting into solution (Huber R. et al., (1989) *Biochem.* 28:8951–8965. Using the α1-antitrypsin crystal coordinates to examine the position of the four potential N-glycosylation sites of human EI (the fifth human EI glycosylation site is not clear in the crystal structure), all four N-glycosylation sites of Human EI have been shown to be present at the surface of Human EI. The finding that each of two glycosylation sites are located on different sides of the molecule (where N-glycans, if attached, would project into solution), suggests that the four Human EI putative glycosylation sites satisfy at least this criterion for glycosylation.

I. PURIFICATION OF NATURALLY-OCCURRING HUMAN EI

A series of purification steps were used to purify the naturally-occurring Human EI from a monocyte-like cell line. The presence of Human EI was confirmed at each stage in the purification by evaluating the ability of an aliquot of the sample taken at each step to form a covalent complex with $^{125}$I-elastase (Remold-O'Donnell, E. and K. Lewandrowski, *J. Biol. Chem.* 258:3251–3257 (1983); Remold-O'Donnell, E., *J. Exp. Med.* 162:2142–2155 (1985)). The details of the confirmation procedure are set forth in the foregoing references, the disclosures of which are incorporated herein by reference. Briefly, fractions suspected of containing Human EI were incubated at 37° C. for 10 minutes with 30–200 ng of $^{125}$I-labeled porcine pancreatic or $^{125}$I-labeled human neutrophil elastase (Elastin Products, Owensville, Mo.). The covalent EI-elastase complex was detected by autoradiography following SDS polyacrylamide gel-electrophoresis using the Fairbanks/Laemmli gel system. This system employs a relatively low pH and low primary amine concentration to minimize hydrolysis of the complex during electrophoresis (Remold-O'Donnell, E., *J. Exp. Med.* 162:2142–2155 (1985)).

(A). Obtaining Cell Lysates.

U937 cells are human histiocytic lymphoma cells (originally described in Sundström, C. and Nilsson, K. *Int. J. Cancer* 17: 565–577 (1976)). The particular U937 cells used ("U937-EI") represent a subline that is at a slightly more advanced stage of differentiation with respect to the U937 cells originally described by Sundström, C. and Nilsson, K. supra. This U937-EI cell line was deposited at the ATCC, Rockville, Md., under Accession Number CRL 10026 on Feb. 3, 1989.

U937-EI cells were grown in RPMI 1640 medium or Dulbecco's modified Eagles medium with 4.5 mg/ml glucose, 10% FCS and 50 micrograms per ml gentamycin. The U937-EI cells from 12 liter cultures (approximately $1.8 \times 10^{10}$ cells) grown by the Massachusetts Institute of Technology Cell Culture Center were washed twice by pelleting at 4° C. in $Ca^{++}/Mg^{++}$ containing PBS. Following incubation of the cells (at $2 \times 10^7$ per ml in HBSS (Hanks'

Balanced Salt Solution)), at about 22° C. for 15 minutes to remove adsorbed α1-AT (Remold-O'Donnell, E., *J. Exp. Med.* 162:2142–2155 (1985)), the cells were brought to 4° C. and pelleted. Lysates ($2.5 \times 10^7$ cells per ml) were prepared by extracting the cells with 0.5% Nonidet P-40 (NP-40) in PBS for 4 minutes at about 22° C. and 10 minutes at 4° C., and clarified by centrifugation in a Sorvall SS34 rotor (Dupont Co., Wilmington, Del.) at 18,000 rpm for 30 minutes at 4° C. NP-40 is a nonionic detergent marketed in the United States by Gallard Schlesinger, Carle Place, N.Y.). The material is an octyl phenol ethylene oxide condensate containing 9 moles ethylene oxide; it is a product of BDH Limited, Poole, England.

(B). Separation of Actin on DNAse-Sepharose.

In preliminary purification experiments, EI activity was lost concomittant with the formation of actin-containing precipitates. To prevent this activity loss, cell lysates were immediately chromatographed on DNAse-Sepharose, a resin which specifically absorbs actin (Lazardes, E and Lindberg, U. *Proc. Natl. Acad. Sci. USA* 71:4742–6 (1974)).

The DNAse Sepharose affinity resin was prepared as follows: Deoxyribonuclease I (bovine pancreas; 1800 Kunitz units/mg protein;. Sigma Chemical Co., St. Louis, Mo.) was treated with 2 mM diisopropyl-fluorophosphate (DFP) in PBS for 30 min at 22° C., and was coupled at 3 mg/ml in 0.1M NaHCO$_3$, pH 8.5 to activated Sepharose by mixing for 18 hr at 4° C. (greater than 90% coupling efficiency). The activated Sepharose was either Activated Sepharose 4B (supplied as an activated lyophilized powder by Pharmacia Fine Chemical, now Pharmacia LKB Biotechnology, Inc., Piscataway, N.J.), which was reconstituted and prepared for coupling according to manufacturer instructions (i.e., reconstituted with 1 mM HCl and washed with 1 mM HCl at 22° C. for 15 min., followed by washing with coupling buffer) or Sepharose 6B activated immediately before coupling by treatment with CNBr (2.3 g per 100 ml Sepharose) at pH 11 and ~22° C. for 10 min. (P. Cuatrecasas, *J. Biol. Chem.*, 1970, 245: 3509–3065). The resin was treated at 22° C. once with 10 mM Tris-HCl buffer, pH 8.0 for 2 hr; three cycles with 100 mM sodium acetate buffer pH 4.0 followed by 100 mM NaHCO$_3$ pH 8.5; once with PBS; and once with 2 mM DFP in PBS for 30 min. The resin was stored in PBS with 0.02% sodium azide at 4° C. and was equilibrated with PBS immediately before use.

Figure 1B:
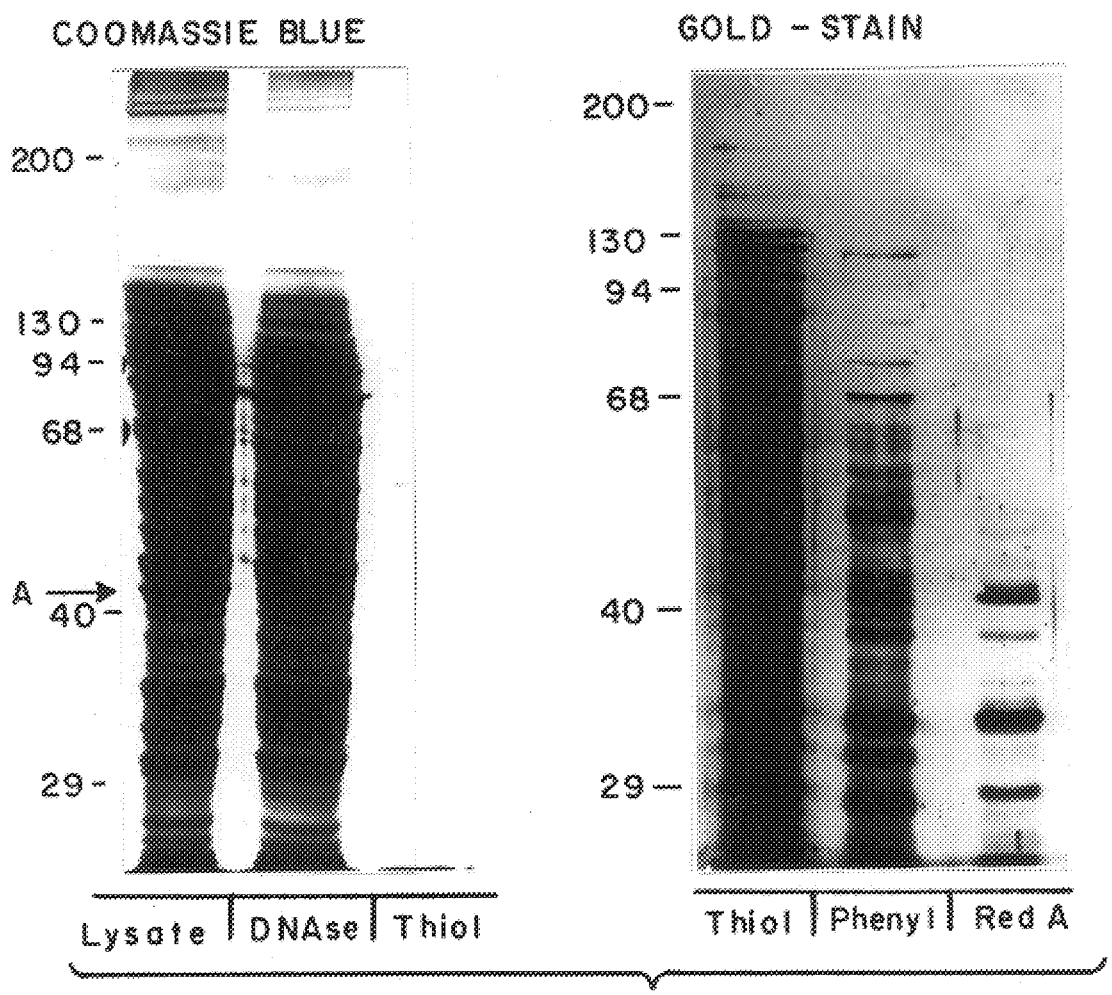

The cell lysate (~720 ml) was incubated with 180 ml DNAse-Sepharose for 30 minutes at 4° C. in a roller bottle. The mixture was transferred to a 6.5 cm diameter column, and the nonadherent fraction, together with a 0.8 column volume wash with 0.5% NP-40 in PBS, was stored at −70° C. The presence of Human EI in the nonadherent fraction was measured as set forth above. As shown in FIG. 1, a protein in the nonadherent fraction combined with elastase to form an $^{125}$I-elastase—elastase inhibitor complex of apparent molecular weight 66,000.

(C). Thiopropyl-Sepharose-6B Separation.

Thiopropyl-Sepharose 6B is a mixed disulfide affinity resin supplied by Pharmacia Fine Chemicals. It contains approximately 20 μmoles of 2-thiopyridyl residues in mixed disulfide linkages to hydroxypropyl residues per ml swollen gel; the latter residues are linked to the Sepharose 6B matrix via ether linkages. Thiopropyl-Sepharose 6B can be synthesized by a method such as that described by R. Axen, Drevin, H. and Carlsson, J., *Acta Chem. Scand. B*, 1975, 29, 471–474). In contrast to most proteins, Human EI adhered to the Thiopropyl-Sepharose-6B resin.

The Thiopropyl-Sepharose-6B was equilibrated with 0.5% NP-40, 10 mM Tris-HCl buffer, pH 7.4, 150 mM NaCl, 1 mM EDTA (NP-40/Tris/150-NaCl/EDTA) at 22° C. for 30 min. The DNAse-nonadherent fraction (~900 ml) was incubated with occasional stirring at 22° C. with 30 ml of the Thiopropyl-Sepharose-6B. The mixture was transferred to a 3 cm column and washed sequentially with one column volume each of NP-40/Tris/150-NaCl/EDTA, NP-40/Tris/ 500-NaCl, Tris/500-NaCl, and Tris/150-NaCl. The Human EI was eluted from the column with 50 mM mercaptoethanol in Tris/150-NaCl to yield a single 70 ml "Thiol eluate" fraction. Again, the presence of Human EI was confirmed as set forth above. As shown in FIG. 1, a protein in the Thiol eluate fraction combined with elastase to form the $^{125}$I-elastase—elastase inhibitor complex.

(D). Phenyl-Sepharose-CL4B Separation.

Sepharose is the registered trademark for spherical agarose gel beads manufactured by Pharmacia Fine Chemicals. Sepharose 6B, ~6% agarose contains 40–210 micron particles; Sepharose 4B, ~4% agarose contains ~40–190 micron particles (See, e.g., Hjerten, S., *Biochem. Biophys. Acta* 1962, 62: 445–449 and S. Hjerten, "Methods in Immunology and Immunochemistry", Ed: M. W. Chase and C. A. Williams, Academis Press, Inc., New York, 1968, pages 149–154).

Phenyl-Sepharose-CL4B is a derivative of Sepharose CL-4B; the latter resin is prepared by crosslinking agarose with 2,3-dibromopropanol (see, e.g., UK Patent I 352 613) and desulphating the resulting gel by alkaline hydrolysis under reducing conditions (J. Porath, et al., *J. Chromatogr.*, 1971, 60: 167–177). Phenyl groups are introduced by reaction of Sepharose CL-4B with the glycidyl ether to produce a derivative with the phenyl group attached to the monosaccharide unit of the agarose matrix via an ether linkage (S. Hjerten, et al., *Chromatogr.*, 1974, 101:281–288). The concentration of coupled phenol ligand is approximately 40 $\mu$moles/ml swollen gel.

The Human EI-containing fraction of the Thiol-eluate was applied at approximately 22° C. to a 3.5 cm column of Phenyl-Sepharose-CL4B (70 ml; Pharmacia) that had been equilibrated with 10 mM Tris-HCl buffer, pH 7.4, 150 mM NaCl, 1 mM mercaptoethanol (Tris/150-NaCl/ME). Phenyl-Sepharose-CL4B separates proteins based on differences in hydrophobicity. The nonadherent, Human EI-containing fraction was collected, together with a 20 ml (approximately) column wash using Tris/150-NaCl/ME. The presence of Human EI in the nonadherent fraction was confirmed as set forth above (FIG. 1).

(E). Matrix gel Red A separation.

Matrix gel Red A is a "group selective" affinity resin marketed by Amicon Corp., Lexington, Mass. It consists of crosslinked 5% agarose with 3–5 mg of covalently coupled dye per ml swollen gel. The dye is known alternatively as red A, reactive red 120 and Procion Red HE3B, a registered trademark of Imperial Chemical Industries (Baird, J., et al., *FEBS Lett.*, 70: 61).

The Phenyl-nonadherent fraction (approximately 110 ml) was diluted with 0.5 volume Tris/ME and applied at 4° C. to a 2 cm diameter column of 20 ml Matrix gel Red A that had been equilibrated with Tris/100-NaCl/ME. Matrix gel Red A separates proteins based on their ability to bind to the Red A dye. The nonadherent, Human EI-containing fraction, including one column volume wash with Tris/100-NaCl/ ME, was collected, tested for the presence of Human EI (FIG. 1), dialyzed against Tris/50-NaCl/ME for 3 hr at 4° C., and stored at -70° C.

(F). HPLC DEAE-5PW Separation.

DEAE-5PW is a weak anion exchange HPLC resin that separates proteins based on differences in charge. DEAE-5PW is prepared by introducing diethylaminoethyl (DEAE) groups onto a hydrophilic rigid resin; it is a product of Waters Chromatography, Milford, Mass. and also is known as Protein-Pak DEAE-5PW (Protein-Pak is a tradename for various Waters resins). The resin includes 0.1 micromole of effective DEAE groups per ml of resin. DEAE-5PW is a 10 micron spherical diethylaminoethyl functionalized polymethacrylate resin having 1000 angstrom pores. The resin is encased in a 7.5×75 mm stainless steel column.

Portions (50 ml) of the dialyzed Red A-nonadherent fraction were filtered through 0.2 $\mu$m nylon membranes (Schleicher and Schuell, Keene, N.H.) and applied at 0.8 ml/min to a DEAE-5PW column previously equilibrated with Tris/50-NaCl/ME at 22° C. The column was washed with equilibration buffer and Human EI was eluted by applying Tris/85-NaCl/ME and collecting fractions which absorbed light at 280 nm. The fractions were assayed for the presence of Human EI as set forth above.

To concentrate the Human EI, active fractions from 3–4 DEAE-fractionations were pooled, diluted with Tris/ME, and reapplied to the DEAE-5PW column equilibrated in Tris/50-NaCl/ME. A single Human EI-containing fraction containing 1 to 2.5 ml was eluted with Tris/140-NaCl/ME. The presence of Human EI was confirmed as above. This fraction was 85–95% pure Human EI (as indicated by gold-stained SDS electrophoresis gels), active, concentrated (e.g., 0.4 mg/ml), and was used to perform the initial activity and functional studies of the naturally-occurring Human EI described below.

(G). HPLC-Gel Filtration Chromatography.

For some applications, the remaining contaminants were removed by HPLC gel filtration chromatography using the HPLC gel filtration resin Protein-Pak I-125. Protein-Pak I-125, a product of Waters Chromatography, is a 10 micron diol-bonded silica gel with a 100 Angstrom pore size. It consists of irregular silica particles covalently bonded with a dihydroxyalkyl silane to generate a hydrophilic material that is non-adsorptive toward proteins and is suitable for gel filtration chromatography. The resin is supplied encased in 7.8×30 mm column.

Portions of pooled, concentrated Human EI from DEAE-5PW (200–1000 $\mu$l) were subjected to gel filtration chromatography at 1.0 ml/min on two Protein-Pak I-125 columns in series (totaling 7.8×600 mm). The columns were previously equilibrated with 10 mM Tris HCl buffer, pH 7.4, 90 mM NaCl. Fractions which absorbed light at 214 nm (two peaks) were collected and following addition of mercaptoethanol to 1 mM, were assayed for the presence of Human EI as set forth above. The pooled active peak (second peak) represented pure or substantially pure Human EI. Alternatively, HPLC gel filtration can be performed using 50 mM $NH_4HCO_3$ as the column buffer, in which instance, the buffer can be removed from the Human EI-containing fraction by lyophilization.

At each stage in the purification, fractions were analyzed by Laemmli SDS-electrophoresis (Remold-O'Donnell, E.,*J. Exp. Med.* 162:2142–2155 (1985)). The polypeptides were gold stained after transfer to PVDF membranes (polyvinylidine difluoride; 0.45 $\mu$m; Millipore Corp., Bedford, Mass.) (constant 70 mAmps; 160v/1.6A power supply; Bio-Rad Laboratories, Richmond, Calif.) with 42 mM Tris/190 mM glycine buffer, pH 8.3 for 18 hr at ~22° C. (Transphor Cell; Hoefer Scientific, San Francisco, Calif.). The PVDF membranes were washed seven times with 0.1% Tween-20 in PBS (2×15 min; 5×5 min) and twice with water, and were incubated with 0.2–0.3 ml/cm² of AuroDye protein stain (Janssen Pharmaceutica, Piscataway, N.J.) at ~22° C. for ≧4 hr. (Tween 20 is a registered trademark of ICI America for a polyethoxyethanol sorbitan; the product was obtained as a 10% aqueous solution packed in glass ampules under nitrogen from Pierce Co., Rockford, Ill. under the name Surfact-Amp 20). AuroDye is a stabilized colloidal gold sol (20 nm), adjusted to approximately pH 3, which stains proteins dark red.

II. CHARACTERIZATION OF THE NATURALLY-OCCURRING HUMAN EI.

(A). Determination of the molecular weight of EI.

The apparent molecular weight of Human EI isolated from the human monocyte-like cell line (U937-EI) was found to be 42,000 by comparing the mobility of the purified Human EI on SDS electrophoresis gels to the mobility of pure proteins of known molecular weight (see Remold-O'Donnell, E., *J. Exp. Med.* 162:2142–2155 (1985); Weber, K., and Osborn, M, *J. Biol. Chem* 244:4406–4412 (1969).) The proteins were detected by gold staining electrophoretic transfers.

(B). Inhibition of Elastinolysis.

Figure 2:
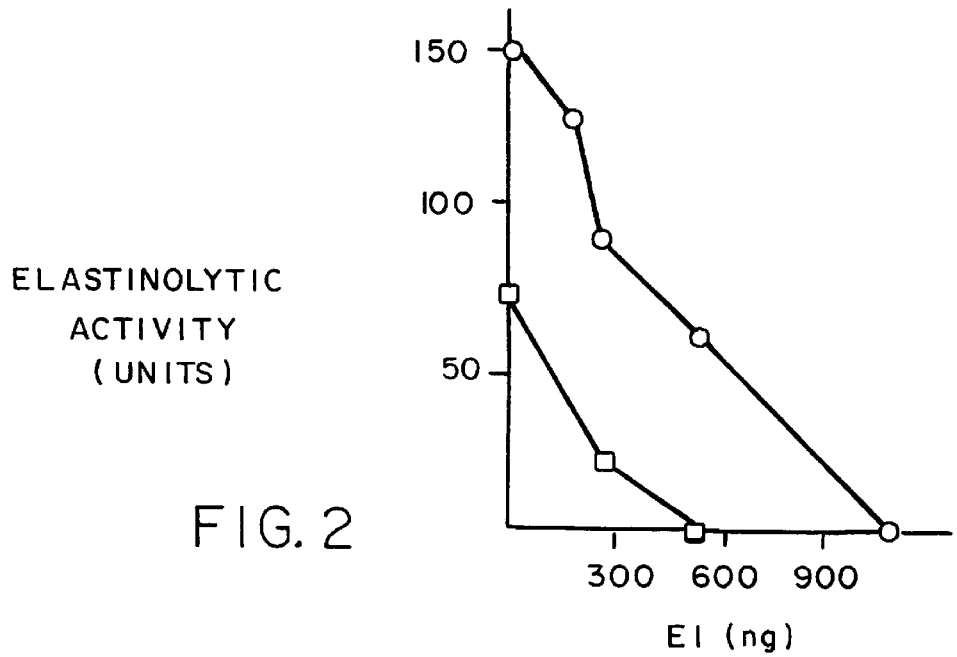
FIG. 2 is a graph showing dose-dependent inhibition of elastinolysis caused by Human EI.

Human EI was assayed for elastinolytic activity by observing the generation of a lytic zone in an elastin-containing agar gel (Senior, R. M. et al., *J. Lab. Clin. Med.* 77:510–6 (1971)). Briefly, varying amounts of Human EI (e.g., pooled, concentrated DEAE fraction) were combined with pancreatic elastase for five minutes at about 22° C., and portions of about 5 ul were placed in wells of about 3 mm diameter in agar gels containing about 0.24% fluorescein-elastin (400 mesh, Elastin Products, Owensville, Mo.) and incubated at 37° C. for 48 hours. The extent of elastinolysis, measured as the diameter of the lysis rings (average of duplicate determinations), was converted to activity units (one unit equaling the activity of one ng elastase) by reference to a standard curve established using known amounts of the Human EI. Activity assays were performed using 75 ng (boxes) and 150 ng (circles) of pancreatic elastase. The presence of Human EI resulted in a dose-dependent inhibition of elastinolysis by elastase, thereby demonstrating that Human EI inhibits the elastinolytic activity of elastase (FIG. 2).

Figure 3:
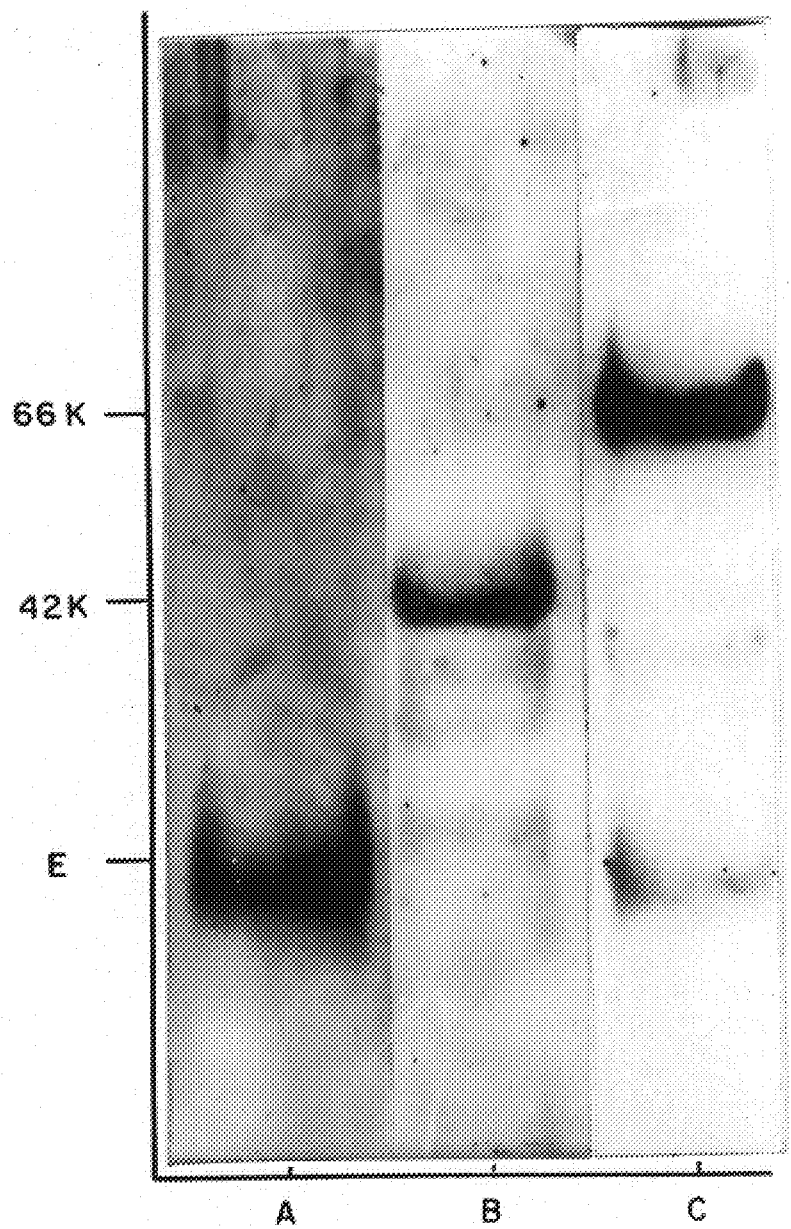
FIG. 3 is a protein-(silver) stained electrophoresis gel which shows Human elastase, Human EI and Human EI complexed with elastase.

To demonstrate that the $M_r$ 42,000 polypeptide is the elastase inhibitor, the DEAE-purified fraction was incubated with nonlabeled elastase and examined on silver-stained SDS-electrophoresis gels (Merril, C. R. et al., *Science* 211:1437–8 (1981)). The SDS gels included three lanes, one for EI, one for elastase and one for a mixture of the EI and elastase. Following co-incubation for 1 min, the $M_r$ 42,000 polypeptide and elastase disappeared concomitant with the formation of a $M_r$ 66,000 elastase-elastase inhibitor complex (FIG. 3). This finding demonstrated that the $M_r$ 42,000 polypeptide was indeed the elastase inhibitor and that the bulk of the purified Human EI had retained complex-forming activity. The results also demonstrated that the reaction of the purified molecule with elastase is rapid (complete at 1 min). The molecular weights of the reactants and the complex clearly suggested that the reaction has 1:1 stoichiometry.

(C). Amino Acid Composition.

An aliquot of lyophilized purified Human EI was hydrolyzed in 6N HCl at 110° C. for 24 hours and its amino acid composition was determined using a Dionex D-500 Analyzer. The Cys/2 content (cysteine plus ½ cystine) was determined as cysteic acid following performic acid oxidation (Hirs, C. H. W., *J. Biol. Chem* 219:611 (1956) and Moore, S., *J. Biol. Chem.* 238:235 (1963)). The amino acid composition of Human EI is presented in FIG. 4, together with the mean composition of 200 purified proteins and that of α1-AT, a known elastase inhibitor found in plasma.

(D). Carbohydrate composition.

The carbohydrate content of pure cytosolic Human EI was determined by methanolysis of a lyophilized sample by gas-liquid chromatography after conversion to the per (trimethylysilyl) derivatives (Reinhold, V. N., *Methods Enzymol* 25:244–249 (1972)). Per molecule of EI, 3.6 residues of xylose (believed to be a contaminant) and 0.5 residue of mannose (average values for two preparations) were detected. Galactose, N-acetylglucosamine, N-acetylgalactosamine, and sialic acid were not detected. Pure Human EI also was treated with the glycosidase PNGase F, an enzyme which cleaves all classes of N-linked carbohydrate units (Tarentino, A. L. et al., *Biochemistry* 24:4665–4671 (1985)). Upon treatment with 140–4200 mU/ml PNGase F, the apparent molecular weight of EI did not change. These results indicate that pure cytosolic Human EI is a non-glycosylated protein. However, as discussed below in reference to the characterization of the recombinant inhibitor, Human EI (like other members of the Ov-serpin family) may exist in two forms: a non-glycosylated cytoplasmic form and an extracellular (possibly glycosylated) form, depending upon the activation state of the cell from which it is isolated.

(E). Amino Acid Sequencing.

Two attempts to determine the amino terminal sequence of pure Human EI were unsuccessful, suggesting that the amino-terminus of the naturally-occurring cytosolic inhibitor is blocked. Accordingly, the Human EI isolated from the monocyte-like cell line was cleaved with trypsin prior to amino acid sequence analysis.

Preparations of Human EI (containing between 40 μg and 80 μg) were heat-treated (85°–90° C. for 8 min) to destroy anti-trypsin activity that may have been present in the Human EI sample. The heat-treated protein was incubated with 0.3%–1% (wt/wt) L-1-tosylamido-2-phenylethylchloromethylketone-treated trypsin (Sigma Chemical Co., St. Louis, Mo.) at pH 8.0 and at 37° C. for 18 hr. A small portion of the trypsin-treated preparation was analyzed by SDS-electrophoresis and gold-staining to insure that hydrolysis of Human EI was complete.

The resulting tryptic peptides were fractionated by chromatography on a $C_{18}$ reverse phase HPLC column with a 2–75% acetonitrile gradient in 0.1% trifluoroacetic acid in water. The $C_{18}$ column contains 300 Angstrom pore size silica having a bonded phase with 5 micron particle size encased in a stainless steel column of 0.46×25 cm (Vydac Division, The Separations Groups, Hesperia, Calif.). Fractions containing the separated peptide peaks were collected (based on absorption at 214 nm) and solvent was removed by lyophilization. The peptide peaks were subjected to amino terminal amino acid sequencing on a gas phase protein sequencer ABI 470A, Applied Biosystems, Foster City, Calif.) equipped with an on-line phenylthiohydantoin HPLC analyzer (ABI 120A On-line PTH analyzer).

Partial amino acid sequences, totalling 137 amino acid residues, were established by sequencing eleven peptides isolated from tryptic digests of human EI (designated Sequence I.D. Numbers 1–11). The sequences of each of these eleven peptides were contained within the deduced sequence of the human gene EI (see Table 1, and Sequence I.D. Number 12).

TABLE 1

Tryptic Peptides of
Human Elastase Inhibitor

| Sequence I.D. Number | Amino Acid Position in Deduced Sequence[a] |
|---|---|
| 1 | 178–186 |
| 2 | 130–137 |
| 3 | 58–68 |
| 4 | 112–128 |
| 5 | 291–299 |
| 6 | 261–274 |
| 7 | 98–110 |
| 8 | 216–237 |
| 9 | 245–254 |
| 10 | 276–289 |
| 11 | 204–213 |

[a]See sequence I.D. No. 12

(F). Existence of Disulfide Bonds.

200 mM of mercaptoethanol did not adversely affect the ability of pure Human EI to form a complex with elastase. These results suggest that Human EI does not contain disulfide bonds and in particular, does not contain disulfide bonds that are essential for complex formation inhibitor-elastase.

(G). Essential Cysteine Residue.

The deduced amino acid sequence has only two cysteine residues, Cys-214 and Cys-344. Addition of the sulfhydryl iodoacetamide (3 mM) to purified Human EI resulted in an almost complete loss of covalent complex forming activity with elastase. Destruction of unreacted iodoacetamide (by the addition of mercaptoethanol) or its removal by dialysis did not restore complex-forming activity to pure Human EI. These results suggest that Human EI contains a cysteine residue that is essential for the formation of the covalent elastase-EI complex.

(H). Reactive Center

The exposed reactive center loop of serpin superfamily molecules is particularly susceptible to variation. In many cases, the $P_1$ residue (i.e., the residue on the N-terminal side of the cleavage site), mirrors the specificity of the target protease and thereby defines inhibitory specificity (Carrell R. and J. Travis, (1985) *TIBS* 20–24). Alignment of the deduced amino acid sequence of Human EI with the amino acid sequences of serpin family members indicated that the $P_1$ residue of human EI was Cys-344, a result consistent with abrogation of Human EI activity by iodoacetamide (described below). However, cysteine is not the "ideal" $P_1$ residue and it has been reported that valine would more specifically mirror the specificity of elastase (McRae B. et al., (1980) *Biochem.* 19:3973–3978). Similar observations in regard to the "ideal" $P_1$ residue previously have been made for α1-antitrypsin (which has methionine as the $P_1$ residue).

These observations suggest that Human EI and α1-antitrypsin are examples of evolution and natural selection independently yielding an elastase inhibitor containing a less than ideal reactive site or that the reactive sites of these inhibitors are ideal, but that the inhibitor functions have been too narrowly defined. Determination of the identity of the $P_1$ residue, together with the protease inhibition studies (described below) suggest that a broader spectrum of proteases are inhibited by Human EI than originally reported in the literature.

(I). Oxidation—Sensitivity

The nature of the human EI reactive center $P_1$–$P'$ residues, Cys-Met, suggests that Human EI can be inactivated by oxidants. Because oxidants are released at inflammatory sites, the ability of Human EI to inhibit proteases in situ likely is limited in temporal terms. Oxidation sensitivity renders elastase inhibitors, such as human elastase inhibitor and α1-antitrypsin, susceptible to regulation in situ. The plasma protein, α1-antitrypsin, which has a methionine residue as its $P_1$ residue has been shown to be inactivated by oxidants in vitro and in vivo (Matheson N. et al., (1979) *Biochem. Biophys. Res. Comm.* 88:402–409; Carp H. et al., (1982) *Proc. Natl. Acad. Sci. USA* 79:2041–2045). These results suggest that a modified Human EI (that is more resistant than the naturally-occurring inhibitor to oxidation in situ) can be prepared using standard procedures to substitute an amino acid that is not susceptible to oxidation and which does not substantially change the inhibitor's conformation (e.g., a conservative substitution) for at least one of the $P_1$–$P'$ residues. The modified Human EI can be assayed for elastinolytic inhibitory activity and for elastase-complex forming activity using the above-described assays. Enhanced resistance to oxidation of the modified Human EI can be determined by assessing the modified inhibitor's sensitivity to known oxidation agents, such as N-chlorosuccinimide, chloramine T, myeloperoxidase plus $H_2O_2$ plus halide ion. In this manner a modified Human EI can be selected which exhibits improved inhibitory activity, complex forming activity and/or oxidation resistance with respect to the naturally occurring Human EI. Alternatively, a modified Human EI having increased sensitivity to oxidation in situ can be prepared by substituting an amino acid that is more susceptible to oxidation for at least one of the cysteine or methionine residues at the active site. Such modified HEIs may be useful when it is desirable, for example, to decrease the half-life of administered Human EI.

(J). Demonstration of EI in Monocytes, Macrophages and Neutrophils.

Figure 5:
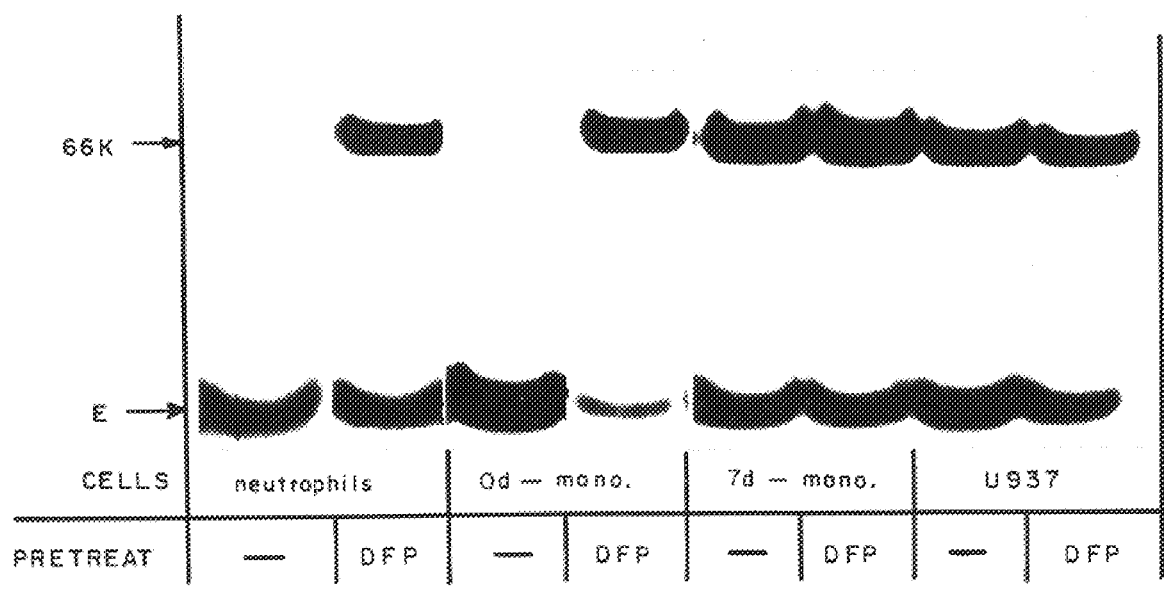
FIG. 5 is an autoradiograph showing the presence of Human EI in monocytes, neutrophils and U937 cells.

Human EI was detected in lysates of human monocytes that had matured in culture and in the monocyte-like cell line U937-EI using the $^{125}$I-elastase complex forming assay. Human EI was not detected in freshly isolated human monocytes or neutrophils. When the latter cells were incubated with the active site reagent diisopropyl fluorophosphate (DFP), lysed in the presence of DFP, and dialyzed to remove excess DFP from lysates, Human EI activity was readily detected in fresh monocytes as well as neutrophils (FIG. 5), demonstrating that Human EI is expressed in these cells. Human EI activity also was detected in lysates of pulmonary macrophages obtained by broncholavage of healthy nonsmoker volunteers.

III. CLONING HUMAN EI.

(A). RNA Isolation and Analysis.

Total mRNA was isolated from U937-EI cells and reverse-transcribed to cDNA using conventional procedures. Briefly, total RNA from both U937-EI cells and CEM human lymphoblastoid cells was isolated by cesium chloride centrifugation from guanidinium thiocyanate and mercaptoethanol-lysed cells (Chirgwin et al., *Biochemistry*, 1979, 18:5294–5299). Poly(A)$^+$ RNA was isolated by oligo (dT) chromatography (Aviv and Leder, *PNAS*, 1972, 69:1408–1412). RNA analysis was performed to confirm the presence of the mRNA for human elastase inhibitor in the monocyte-like cell line U937 and its apparent absence in the lymphoblastoid cell line CEM. RNA for Northern analysis was size-fractionated by formaldehyde/agarose electrophoresis (Maniatis et al., *Molecular Cloning*. Cold Spring Harbor Laboratory, 1982) with RNA sizing markers (Gibco, BRL, Grand Island N.Y. 14072) in a parallel lane, and transferred to nitrocellulose. An insert of cDNA clone U-10

(described below) labeled with $^{32}$P-dCTP by random primed labeling served as the probe (K. Moreman, *PNAS*, 1989, 86:5276–5280; Royer-Pokora et al., *Nature*, 1986, 332:32–38).

Figure 6:
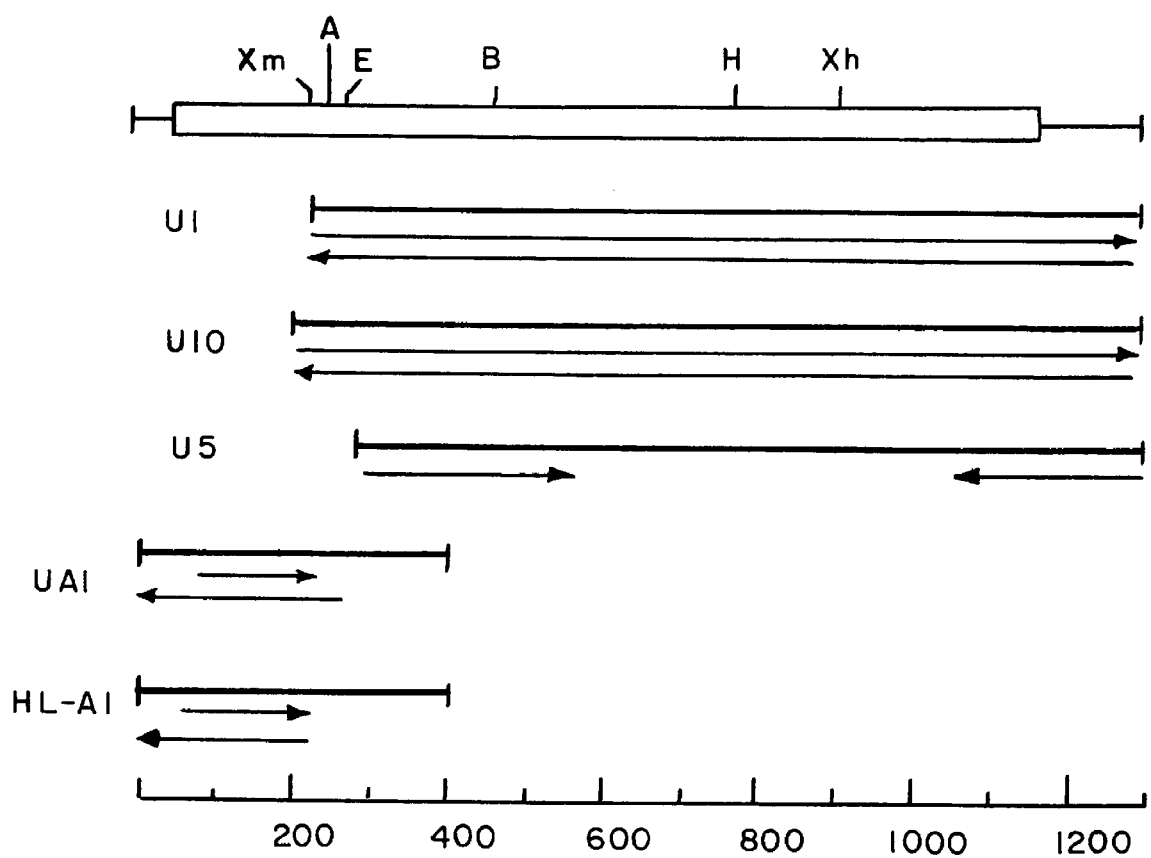
FIG. 6 is a schematic diagram of restriction sites and the cloning strategy of human EI cDNA. The upper section represents the 1316 bp composite sequence with the open box indicating the protein coding region and with restriction sites indicated. Inserts of clones U1 (residues 241–1316), U5 (292–1316) and U10 (216–1316) are shown, as are the amplification products UA1 and HL-A1 (each 1–414). Lines with directional arrows indicate regions sequenced by overlapping reactions.

Northern analysis with this probe revealed hybridization with the probe for RNA isolated from the monocyte-like cell line U937 but no detectable hybridization for mRNA isolated from the lymphoblastoid cell line CEM. The U937 cell mRNA species had sizes of 2.6 kb, 1.9 kb and 1.5 kb. The 1.5 kb fragment had a size corresponding approximately to the size of the composite cDNA sequence (Sequence I.D. number 12). The strategy for obtaining Sequence I.D. number 12 is described below and is shown in FIG. 6.

(B). Preparation and Analysis of DNA.

cDNA corresponding to poly(A)$^+$ RNA isolated from U937-EI cells was synthesized as described by Moreman, *PNAS*, 1989, supra). Moreman provides a detailed procedure for the mixed oligonucleotide primed amplification of cDNA ("MOPAC"). The MOPAC method is divided into three principle steps: (1) cDNA synthesis, (2) designing of oligonucleotide primers, and (3) amplification of cDNA using the polymerase chain reaction ("PCR").

Synthesis of the Human EI cDNA using the MOPAC procedure was performed using a 100 ul reaction volume containing 200 units of murine leukemia virus reverse transcriptase (Gibco, BRL), enzyme buffer (Gibco, BRL), 5 ug of U937 cell poly(A)$^+$ RNA, 40 units of RNasin (Promega), 1 mM of each dNTP, and 15 ug/ml random hexanucleotide primers (Promega) at 37° C. for 1.5 hours. The mixture was extracted with phenol/chloroform/isoamyl alcohol (25:24:1) and desalted on a Sephadex G-50 column (Pharmacia, Piscataway, N.J. 08855) equilibrated in 10 mM Tris-HCl buffer, pH 8.0 containing 100 mM KCl . Following extraction, the mixture was designated the "cDNA synthesis product" and amplified as described below.

(C). Mixed Oligonucleotide Primed Amplification of cDNA ("MOPAC").

MOPAC amplification requires two or more oligonucleotide primers encoding non-contiguous peptide sequences with known relative locations. In order to identify the relative locations of peptide sequence I.D. Numbers 1 through 11, a computer program was initially used to identify regions of sequence homology between the monocyte peptides and known Serpin proteins. Analysis of the monocyte peptides was important for performance of the MOPAC procedure.

The program LFASTA (provided by Dr. William Pearson, Charlottesville, Va.) was used to search for regions of partial sequence homology between peptide sequence I.D. Numbers 1 through 11 and known Serpin proteins. The program is based upon the method of Pearson and Lipman (*PNAS*, 1989, 85:5276–5280). The program allowed some of peptide Sequence I.D. Numbers 1 through 11 to be tentatively located relative to one another by first identifying the relative positions of corresponding peptides in known Serpin proteins.

Oligonucleotide sense primers were designated corresponding to peptide Sequence I.D. Numbers 3 and 4, and antisense primers were designated corresponding to peptide Sequence I.D. Number 8 and contiguous Sequence I.D. Numbers 5 and 10. Primers were synthesized by the phosphoramidite method on an Applied Biosystems Model 380B synthesizer (Foster City, Calif. 94404). Codon degeneracy was taken into account in the design of oligonucleotide primers by using the most frequently occurring codon for a particular amino acid, using mixtures of nucleotide triphosphates, or by deoxyinosine substitution as described by Moreman (*PNAS*, 1989, 86:5276–5280).

Amplification of U937 cell cDNA was performed using pairs of the above-described primers. The cDNA synthesis product from poly(A)$^+$ RNA (5 ul) was amplified according to standard procedures (K. Moreman, *PNAS*, 1989, 86:5276–5280) in 100 ul containing 10 mM Tris-HCl buffer, pH 8.3, 50 mM KCl, 1.5 mM MgCl$_2$, 0.01% gelatin, 200 uM of each dNTP, and 0.5 uM of the above-disclosed primers. Following the addition of 2.5 units of *Thermus aquaticus* (Taq) polymerase (Perkin-Elmer/Cetus Inc., Norwalk, Conn. 06859) with 100 ul of mineral oil overlay, the amplification mixture was incubated in a DNA Thermal Cycler (Perkin-Elmer Cetus, Inc.) for 30 cycles, each cycle comprising incubation for 1 min. at 92° C., for 2 min. at 50° C., and for 3 min. at 72° C.

The MOPAC-amplified cDNAs were resolved by electrophoresis on 1% low melt agarose containing ethidium bromide at a concentration between 0.5 and 1 ug/ml. Electrophoresis revealed that amplification of U937 cell cDNA with pairs of the above-disclosed MOPAC primers resulted in single dominant products which were readily detected by ethidium bromide staining. The amplified cDNA fragments had sizes consistent with the LFASTA peptide localization, i.e., one product contained 510 bp (the product of primers corresponding to peptides Sequence I.D. Numbers 3 and 8); another product contained 340 bp (the product of primers corresponding to peptides Sequence I.D. Numbers 4 and 8); one product contained 720 bp (the product of primers corresponding to peptide Sequence I.D. Number 3 and combined peptide Sequence I.D. Numbers 10 and 5); and one product contained 550 bp (the product of primers corresponding to peptide Sequence I.D. Numbers 4 and combined peptide Sequence I.D. Numbers 10 and 5).

(D). Preparation of Probes for Screening cDNA Libraries.

The amplified cDNA fragment containing 550 bp, described above, was subsequently labeled with $^{32}$P-dCTP by random priming (Feinberg and Vogelstein, *Anal. Biochem*, 1983, 132: 6–13). This probe was used to screen 700,000 clones of a U937 cDNA library. The screening procedure is described below.

(E). Description of cDNA Libraries.

In general, a cDNA library is prepared by inserting each cDNA molecule into a vector, such as for example into the phage λgt11 or λ-ZAP II (Uni-ZAP, Stratagene, La Jolla, Calif. 92037). Alternatively, a human monocyte or monocyte-like cDNA library in a vector such as λgt11 may be purchased. The vectors are not limited to those capable of replication in bacterial systems but also include vectors capable of replication in mammalian, insect or other types of cell lines.

A cDNA library in a bacterial vector is generally expressed in *E. coli* and grown up to ~10$^5$ *E. coli* plaques, each plaque derived from one infected bacterium. The plaques then are screened to identify those plaques containing the λgt11 phage which includes the monocyte cDNA of interest. The detection probe for screening the *E. coli* plaques can be, for example, an oligonucleotide encoding a portion of Human EI or an antibody to Human EI. The appropriate oligonucleotide probes disclosed herein are based upon the Human EI sequencing data presented above. The probes were prepared according to the MOPAC method. The MOPAC method could be utilized because of the availability of (1) sequences of the tryptic peptides of pure human EI, (2) a program for comparing protein sequence homology and (3) our knowledge that Human EI is a member of the Serpin family of proteins.

Alternatively, appropriate screening antibodies can be prepared by conventional immunization techniques using, for example, purified Human EI as the immunogen. The preparation in mice and rabbits of antibodies to naturally-occurring and recombinant Human EI is described below. Peptides also can be synthesized according to standard procedures using the known sequences of EI peptides and the synthetic peptides can be used as immunogens, alone or in combination with the naturally occurring or recombinant Human EI, to generate anti-Human EI antibodies.

Once the plaque of interest is identified, the cDNA from the expression vector in that plague can be isolated and the genomic complement to the cDNA for Human EI can be isolated, all according to conventional techniques. In the embodiment described herein, three independent cDNA libraries were used to define the cDNA for human elastase inhibitor.

(1). λ-ZAP II Library:

Preparation of this library was performed by Stratagene (La Jolla, Calif.) using the U937 cell cDNA described above (corresponding to poly(A) selected RNA) by unidirectional insertion into a λ-ZAP II vector (Uni-ZAP, Stratagene). The λ-ZAP II Library is commercially available from Stratagene. The amplified cDNA product (generated by primers corresponding to peptide Sequence I.D. number 3 and combined peptide Sequence I.D. numbers 5 and 10 and containing 550 bp) was used as a probe to screen 700,000 clones of the λ-ZAP II Library. A total of fifteen positive clones by duplicate screening were selected for further analysis. Positive plaques were plaque purified according to standard procedures (see e.g., Maniatis, et al. supra).

Phage λ-ZAP II contains the plasmid pBluescript SK into which the mammalian cDNA is inserted. The use of the phage is advantageous in that the pBluescript plasmids can be used directly for DNA sequencing. Accordingly, the pBluescript plasmids containing all or part of the putative elastase inhibitor cDNA were obtained by in vivo excision as described by Strategene in the product literature which accompanied the λ-ZAP II (Uni-ZAP) vector.

The cloned DNA inserts were subjected to electrophoresis on low melt agarose gels. Of the selected clones, three clones having inserts greater than approximately 0.8 kb were partially or completely sequenced. The cDNA inserts contained in these clones were designated U-1 (complete sequence); U-5 (partial sequence), and U-10 (complete sequence). (See FIG. 6) However, none of the clones, alone or together, yielded the sequence of a complete open reading frame for the elastase inhibitor gene. Accordingly, the DNA segment corresponding to the missing 5' region of the elastase inhibitor gene was isolated from two additional independent cDNA libraries: the λ-gt11 and λ-gt10 libraries.

(2). λ-gt11 Library:

A U937 cell cDNA library in λ-gt11 was purchased from Clontech Laboratories, Palo Alto, Calif. 94303.

(3). λ-gt10 Library:

A λ-gt10 library from HL60 promyelocytic cells (Collins et al., *PNAS*, 1978, 75:2458) induced toward granulocytic differentiation (Newburger et al., *J. Biol. Chem.*, 1984, 259:3771) by dimethylformamide treatment (Royer-Pokora et al., *Nature*, 1986, 332:32–38; Parkos et al., *PNAS*, 1988, 85:3319) was provided by Dr. Stuart Orkin, Children's Hospital, Boston, Mass.

(F). Generation of the 5' Region of the human elastase inhibitor gene by Amplification of Library cDNAs.

To complete the sequence for the elastase inhibitor cDNA, segments corresponding to the missing 5'-region were amplified using total DNA from two independent cDNA libraries as template, a flanking vector sequence as the sense primer, and the antisense primer (described below) was to a portion of clone U-10.

Specifically, λ-gt11 and λ-gt10 libraries were separately used as sources of DNA for direct amplification using a modified standard polymerase chain reaction (PCR) amplification procedure as described by Rosenberg et al. (*Biotechniques*, 1991, 10:53–54). The DNA was pelleted by centrifugation. An amount of DNA corresponding to $10^5$–$10^7$ plaque forming units (pfu) was denatured and was incubated in 100 ul of a standard reaction mixture (Rosenberg et al, supra).

The antisense primer was an 18-mer (18 nucleotides) corresponding to clone U-10 residues 590–607. For DNA isolated from the λ-gt11 library, the sense primer was a 24-mer (product #1218, New England Biolabs, Beverly, Mass.) corresponding to the λ-gt11 vector flanking sequence in the forward direction. For DNA isolated from the λ-gt10 library, the sense primer (product #1231, New England Biolabs) was a 21-mer corresponding to the λ-gt10 vector flanking sequence in the forward direction.

The amplification reaction mixture was overlaid with 100 ul mineral oil and allowed to proceed for 40 cycles, each cycle comprising 1 min. at 92° C., 2 min. at 55° C., and 3 min. at 72° C. Following gel electrophoresis, the amplification product having approximately 800 bp was excised from the gel and used as a template for a second amplification reaction, using the buffers and reaction conditions described above. The predominant product of the second amplification reaction, which was approximately 800 bp, was gel-purified and used as a template in a third amplification reaction.

The third amplification differed from the prior amplification reactions in that (1) the third amplification consisted of 6–8 parallel 100 ul reactions and (2) substituted an 18-mer antisense primer corresponding to U-10 residues 182–199 for the antisense primer used originally in the first and second amplification reactions.

An amplified product (UA1) containing approximately 460 bp was generated using DNA isolated from the λ-gt11 library. Similarly, an amplified product (HL-A1) containing approximately 460 bp was generated using DNA isolated from the λ-gt10 library (See FIG. 6). These products were purified by gel electrophoresis, extracted with phenol/chloroform, and ethanol precipitated in preparation for DNA sequencing. The inserts of the isolated clones in the plasmid pBluescript and the double stranded amplified DNA products were sequenced by the dideoxy chain termination/extension reaction (Sanger, *PNAS*, 1977, 74:5463–5467) using Sequenase reagents (U.S. Biochemicals), and vector-specific primers and 18-mer primers based on the elastase inhibitor sequence as it became known.

(G). Nucleotide Sequence of Human Elastase Inhibitor.

The inserts of the clones and extension products were sequenced by the strategy outlined in FIG. 6. The open box in the upper part of FIG. 6 represents the protein coding region. The scale at the bottom indicates the nucleotide positions. Not all overlapping segments were sequenced. However, all overlapping segments which were sequenced were identical, except at base 1298 to be explained later in this section. The lengths of clones U-10, U-1 and U-5 and amplification products UA1 and HL-A1, are indicated (FIG. 6). The regions which were sequenced by overlapping reactions, are indicated by solid lines with directional arrows (FIG. 6). The composite sequence (Sequence I.D. Number 12) is 1316 nucleotides long and includes a single open reading frame and a poly(A) tail containing at least 18 residues. The open reading frame begins at position 49 with the first methionine codon, part of the sequence ACCATGG, the proposed optimal sequence for initiation by eukaryotic ribosomes (Kozak, *Cell*, 1986, 44:283). [A truncated cDNA (Sequence I.D. Number 13) containing nucleotides 37–1188 of Sequence I.D. Number 12, i.e., twelve 5' untranslated Human EI nucleotides and the open reading frame except that TAA replaces TAG as the stop codon and lacking the 3' untranslated Human EI nucleotides, was used in the Baculovirus/insect expression system to prepare large quantities of recombinant Human EI.]

The reading frame of Human EI terminates with a stop codon at position 1186 to 1188. The open reading frame is followed by a 3' untranslated region of 109–113 nucleotides including a single polyadenylation signal, AATAAA, beginning at residue 1277, and the poly(A) tail. The only sequence difference observed between the clones is present at residue 1298. This residue is C in clones U-1 and U-5 and is A in clone U-10 (FIG. 6).

(H). Derived Amino Acid Sequence.

The open reading frame encodes a polypeptide of 379 amino acids with a molecular weight of 42,741 and the composition of $Asn_{23}$ $Asp_{18}$ $Gln_{11}$ $Glu_{30}$ $His_7$ $Lys_{29}$ $Arg_{14}$ $Ala_{30}$ $Cys_2$ $Gly_{20}$ $Tyr_{10}$ $Val_{18}$ $Ile_{19}$ $Leu_{41}$ $Phe_{27}$ $Met_{12}$ $Trp_3$ $Pro_{12}$ $Ser_{31}$ $Thr_{22}$. The amino acid sequence of the open reading frame for the human elastase inhibitor is shown in Sequence I.D. Numbers 12 and 13. The deduced sequence includes all of the tryptic peptides shown in Table 1. The encoded polypeptide sequence is unique. A search of the complete data base at the National Biomedical Research Foundation, Washington, D.C.(September, 1991) using the FASTA program (Pearson and Lipman, *PNAS*. 1988, 85: 2442–2448) did not reveal any proteins having identical or nearly identical sequence homology.

Several features of the derived polypeptide sequence confirm the composite cDNA as encoding human EI. The length of the derived polypeptide sequence, 379, is quite close to the length of approximately 360 amino acids determined by measuring the electrophoretic mobility of pure human EI. Significantly, the derived molecular weight of 42,686 is quite close to the approximate molecular weight of about 42,000 determined on the purified protein. The derived amino acid composition is similar, although not identical, to the amino acid composition determined for purified human EI (FIG. 4).

More importantly, the sequences of the eleven tryptic peptides prepared from isolated human EI (Sequence I.D. Numbers 1 through 11) are contained within the 379 residue deduced sequence. Functional data obtained using Human EI indicated that Human EI is a member of the Serpin family of proteins. In addition, a comparison of the derived amino acid sequence for Human EI (using the above-noted databank sequences) revealed strong partial identity between Human EI and several previously described proteins, each of which is a member of the Serpin family. For polypeptides of this length, identity greater than 25% indicates that the two molecules are very likely genuinely related (R. F. Doolittle, *Of URFS and ORFS, A Primer on How to Analyze Derived Amino Acid Sequences*, University Science Books, Mill Valley, Calif., 1986). The four most closely related Serpin sequences detected in the search of the National Biomedical Research Foundation data base (September 1991) are: plasminogen activator-2 (50.2% identity); gene Y (42.7% identity); ovalbumin (39.8% identity); and antithrombin III (39.3% identity). The treatment of pure human EI with iodoacetamide abrogated its ability to form a complex with elastase and indicated that human EI has an essential cysteine residue. Use of the program FASTA to align the Human EI derived amino acid sequence with data bank Serpin sequences indicated that the active site residue in the derived sequence is cysteine at position 344.

(I). Southern Analysis.

Total genomic DNA from U937-EI cells was isolated, digested with the restriction enzymes EcoR1 and Hind3 and subjected to Southern analysis using a probe prepared from the U-10 insert as described above. Southern analysis (not shown) identified single hybridizing bands of 4.5 and 6.5 bp, suggesting that the human elastase inhibitor is encoded in humans by a single copy gene.

(J). Restriction Enzyme Analysis

Computer analysis of the composite cDNA sequence identified unique sites for cleavage by restriction enzymes, some of which are as follows: XmnI at residue 242, AlwNI at residue 264, EcoRV at residue 276, BspEI at residue 480, HincII at residue 795, XhoII at residue 930 (FIG. 6).

The first three restriction enzyme sites are located in the overlap region; residues 216–414 are present in the amplified DNA products and in isolated clones U-1 and U-10. The enzymes AlwN, EcoRV or XmnI (all of which are available commercially, e.g., New England Biolabs, Beverly, Mass.) can be used to generate a composite clone by restriction cleavage, isolation and ligation of the DNA fragments.

(K). Expression of Recombinant Human Elastase Inhibitor

The absence of glycosylation and disulfide bonds in the cytosolic Human EI suggested that most expression systems (e.g., *E. Coli*, yeast, Baculovirus and COS cells) would be suitable for expressing Human EI. Human EI was expressed as an insoluble protein in *E. Coli* and as a soluble cytoplasmic protein and a soluble released protein in a Baculoviral expression system (described in detail below).

Recombinant Human EI was expressed in *E. Coli* using the vector pQE6, isopropylthiogalactoside to induce expression, and ultrasonication to lyse bacteria. Analysis of the Human EI was by SDS/PAGE and Western blots. The expressed protein had a molecular weight corresponding to that of the naturally-occurring cytosolic Human EI and was reactive with antibodies to the Human EI antigen. The protein expressed in the *E. Coli* expression system was approximately 99% insoluble and was not studied further. Instead, Human EI (Sequence I.D. Number 13) was expressed in a Baculovirus/insect cell system.

IV. HUMAN ELASTASE INHIBITOR EXPRESSION IN A BACULOVIRUS EXPRESSION SYSTEM.

The Baculovirus/insect cell system has produced a number of recombinant human proteins which have the conformation of their naturally-occurring counterparts (reviewed in Smith G. et al., (1983) J. Virol 46:584–593; O'Reilly D. et al., Baculovirus expression vectors. W. H. Freeman & Co., New York 1992). The procedures for expressing Human EI in this expression system are described in detail below.

(A). Materials and Methods (1). Preparation of a Full Length cDNA and Generation of Recombinant Transfer Vector and Baculovirus—To construct a full-length HEI cDNA, UA1, the 5' segment from the above-described cDNA sequencing study (See also, Remold-O'Donnell, E. et al. (1992) *Proc. Natl. Acad. Sci. USA* 89:5635–5639) was amplified using (Sequence I.D. Number 14) and the complement of nucleotides 397–411 (see Sequence I.D. Number 12) as primers. The DNA was digested with EcoRI and AlwNI, purified, and subcloned into the corresponding sites of incomplete HEI clone pBluescript U-10 as described above. Restriction digestion and DNA sequencing verified that the resultant plasmid, pBluHEI-30, contained HEI cDNA nucleotides 37–1316.

A 3' BglII site was introduced by amplifying pBluHEI-30 with the above 5'-primer and 5'GGAGATCTAAGGGGAA-GAAAATCTCCC (Sequence I.D. Number 15). The DNA was digested with EcoRI and BglII, purified, and subcloned into the corresponding sites of the transfer vector pVL1393 (Luckow, V. A. and M. D. Summers (1989) *Virology* 170:31–39; O'Reilly, D. R. et al. (1992) *In Baculovirus Expression Vectors* W. H. Freeman and Company, New York.) (PharMingen, San Diego, Calif.). Dideoxy sequencing (Sanger, F. et al. (1977) *Proc. Natl. Acad. Sci. USA* 74:5463–5467) revealed a three nucleotide mutation, which was corrected by replacing nucleotides 37–1146 with the EcoRI-Bsu36I fragment from pBluHEI-30. The resultant plasmid, pVL1393-HEI, was verified by sequencing; it contained nucleotides 37–1188 (Sequence I.D. Number 13), i.e., twelve 5' untranslated HEI nucleotides and the open reading frame with TAA replacing TAG as stop codon; it lacked the 3' untranslated HEI nucleotides.

To generate recombinant baculovirus by homologous recombination, monolayers of *Spodoptera frugiperda* (Sf9) cells (provided by Dr. Jaime Lazarte, CBR Laboratories, Boston, Mass., from stock obtained from the American Type Culture Collection, Rockville, Md.) were cotransfected by the calcium phosphate method (reagents from PharMingen) with transfer vector pVL1393-HEI and linearized baculovirus DNA, which contained a lethal deletion (BaculoGold DNA, PharMingen). The homologous recombination method is described in O'Reilly, D. R. et al. (1992) *In Baculovirus Expression Vectors* W. H. Freeman and Company, New York.). Occlusion-negative plaques were retrieved after 2 weeks; no wild-type plaques were observed. Stocks of the recombinant virus, AcNPV-HEI, and wild-type virus (AcNPV) (PharMingen) were prepared by infecting Sf9 monolayer cultures grown (at 27° C.) in Grace's Insect Medium (Gibco/BRL, Gaithersburg, Md.), with 10% heat-inactivated (56° C. for 40 min) fetal calf serum (Flow Labs. Inc., McLean, Va.) and harvesting medium after 10–14 days.

(2). Insect Cells and Viral Infection—Sf9 cells were grown in spinner flasks at 27° C. in Ex-Cell™ 400 (a serum-free culture media for insect cells) (JRH Biosciences, Lenexa, Kans.). Cells were pelleted for infection and suspended to $10^7$/ml in viral stock (in 10% FCS as described above), incubated at 27° C. for 1 h, then diluted to $3 \times 10^5$ cells/ml with Ex-Cell 400 medium (final FCS content= 0.3%), transferred to spinner flasks and cultured at 27° C. for 1 to 8 days. Where noted, serum-free viral stock prepared by infecting Sf9 monolayer cultures grown in Ex-Cell 400 was used to infect Sf9 cells as described above.

(3). Cell Harvest and Fractionation—Infected Sf9 cultures were centrifuged to produce a cell pellet and a cell-free media. The cell-free media and cell pellets were stored at 4° C. and −20° C., respectively, until assay. Cells were lysed by adding 1 ml per $4 \times 10^6$ cells of 0.5% NP40 (BDH Chemicals, Poole, England) in PBS. The mixture was pipetted and centrifuged in an SS34 rotor (Sorvall Instruments, Wilmington, Del.) at 13,000 rpm for 13 min at 4° C. to yield the NP40-soluble and NP40-insoluble fractions.

(4). Human Cells—The human monocyte-like cell line U937 was grown, harvested and lysed as described above. Where indicated, U937 cell HEI was purified to homogeneity as described above or was partially purified by Thiopropyl-Sepharose chromatography.

(5). Anti-HEI Antiserum—A New Zealand female rabbit was immunized by subcutaneous injection of 14 μg pure U937 cell HEI, which had been denatured with 0.1% SDS at 100° C. for 2 min and emulsified with complete Freund's adjuvant. Two and 4 weeks later, the rabbit was injected subcutaneously with 7 μg similarly denatured HEI emulsified in incomplete Freund's adjuvant. Serum was collected 1–4 weeks thereafter.

(6). Goat Anti-Rabbit IqG—Purified IgG of goat anti-rabbit IgG (Cappel, Durham, N.C.) (200 μg in 200 μl ) in 10 mM sodium phosphate buffer, pH 7.2, 200 mM NaCl (iodination buffer) was reacted with 2.4 mCi of $Na^{125}I$ in two glass tubes coated with 50 μg each of Iodogen (1,3,4, 6-tetrachloro-3α, 6α-diphenylchloroglycouril) (Fraker, P. J. and J. C. Speck, Jr. (1978) *Biochem. Biophys. Res. Commun.* 80:849–857) (Pierce Chemicals, Rockford, Ill.) for 40 min at ~22° C. A 300–400 μl AG 1-X8 chloride column was pretreated with 500 μg bovine albumin and washed with iodination buffer; the reaction mixture combined with 10 μg tyrosine was applied followed by 1 ml iodination buffer. The nonadherent fraction, which contained the product (~3 μCi/μg), was combined with an equal volume of PBS containing 1% milk solids and stored in aliquots at −20° C.

(7). SDS/PAGE—Culture media and NP-40 soluble fractions were heated for 2 min at 100° C. with 0.1 volume of 5% SDS, 25% mercaptoethanol. The NP-40 insoluble fraction was pipetted at 100° C. with 1 ml per $4 \times 10^6$ starting cells of 2% SDS, 4% mercaptoethanol in 60 mM Tris-glycine buffer, pH 6.8. Samples were separated on 1.5 mm 9% polyacrylamide SDS gels as described (Remold-O'Donnell, E. (1985) *J. Exp. Med.* 162:2142–2155; Laemmli, U. K. (1970) *Nature* 227:680–685), and mobility was determined relative to myosin, 200,000; β-galactosidase, 130,000; phosphorylase a, 94,000; bovine albumin; 68,000, creatine kinase, 40,000 and carbonic anhydrase, 29,000. Pure proteins were also fractionated by SDS/PAGE and transferred electrophoretically to polyvinylidine difluoride (PVDF) membrane (Millipore, Bedford, Mass.) for "gold staining" with Aurodye protein stain (Amersham, Arlington Heights, Ill.) as described (Remold-O'Donnell, E. et al. (1989) *J. Exp. Med.* 169:1071–1086).

(8). Western Blot—Polypeptides in SDS gels were transferred to 0.2μ nitro-cellulose (Schleicher and Schuell, Keene, N.H.) at 80 mAmps for 16 h at ~22° C. The membrane was treated at ~22° C. for 30 min with PBS containing 0.5% Tween-20 and 20% milk solids (PBS/Tween/20% milk), washed 5 times with PBS/Tween, treated for 60 min with rabbit anti-HEI antiserum (diluted 1 to 1000 in PBS/Tween/0.1% milk), washed 5 times with PBS/Tween, incubated for 90 min with 0.27 μg/ml of $^{125}I$-labeled goat anti-rabbit IgG in PBS/Tween/0.1% milk containing 150 mM NaI. After 3 washes with the latter solution and 2 washes with PBS/Tween, the Western blot membrane was analyzed by autoradiography and/or "phosphor-imaging".

(9). Quantitation of HEI Molecules—Recombinant HEI protein was quantified by scanning and integrating the 42 kD bands in duplicate wet Coomassie blue stained SDS gels on an Ultrascan IX densitometer (LKB Instruments, Rockville, Md.). Densitometry values were converted to arbitrary linear "protein units" by comparison with 30, 60, 100-μl aliquots of a single recombinant HEI-containing media analyzed in parallel as a calibration curve. To quantify recombinant HEI in Western blots, the $^{125}I$ pattern was captured by "phosphor-imaging" using the Model GS-250 Molecular Imager (BioRad Laboratories, Richmond, Calif.) and the captured radioactivity in the HEI bands was converted to arbitrary linear "antigenic units" using an internal calibration curve as described above.

(10). PNGase F Treatment—Recombinant HEI (rHEI) in media (containing 0.3% serum) collected on day 7 from Sf9 cells infected with AcNPV-HEI was partially purified by dialysis against 20 mM Tris HCl, pH 7.4, 2 mM EDTA, 2 mM dithiothreitol, absorption onto Q-Sepharose FF (Pharmacia/LKB) at ~22° C. and elution with 50 mM NaCl in the same buffer. Approximately 100 ng rHEI and 100 ng of the glycoprotein α1-AT (Chemicon, Temecula, Calif.), were denatured at 100° C. for 1 min in 0.5% SDS, 2 mM mercaptoethanol. The proteins were incubated with PNGase F (peptide:N-glycosidase F) from *Flavobacterium meningosepticum* (Genzyme Corp., Cambridge, Mass.) for 3 h at 37° C. in 30 mM Tris HCl, pH 8.6, 1% NP-40, 0.14% SDS, 1 mM diisopropyl fluorophosphate (DFP), 10 mM 1,10 phenanthroline and analyzed by SDS/PAGE and "gold staining".

(11). Formation of a Complex with $^{125}$I-Elastase and Two-Dimensional Electrophoresis—U937 cell lysate and Sf9 cell media containing recombinant HEI were incubated for 5 min at 37° C. with $^{125}$I-porcine pancreatic elastase as described (See also Remold-O'Donnell, E. (1985) *J. Exp. Med.* 162:2142–2155; Remold-O'Donnell, E. et al. (1989) *J. Exp. Med.* 169:1071–1086). Excess elastase was inactivated with 2 mM DFP for 3 min at 37° C. Isoelectric focusing in polyacrylamide tube gels, the first dimension separation, and SDS/PAGE, the second dimension, were performed on samples in 9.5M urea, 60 mM dithiothreitol using a modified method (O'Farrell, P. H. (1975) *J. Biol. Chem.* 250:4007–4021; Linck, R. W. et al. (1982) *Cell Motility (Suppl.)* 1:127–132). The ampholytes (Ampholine, Pharmacia/LKB) were 4% of range pH 5–8, 0.4% of range 4–6, and 0.6% of pH 3–10. The pH gradient, measured after elution with water of slices from two parallel gels, was nearly linear.

(12). Proteases and Protease Inhibitors—Human neutrophil elastase (875 units/mg) (Twumasi, D. Y. and I. E. Liener (1977) *J. Biol. Chem.* 252:1917–1926; Andersson K. K. et al. (1980) *J. Chrom* 192:236–239) isolated from purulent sputum and porcine pancreatic elastase (135 units/mg) were from Elastin Products, Owensville, Mo.; human neutrophil cathepsin G isolated from human white blood cells was from Athens Research and Technology, Athens, Ga.; human urokinase (μ-plasminogen activator) was a gift of Serono Laboratories. Stock solutions of these were prepared in PBS at 1 mg/ml and stored in aliquots at −20° C. Proteinase-3 was purified from an extract of neutrophil granules using Matrex Gel Orange chromatography followed by cation exchange chromatography on Bio-Rex 70 as described (Janoff, A. (1985) *Ann. Rev. Med.* 36:2207–2216) and was stored at 0.3 mg/ml in PBS at 4° C. The purity of proteinase-3 was verified by SDS/PAGE followed by silver staining; purity was also ascertained by discontinuous nondenaturing gel electrophoresis (J. M. Thomas and M. E. Hodes, *Anal. Biochem.* 118.:194–196, 1981).

Recombinant plasminogen activator inhibitor-2 (PAI-2) was from American Diagnostica Inc, Greenwich, Conn. Recombinant HEI for activity assays was 6 day serum-free media of AcNPV-HEI infected Sf9 cells that had been stored in aliquots at −20° C. (with or without addition of 2 mM dithiothreitol) and additional 150 mM NaCl; the control fraction was a similarly-treated 6 day media of AcNPV-infected Sf9 cells.

(13). Peptidase Assays—The activity of human neutrophil elastase (HNE) was assayed with 0.4 mM N-methoxysuccinyl-Ala-Ala-Pro-Val-p-nitroanilide in 20 mM Tris HCl buffer, pH 7.4, 150 mM NaCl, 0.1% polyethyleneglycol (mol. wt. 8000) (Sigma Chemical Co., St. Louis, Mo.) and 2 mM dithiothreitol at 37° C. and the change in absorbance at $OD_{410nm}$ was measured (Remold-O'Donnell, E. et al. (1989) *J. Exp. Med.* 169:1071–1086). Porcine pancreatic elastase (PPE) activity was assayed at 37° C. in the above solution with 1 mM N-succinyl-Ala-Ala-Ala-p-nitroanilide and $OD_{405nm}$ was measured; cathepsin G activity was assayed at 25° C. in the above solution with 3 mM N-succinyl-Ala-Ala-Pro-Phe-p-nitroanilide and 500 mM NaCl and $OD_{410nm}$ was measured (DelMar, E. G. et al. (1979) *Analyt Biochem.* 99:316–320).

The activity of μ-plasminogen activator was assayed at 37° C. with 0.3 mM pyro-Glu-Gly-Arg-p-nitroanilide in 50 mM Tris HCl buffer, pH 8.8, 38 mM NaCl according to standard procedures. Proteinase-3 activity was assayed (Rao N. V. et al. (1991) *J. Biol. Chem* 256:9540–9548) at 25° C. with 0.5 mM of the p-nitrophenylester of t-butyloxycarbonyl-alanine (N-Boc-Ala-ONp) in 50 mM sodium phosphate buffer, pH 7.5, 2.5% methanol, 0.05% Triton X-100 (Pierce Chemicals) and $OD_{347nm}$ was measured. Preliminary experiments verified a linear response with respect to protease concentration. OD changes were measured every 15 sec. over 5 min. on a Model UV160U Recording Spectrophotometer (Shimadzu Corp., Kyoto, Japan) and were linear in all cases.

(14). Inhibitory Activity of recombinant HEI—To measure the ability of HEI to inhibit the above proteases, HEI-containing 6 day media of infected Sf9 cells (described above) was preincubated with 4 mM mercaptoethanol at 37° C. for 5 min to insure reduction of thiol groups. Volumes, equalized to 200 μl, were combined with 20 μl containing 700 ng of HNE, PPE, cathepsin G, proteinase-3 or μ-plasminogen activator, incubated at 37° C. for 3 min, and immediately assayed for residual peptidase activity using 800 μl of the appropriate assay mixture described above. Aliquots were also denatured by heating with 0.6 volume of 5% SDS, 8% mercaptoethanol, 25% glycerol, 100 μg/ml bromphenol blue and analyzed by SDS/PAGE and "gold staining".

(B). RESULTS AND DISCUSSION (1). Recombinant Baculovirus—To produce human monocyte/neutrophil Elastase Inhibitor (HEI), a cDNA including the HEI coding region cDNA (Sequence I.D. Number 13) was inserted into the vector pVL1393 (Autographa Californica nuclear polyhedrosis virus (AcNPV)) downstream of the polyhedrin promoter and the inactivated translation initiation codon.

The above step generated a recombinant transfer plasmid called pVL1393-HEI. To generate recombinant baculovirus, Spodoptera frugiperda insect cells (Sf9 cells) were cotransfected with the recombinant transfer plasmid together with linearized baculovirus DNA called BaculoGold DNA (PharMingen, San Diego, Calif.), which contains a lethal deletion. Occlusion-negative plaques generated by homologous recombination were retrieved after 2 weeks and no wildtype plaques were observed. Stocks of the recombinant virus, called AcNPV-HEI, were prepared by infecting Sf9 monolayer cultures and harvesting after 10–14 days.

Figure 7A:
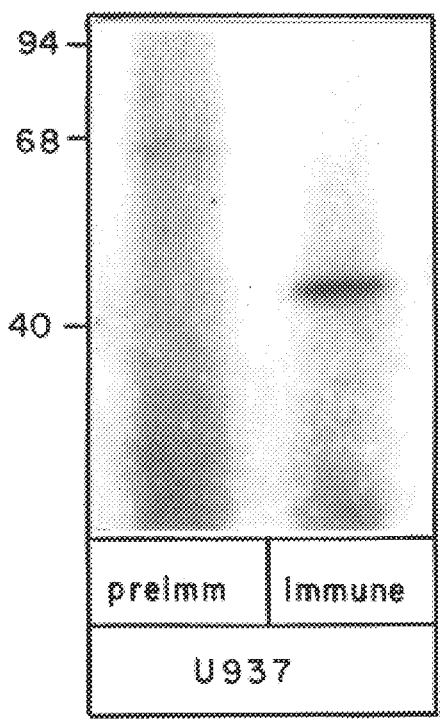
FIGS. 7A–7B show the detection of HEI by Western blot.
Figure 7B:
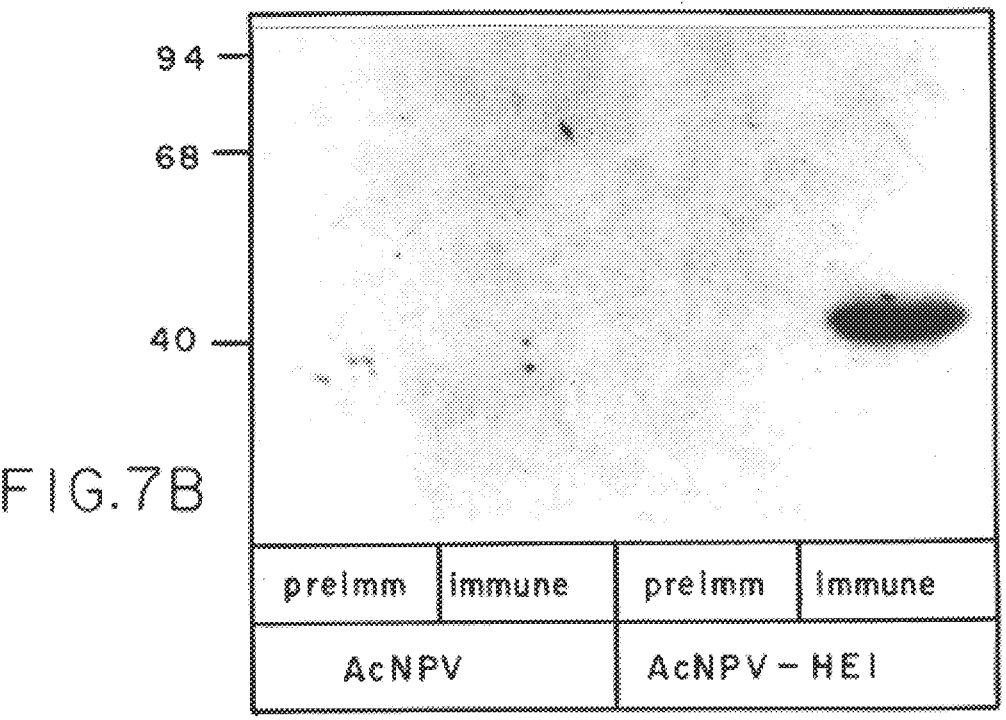

(2). Expression of Recombinant HEI in Insect Cells—Spodoptera frugiperda insect cells (Sf9 cells) were infected with the HEI-encoding recombinant virus (AcNPV-HEI) and an aliquot of the culture was examined after four days by Western blot. Antiserum raised against natural HEI from U937 cells (FIG. 7A) detected a ~42 kD polypeptide in the recombinant virus-infected Sf9 cell cultures (FIG. 7B); preimmune serum did not react with the polypeptide. No component was detected by the anti-HEI antiserum in uninfected Sf9 cells (data not shown) or in Sf9 cells infected with wildtype virus (AcNPV) (FIG. 7B). These findings indicate that AcNPV-HEI directs synthesis of a protein with the antigenic reactivity and approximate molecular mass of the naturally occurring HEI.

Figure 8A:
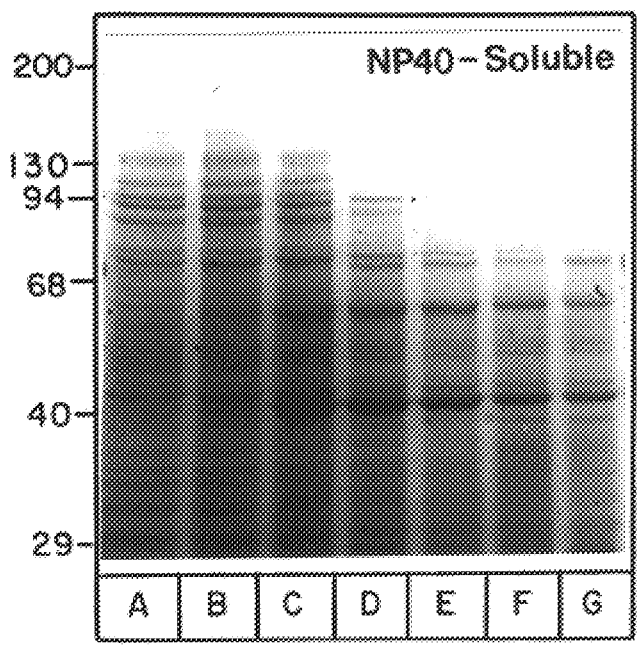
FIGS. 8A–8B show the time course of expression of soluble and insoluble rHEI in AcNPV-HEI infected Sf9 cells. Cells harvested at varying times were lysed and separated into NP40-soluble and NP40-insoluble fractions. Volumes derived from $3 \times 10^5$ starting cells were analyzed by SDS/PAGE and Coomassie blue staining (FIG. 8A, 8C) or Western blot with rabbit anti-HEI antiserum (FIG. 8B, 8D). The harvest times are: A, 0 h; B, 36 h; C, 64 h; D, 90 h; E, 115 h; F, 139 h; G, 155 h. Arrows indicate the 42 kD recombinant protein.
Figure 8B:
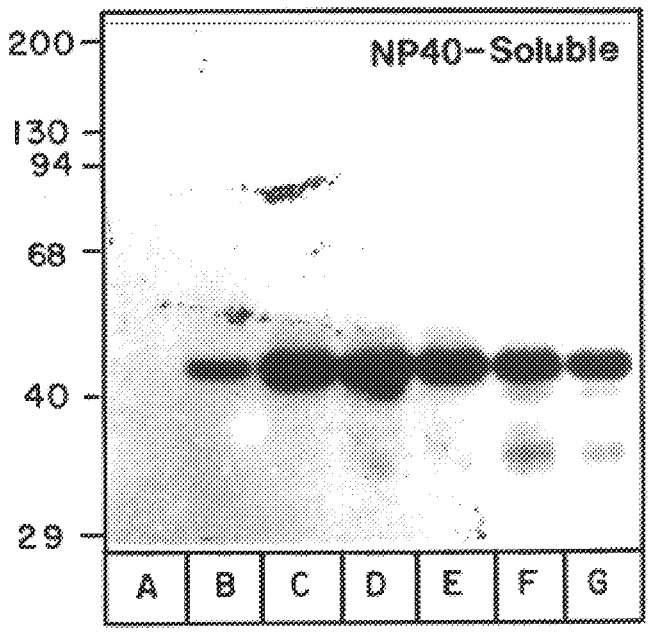
Figure 8C:
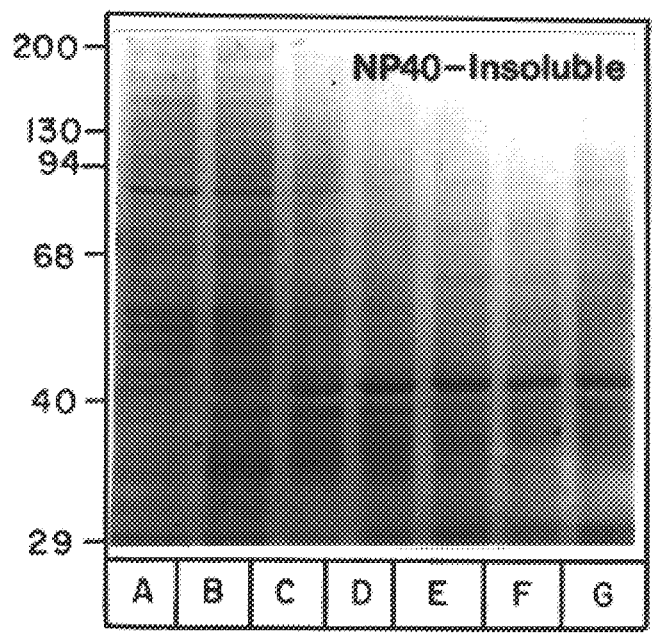
Figure 8D:
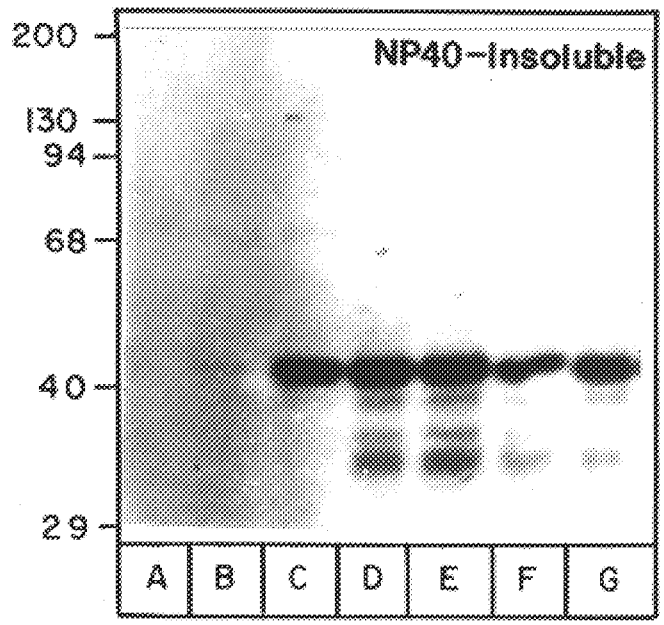

(3). Time Course and Compartmentation of HEI Expression in Insect Cells—At various times, the infected Sf9 cells were separated from media and examined by SDS/PAGE and Western blot. These denaturing techniques were expected to detect all recombinant HEI molecules, whether active or inactive, properly folded or aggregated. The lysed cells were separated into an NP40-soluble fraction containing cytosolic proteins and an NP40-insoluble fraction in the anticipation that recombinant HEI, if properly folded, would be found in the soluble fraction because natural HEI is a soluble cytoplasmic protein (Janoff, A. and J. Blondin (1971) *Proc. Soc. Exp. Biol. Med.* 136:1050–1053; Blondin, J. et al. (1972) *Am. Rev. Resp. Dis.* 106:477–479; Remold-O'Donnell, E. (1985) *J. Exp. Med.* 162:2142–2155; Thomas, R. M. et al. (1991) *J. Leukocyte Biol.* 50:568–579). An ~42 kD polypeptide was indeed detected in the NP40-soluble fraction in Coomassie blue stained gels (FIG. 8A, 8B) and in Western blots (FIG. 8C, 8D) beginning 2 to 3 days after AcNPV-HEI infection; the amount of the polypeptide increased with time and decreased again by day 5 (FIG. 8A, 8B). An ~42 kD polypeptide also was detected in the NP40 insoluble fraction, although in lesser amounts (FIG. 8C, 8D), suggesting that some recombinant HEI molecules form insoluble aggregates. The time course of appearance and disappearance of recombinant HEI was similar in the NP40 soluble and insoluble fractions (FIG. 8).

Figure 9A:
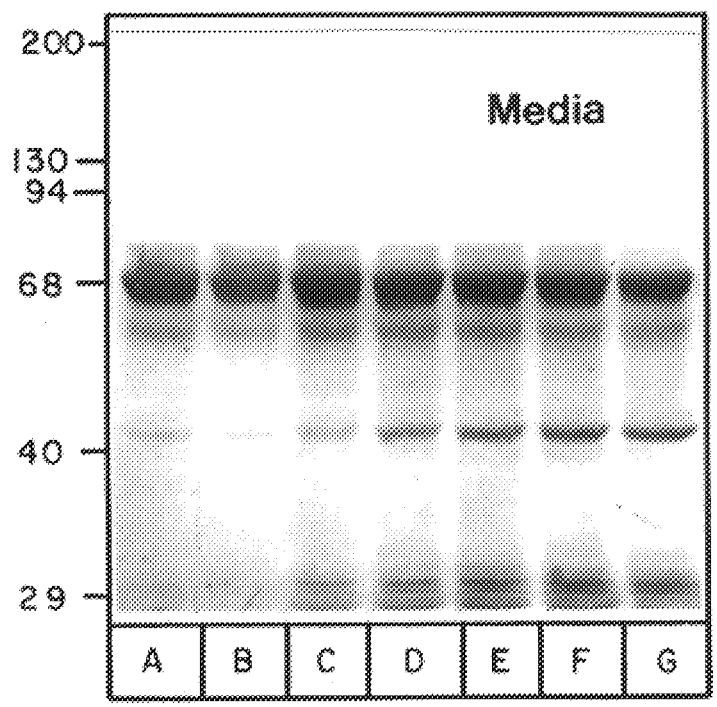
FIGS. 9A–9B show the time course of appearance of rHEI in media of AcNPV-HEI infected Sf9 cells.
Figure 9B:
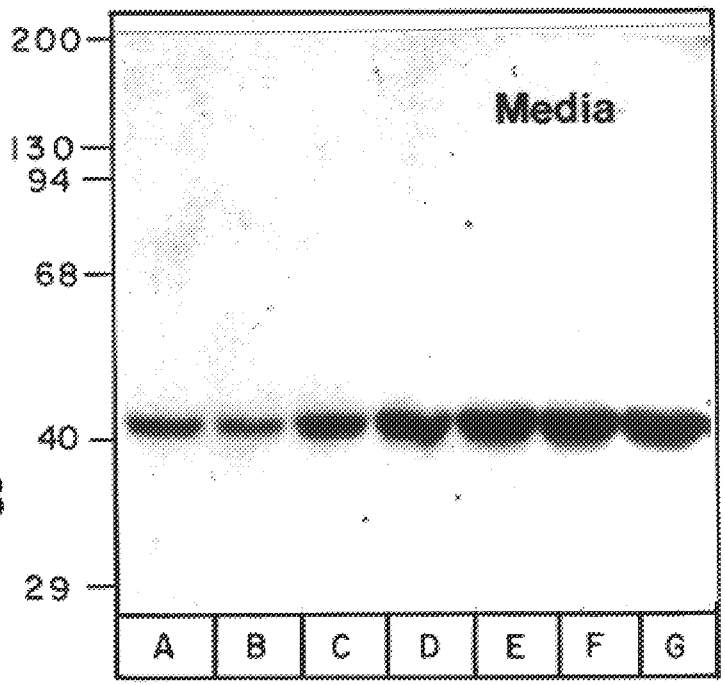
Figure 10:
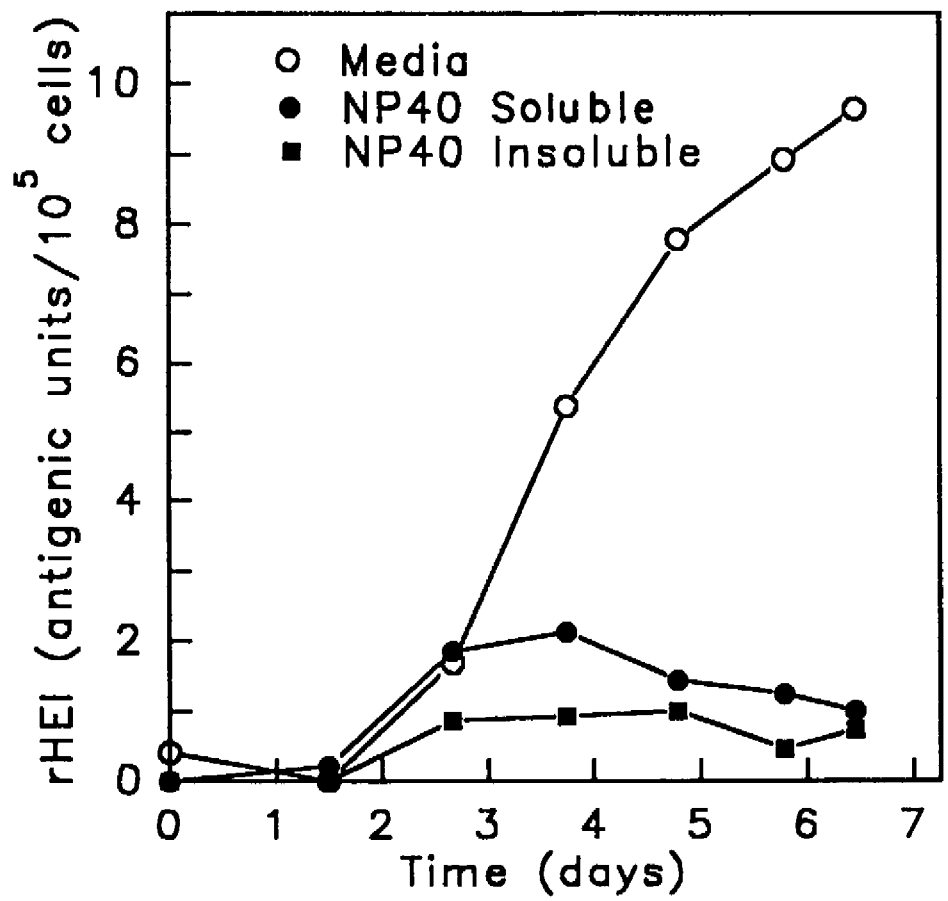
FIG. 10 shows the quantity of recombinant HEI in Sf9 cells infected with AcNPV-HEI. The 42 kD bands in Western blots (as in FIGS. 8 and 9) were quantified by phosphorimaging relative to an internal standard curve. Shown are arbitrary linear "antigenic units" in media, NP-40 soluble fractions and NP40-insoluble fractions derived from $10^5$ starting Sf9 cells as a function of time following infection.

(4). Released recombinant HEI—Surprisingly, high levels of recombinant HEI also were found in the culture media of infected cells. Coomassie blue staining and Western blots showed that recombinant HEI appeared in media on day 3 following infection of the Sf9 cells with AcNPV-HEI, and the amount continued to increase through days 6–7 (FIG. 9). The amount of recombinant HEI, determined for all fractions by phosphor-imaging of Western blots, is shown in FIG. 10 as arbitrary "antigenic units". The largest amount of HEI was found in media 5–7 days following infection. Recombinant HEI in culture media was quantified by densitometry of Coomassie-blue stained 42 kD bands ("protein units") and, when plotted as a function of time, "protein units" and "antigenic units" were superimposable.

The viability of Sf9 cells decreased late after infection (trypan blue uptake, data not shown), suggesting that the release of recombinant HEI may result from cell death. On the other hand, the total amount of recombinant HEI in the cultures increased dramatically during the late days (FIG. 10), indicating that most of the released recombinant HEI was synthesized at the time of secretion. Recombinant HEI may be released because of a feature present in its amino acid sequence. As noted above, Human EI is a member of the Ov-Serpin family, a protein family that is characterized by an internal hydrophobic signal sequence that can mediate secretion (reviewed in Remold-O'Donnell, E. (1993) *FEBS* 315:105–108). It is also possible that the unusual time course of synthesis and release of Human EI may be caused by some feature of the viral construct and/or by the very high expression levels of HEI in the baculovirus expression system. Although not completely understood, the methods described herein result in very high expression of HEI and its release into a serum-free media, thereby facilitating the production and purification of large amounts of the recombinant HEI.

(5). Yield of Recombinant HEI—The yield of recombinant HEI was determined by densitometry relative to an albumin calibration curve on Coomassie blue stained SDS/PAGE. For cultures infected under serum-free conditions, the yield for 6 day media of Sf9 cells infected with AcNPV-HEI was 15±3 $\mu$g per ml (mean±SEM, 5 experiments), which is equivalent to ~50 ug recombinant HEI per $10^6$ starting cells or ~400 times the content of U937 cells (Remold-O'Donnell, E. (1985) *J. Exp. Med.* 162:2142–2155).

(6). Glycosylation—Because its sequence includes several potential N-glycosylation sites (Remold-O'Donnell, E. et al. (1992) *Proc. Natl. Acad. Sci. USA* 89:5635–5639), it was important to determine whether released recombinant HEI was glycosylated. Recombinant HEI from media of infected Sf9 cells was treated with peptide N-glycosidase F (PNGase F), which cleaves all classes of N-linked carbohydrate units (Tarentino, A. L. et al. (1985) *Biochem.* 24:4665–4671). Whereas the molecular mass of the control glycoprotein, $\alpha$1-AT, was reduced by PNGase F treatment, the molecular mass of recombinant HEI was unaltered (FIG. 11), indicating that recombinant HEI of Sf9 cell media, like HEI isolated from lysates of U937 cells, is nonglycosylated.

Figure 12A:
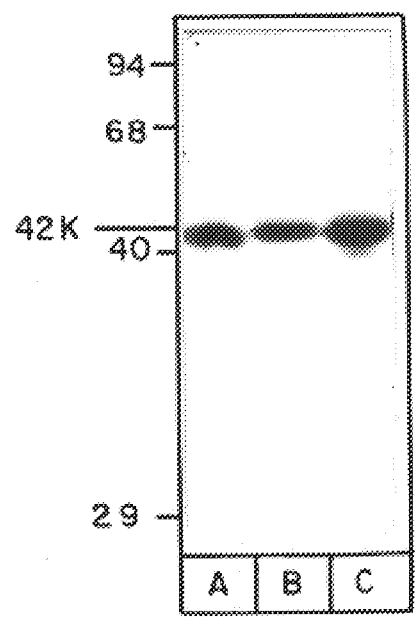
FIGS. 12A–12B show the co-electrophoresis of naturally-occurring and recombinant HEI.
Figure 12B:
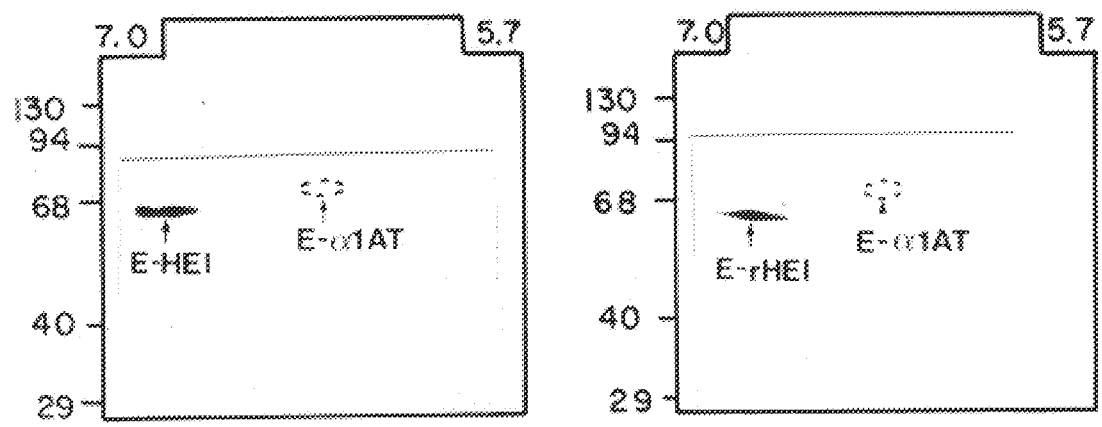

HEI from U937 cells, recombinant HEI harvested from the media of infected Sf9 cells, and recombinant HEI in the NP40-soluble fraction were found to co-migrate at 42 kD on Laemmli SDS/PAGE.(FIG. 12A), strongly suggesting identity. The isoelectric focusing behavior for recombinant Human EI also was indistinguishable compared to that of the naturally occurring HEI (FIG. 12B).

Figure 13A:
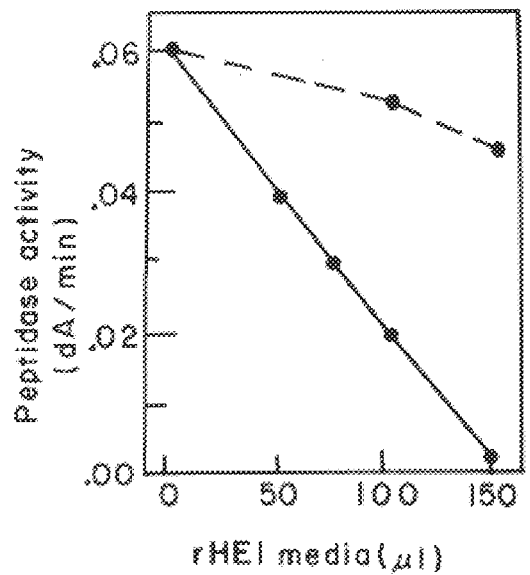
FIGS. 13A–13D show the inhibition of peptidase activity of human neutrophil elastase (HNE) (FIG. 13A) and porcine pancreatic elastase (PPE) (FIG. 13B) by increasing amounts of rHEI. Cleavage of N-methoxysuccinyl-Ala-Ala-Pro-Val-p-nitroanalide by 700 ng HNE, or N-succinyl-Ala-Ala-Ala-p-nitroanilide by 700 ng PPE was measured after preincubation for 3 min at 37° C. with the indicated volume of rHEI-containing media (6 day media of Sf9 cells infected with AcNPV-HEI; solid lines) or control fraction from cells infected with wildtype virus (dashed lines).
Figure 13B:
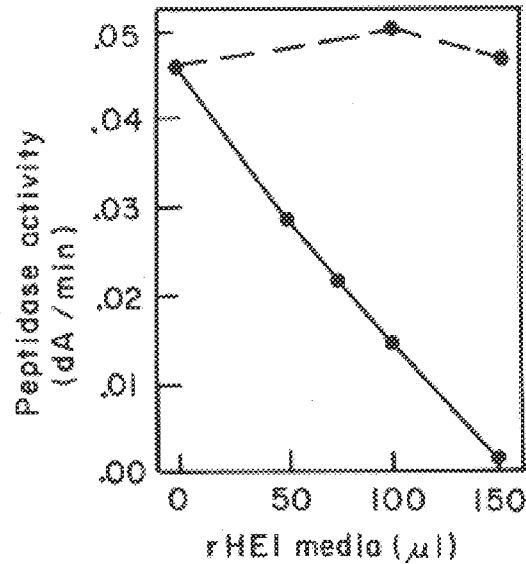

(7). Elastase Inhibitor Activity of Recombinant HEI—Recombinant LEI was tested for the known functions of natural HEI, the ability to form a covalent complex with, and thereby inactivate, human neutrophil elastase (HNE) and porcine pancreatic elastase (PPE) (Remold-O'Donnell, E. (1985) *J. Exp. Med.* 162:2142–2155; Remold-O'Donnell, E. et al. (1989) *J. Exp. Med.* 169:1071-1086). Dose-dependent inhibition of the peptidase activity of HNE and PPE as a result of a 3 min co-incubation with recombinant HEI-containing media (6 day media of AcNPV-infected Sf9 cells) is shown in FIG. 13A, 13B. HNE and PPE activities were only minimally affected by "control media" (6 day media of wild-type infected Sf9 cells) (dashed lines).

Figure 13C:
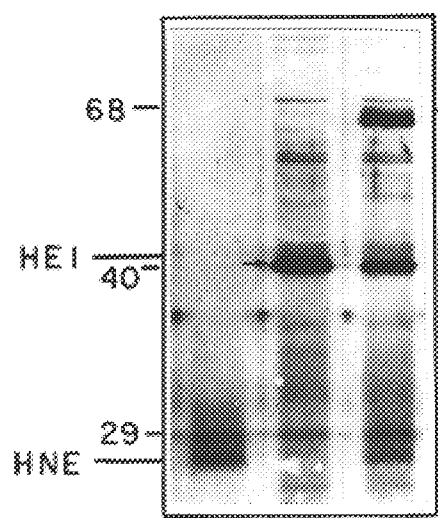
Figure 13D:
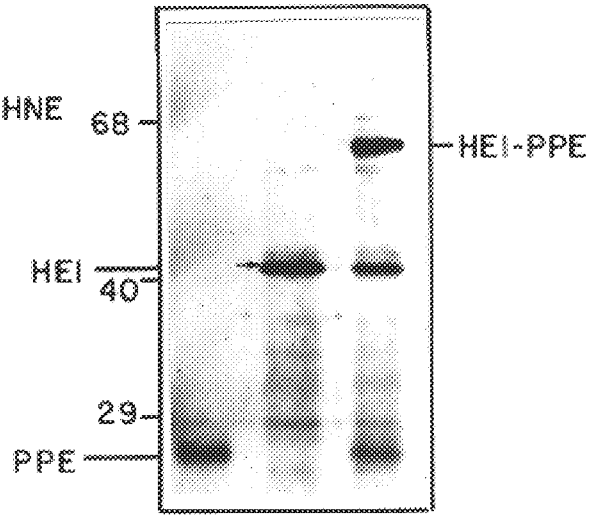

The ability of HEI to form a 1:1 covalent complex involving a new covalent bond with the active site of neutrophil elastase and pancreatic elastase, are shown for the recombinant protein in FIG. 13C, 13D. Cumulatively, these results indicate that recombinant HEI has the two known functional properties of naturally occurring HEI.

Figure 14A:
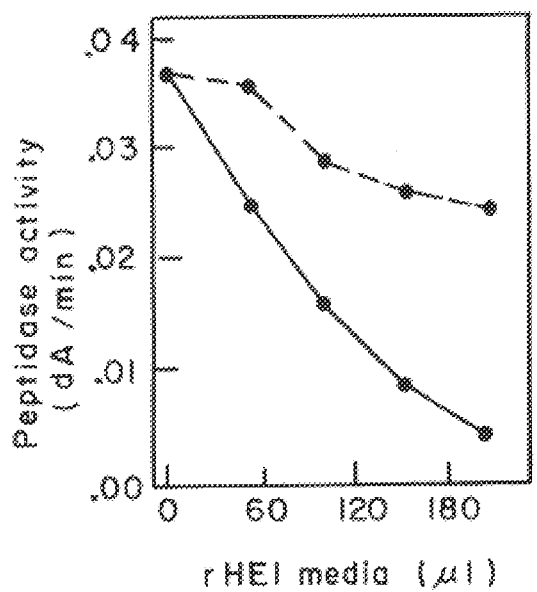
FIGS. 14A–14D show the inhibition of peptidase activity of human proteinase-3 (PR-3) measured with N-Boc-Ala-ONp (FIG. 14A) and human cathepsin G (cat-G) measured with N-methoxysuccinyl-Ala-Ala-Pro-Phe-p-nitroanilide (FIG. 14B) by increasing amounts of rHEI. Activity of 700 ng protease was measured after preincubation for 3 min at 37° C. with the indicated volume of rHEI-containing media (6 day media of Sf9 cells infected with AcNPV-HEI; solid lines) or control fraction from cells infected with wildtype virus (dashed lines).
Figure 14B:
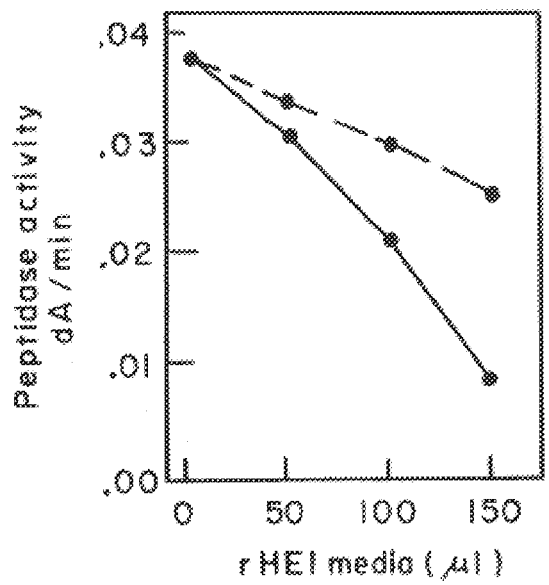
Figure 14C:
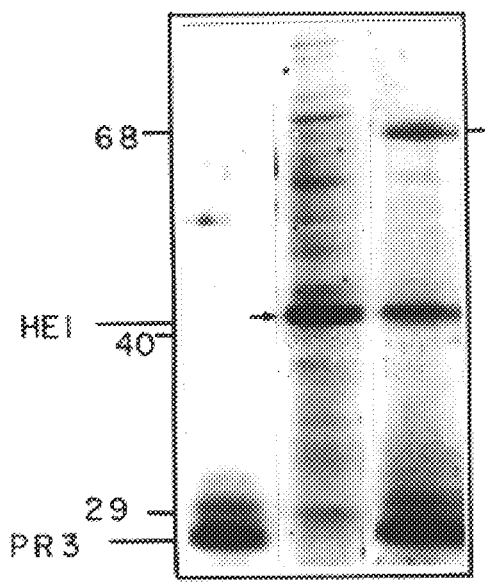

(8). Reactivity of HEI with Other Proteases—Recombinant HEI was tested for its ability to form a covalent complex with and inactivate the other serine proteases found with elastase in neutrophil azurophil granules: cathepsin G (Salvesen G. et al. (1987) *Biochemistry* 26:2289–2293) and proteinase-3 (Baggiolini M. et al. (1978) *Agents Actions* 8:3–10; Kao R. C. et al. (1988) *J. Clin Invest* 82:1963–1973; Campanelli D. et al. (1990) *J. Exp. Med.* 172:1709–1715). Proteinase-3 resembles neutrophil elastase in its preference for small aliphatic amino acids and its capacity to cleave elastin and cause lung matrix destruction (Baggiolini M. et al. (1978) *Agents Actions* 8:3–10; Kao R. C. et al. (1988) *J. Clin Invest* 82:1963–1973; Campanelli D. et al. (1990) *J. Exp. Med.* 172:1709–1715). The peptidase activity of proteinase-3 (PR-3) was inhibited in a dose-dependent manner as a result of a 3 min co-incubation with recombinant HEI-containing media and was affected to a much lesser extent by a 3 min co-incubation with control media (media of wildtype infected cells (FIG. 14A). The ability of recombinant HEI to form a 1:1 66,000 dalton covalent complex with proteinase-3 was also demonstrated (FIG. 14C). These findings strongly indicate an important new function for HEI, the ability to inhibit proteinase-3.

Figure 14D:
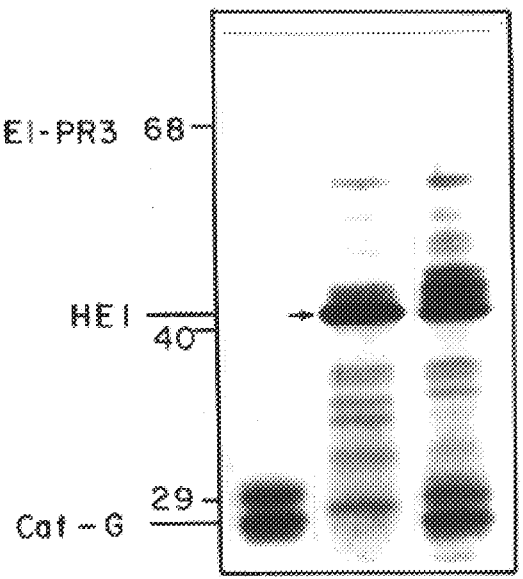

Dose-dependent inhibition of the peptidase activity of pure cathepsin G was detected after a 3 min co-incubation with recombinant HEI (FIG. 14B) and much lesser inhibition with control media (dashed lines). However, a covalent complex of recombinant HEI and cathepsin G was not detected (FIG. 14D). Co-incubation of cathepsin G and recombinant HEI increased the amount of protein detected as a broad band having a molecular mass greater than HEI (42 kD), suggesting that a complex was formed and degraded; this result was not altered by decreasing the time of co-incubation (to 1 min) or varying the ratio of reactants. These findings suggest that cathepsin G is inhibited by Human EI. Further characterization of the reactivity of recombinant HEI and cathepsin G can be performed in accordance with methods known to one of ordinary skill in the art to further delineate the interaction of Human EI with cathepsin G.

Figure 15A:
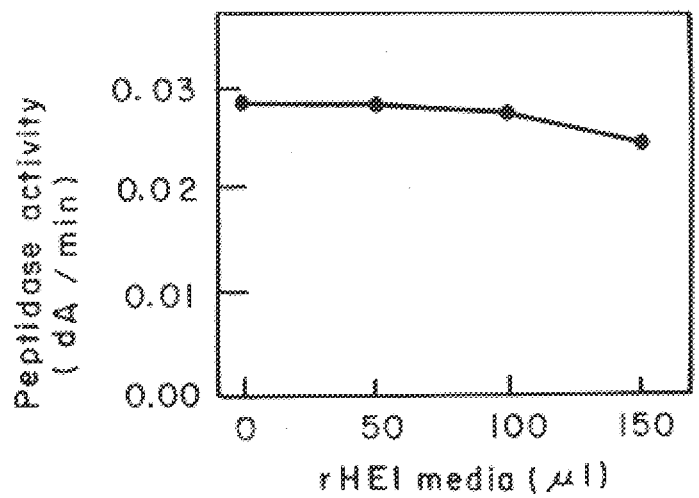
FIG. 15A shows the absence of rHEI inhibitory activity on the peptidase activity of human urokinase (measured with pro-Glu-Gly-Arg-p-nitroanilide). Peptidolytic activity for 700 ng urokinase was measured after preincubation for 3 min at 37° C. with the indicated amounts of rHEI-containing medium (6 day media of Sf9 cells infected with AcNPV-HEI).
Figure 15B:
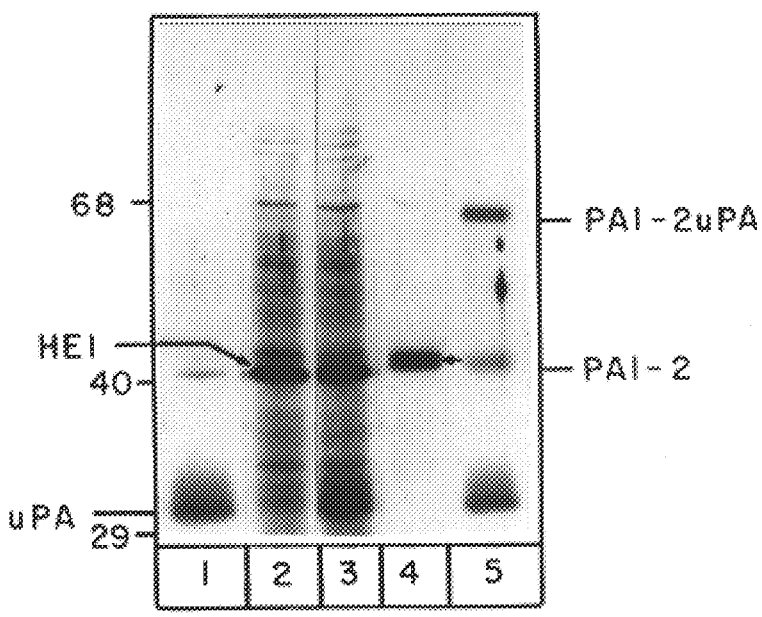
FIG. 15B shows the complex formation assay: Shown are gold-stained SDS/PAGE of 500 ng u-plasminogen activator (1st lane) and 6 μl rHEI (6 day media of infected Sf9 cells) (2nd lane) and the combination of these agents after 3 min co-incubation at 37° C. (3rd lane). No new covalent complex is detected. Also shown is a positive control consisting of 100 ng rPAI-2 (shown alone in the fourth lane) and after incubation for 3 min with 500 ng u-plasminogen activator to form a 72 kD covalent complex (5th lane)

Co-incubation of pure $\mu$-plasminogen activator with increasing amounts of recombinant HEI did not alter its peptidase activity (FIG. 15A). Neither did recombinant HEI and $\mu$-plasminogen activator (33 kD) form a covalent complex when co-incubated for 3 min (FIG. 15B). As a control, $\mu$-plasminogen activator was co-incubated for 3 min with its known inhibitor PAI-2 (46 kD) (Vassalli J-D. et al. (1984) *J. Exp. Med.* 159:1653–1658; Ye R. D. et al. (1987) *J. Biol. Chem.* 262:3718–3725) and a 72 kD covalent complex of uPA-PAI-2 was detected in gold stained gels (FIG. 15B).

V. OPTIMIZATION OF rHEI EXPRESSION AND PURIFICATION (A). Optimization of rHEI Expression Sf9 cells infected with AcNPV-HEI by the above-described method (high-density co-incubation of cells in virus) and placement in spinner culture with 10% serum ("high serum" cultures) produced rHEI, and as shown above, culture media rather than cells was the richest source of rHEI. The expression conditions were optimized to determine whether rHEI could be expressed in medium containing low or no serum. Whereas, "high serum" culture of Sf9 cells infected with AcNPV-HEI invariably produced rHEI, the success rate for "low serum" (0.3% serum) cultures was far lower (9 of 17 cultures). Success versus failure of the rHEI expression by the low serum cultures did not correlate with any identifiable property of the cells, viral stock, or experimental manipulations. When serum was entirely omitted from the expression cultures ("no serum" cultures), the success rate was negligible (1 of 13 experiments).

The unexplainable failure of infected Sf9 cells to produce rHEI in some "low serum" cultures and most "no serum" cultures was overcome by making a procedural change, namely, using stationary tissue culture flasks (Nunclon® Flasks, Nunc Inc., Naperville, Ill.) rather than spinner flasks for the expression culture. The infection protocol was not otherwise changed. Expression of rHEI under serum-free conditions has been consistently successful under these stationary phase expression conditions (13 of 13 infections). It thus appears that Sf9 cells infected with AcNPV-HEI require either the presence of serum or the presence of a surface to which the infected cells can adhere in order for successful expression of rHEI. The time course of expression of rHEI, i.e., very late synthesis, as well as its release into media, was similar under all successful conditions. The use of T-flasks for rHEI expression cultures can be exploited for the large scale production of recombinant human EI. The use of serum-free culture conditions has facilitated the purification of rHEI.

(B). Affinity Purification of rHEI

An affinity chromatography method for the small scale purification of rHEI is described herein. Several purification materials were examined for the affinity purification of the recombinant protein. Chromatography on thiopropyl-sepharose (Pharmacia/LKB) provided a single-step purification of rHEI. According to this protocol, six day media (serum-free) of infected insect cells was treated with 2 mM mercaptoethanol for 10 minutes at 22° C. to insure that rHEI molecules were in an active monomeric state, dialyzed against 10 mM Tris HCl, pH 7.4, 150 mM NaCl, (Tris saline) and reacted batch-wise with thiopropyl-sepharose for thirty minutes at 22° C. The resin was poured into a column, washed with Tris-saline and eluted with 50 mM mercaptoethanol in Tris-saline. The eluted rHEI retained the ability to inhibit human neutrophil elastase (peptidolytic assay and complex formation assay). The eluted rHEI appeared homogeneous when analyzed by Coomassie blue-stained SDS/PAGE gels and by gold-stained gels. This purification procedure can be optimized for large batches of recombinant human EI in accordance with standard procedures known to those of ordinary skill in the art.

VI. PREPARATION OF ANTIBODIES TO HUMAN EI.

(A). Monoclonal Antibodies: To generate antibodies for use as affinity reagents, mice were immunized with pure U937 HEI and later with rHEI. The immunogen was pretreated with iodoacetamide to preserve the protein's active confirmation, which would have been lost following injection if active HEI had been allowed to contact and react with a protease in situ (because serpins change confirmation following complex formation). Iodoacetamide inactivates HEI, presumably by derivatizing the P1 cysteine in the exposed active site loop.

Fusions were screened by immune precipitation with rabbit antibody to HEI, SDS PAGE and autoradiography using partially purified HEI from U937 cells that had been labelled with [$^{35}$S] methionine. Three anti-HEI monoclonal antibodies were generated, Ela-1, Ela-3, and Ela-5, that recognize at least two independent epitopes. Each of the monoclonal antibodies immunoprecipitated naturally occurring and recombinant HEI but did not immunoprecipitate any component of uninfected insect cells or CEM lymphoblastoid cells. Each antibody removed HEI from infected Sf9 cell media and U937 cell lysates, thus indicating that the binding properties of these antibodies were appropriate for use as affinity reagents. Accordingly, it is believed that at least one of these monoclonal antibodies can be used as an immune precipitating agent to detect extracellular $^{35}$S-labelled HEI or to prepare an immunoaffinity resin as a detection reagent in ELISA and/or fluorescent microscopy and/or flow cytometry using permeablized cells.

(B). Rabbit Antibodies

Of the monoclonal antibodies, only E1-A-5 reacted on Western blots, however, its affinity for Human EI was moderate. The preferred Western blot reagent was a high-affinity rabbit antiserum that had been generated by immunizing a rabbit with recombinant HEI that had been denatured with hot SDS ("1994 Antiserum"). A rabbit "1989 Antiserum" (a low-affinity reagent), generated by immunizing a rabbit with limited amounts of SDS-denatured U937 cell HEI, was used for characterizing the above-described recombinant HEI. Two additional high-affinity rabbit antisera ("1993A and 1993B Antisera") were generated by immunizing animals with active HEI. It is believed that at least one of these high-affinity rabbit antiseras can be used as an ELISA capture reagent.

VII. ORGANIZATION OF THE OV-SERPIN GENES AND CHROMOSOMAL LOCATION OF THE HUMAN EI.

(A). Organization of the Ov-Serpin Genes

Studies of serpin genes found, surprisingly, that intron positions can vary widely within the superfamily. At least five distinct organizational patterns have been defined. Within the Ov-serpin family, however, the three characterized genes (chicken ovalbumin, chicken gene Y and human PAI-2) share a common gene organization of eight exons and seven introns with identical positions and phases for each intron. Because the shared gene organization of ovalbumin/gene Y and PAI-2 is complete and atypical of the larger superfamily and unrelated to the function of the encoded protein as well as being independent of species, we concluded that the gene organization pattern for the Ov-serpin genes is a meaningful property for identifying additional members of that family.

(B). Partial Characterization of ELANH-2, the Gene that Encodes HEI

The Human Genome Database recently determined that the gene which encodes HEI will be designated with the international symbol "ELANH-2" (ELAstase INHibitor-2). PCR methodology was used to determine whether the gene which encodes HEI has an organizational pattern corresponding to the PAI-2 and ovalbumin genes. Because HEI lacks a variable loop, its gene, if similar to the PAI-2/ovalbumin genes, would have one less exon and intron, i.e., seven exons and six introns.

Figure 16:
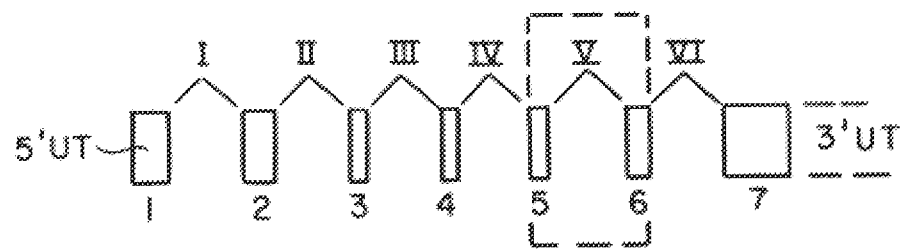
FIG. 16 is the hypothesized organiztion of ELANH-2, the gene encoding HEI. Solid bars indicate coding region exons and open bars indicate untranslated regions. Roman numerals indicate the introns. In the proposed model based on homology with the PAI-2, ovalbumin and gene Y genes, exon-1 would be 5'-untranslated region; exon-2, untranslated through coding position 216; exon-3, positions 217–354; exon-4, 355–472; exon-5, 473–615; exon-6, 616–783; and exon-7, position 784 past the stop codon at position 1189 to the unidentified end of the 3'-untranslated region.

Segments of the HEI cDNA that would constitute individual exons if ELANH-2 had the organization of the PAI-2/ovalbumin genes were identified. Primers from predicted adjacent exons (predicted exon-5 and predicted exon-6 were initially selected) were used to amplify genomic DNA between nucleotides 615 and 616 of the cDNA sequence of human monocyte EI. The PCR products were verified using nested primers, electrophoresed, transferred to a membrane and hybridized with an alkaline phosphatase-conjugated oligonucleotide corresponding to an internal HEI sequence (enzymatically tagged internal oligo) (FIG. 16). The intron (tentatively named intron V) is disclosed in Sequence I.D. number 16.

The amplified genomic DNA product was slightly larger than the amplified cDNA. Sequencing analysis verified the presence of an 83 bp intron, presumably intron-V. The intron begins with GT and ends with AG, thus obeying the "GT-AG" rule for intron sequences. The ELANH-2 intron is located between cDNA positions 615 and 616, which correspond precisely to the intron-VI position in the PAI-2 and ovalbumin genes. There were no other interruptions in the exon five and six sequences. Thus, the organization of the ELANH-2 in this region is identical to the organization of the genes for PAI-2 and ovalbumin, providing further evidence that HEI is indeed a member of the Ov-serpin family. The above-described PCR methodology can be used to examine additional adjacent regions of the ELANH-2 gene in order to further characterize the organizational structure of this gene.

(C). Chromosomal Location of ELANH-2, the Gene Encoding HEI

Genomic DNA from human-rodent somatic hybrid cells was used to determine the chromosomal location of ELANH-2. The genomic DNA contained a full complement of rodent chromosomes and a characterized, limited number of human chromosomes. DNA from the mouse/human (predominantly) and Chinese hamster/human hybrid panel and the three parental DNAs was from the Human Genetic Mutant Cell Repository of the National Institute of General Medical Sciences and was obtained from Coriell Institute, Camden, N.J.

To detect the ELANH-2 gene, each panel DNA was subjected to the above-described amplification procedure for the intron-V region. The amplified ELANH-2 region was detected as a 360 bp ethidium bromide-stained band in a subset of the hybrid DNAs and in the human parental DNA, but not in the mouse DNA or Chinese hamster DNA. The identity of the PCR product was verified as ELANH-2 by hybridization with the enzyme-tagged internal oligonucleotide as described above. A concordancy/discordancy scoring system was used to relate the presence or absence of each chromosome with the presence or absence of the amplified ELANH-2 product. A perfect score of 0 discordancy permitted the localization of the ELANH-2 gene to chromosome six.

The DNA from additional hybrid cells was provided by Dr. Huda Zoghbi, Department of Human and Molecular Genetics, Baylor College of Medicine. These hybrids contained either the short-arm or the long-arm of human chromosome six. Using the above-described PCR methodology, ELANH-2 was localized to 6p, the chromosome six short arm. Further regional localization of ELANH-2 using hybrid DNAs representing subregions of 6p (provided by Dr. Zoghbi) can be performed as described above. Localization to chromosome six indicates that ELANH-2 does not form a gene cluster with the gene encoding PAI-2 (PLANH-2) on chromosome 18. The absence of a gene cluster including ELANH-2 and PAI-2 is consistent with the findings of differential regulation of the PAI-2 mRNA and HEI mRNA in monocytes (described above). Knowledge of the localization of ELANH-2 to 6p permits the examination of surrounding polymorphic markers in families for which variations in ELANH-2 can be correlated with inherited disease.

VIII. PRE-CLINICAL STUDY OF RECOMBINANT HUMAN EI. Introduction

The above-described recombinant human EI appears to be identical to human EI isolated from monocyte-like cells. Because the primary physiological locations of HEI are tissue sites that have been infiltrated with neutrophils, monocytes and macrophages, local application of recombinant HEI to an inflammatory site is initially tested.

(A). Oxidation and Protease-Sensitivity of Protein Inhibitors of Human Neutrophil Elastase (HNA)

The two well studied protein inhibitors, α1-AT and SLPI are known to be eventually inactivated by proteases and oxidants released by neutrophils. One explanation for the sensitivity of these inhibitors to oxidation and proteolytic digestion at inflammatory sites may be to provide the physiological function of slowly returning the tissue site to a normal HNE expression level, i.e., to rapidly restore the protease/antiprotease balance by inactivating excess HNE by the inhibitor and thereby permit surviving neutrophils to respond to a new inflammatory challenge. Thus, it is believed that susceptibility to eventual oxidation and/or proteolytic inactivation is an important feature for HNE inhibitors to be effective as pharmacological agents. Accordingly, the oxidation sensitivity of recombinant HEI is examined in the same manner as described for the α1-AT and SLPI inhibitors (Ossanna, P. et al., J. Clin. Invest. 77:1939 (1986); Vogelmeier, C. et al., J. Clin. Invest. 87:482 (1991)) to determine whether the Human EI exhibits oxidation sensitivity that is comparable to these known protease inhibitors. That the oxidant N-chlorosuccinimide does not inactivate recombinant human EI contained in media of infected Sf9 cells has already been established.

(B). Pre-Clinical In Vivo Animal Studies and In Vitro Experiments

The functional capacity of purified rHEI within an in vitro environment that approximates the human inflammatory lung environment is tested through the use of sputum obtained from cystic fibrosis patients. The functional capacity of pure rHEI to inhibit human neutrophil elastase is examined in vivo in a multi-parameter rat model in which lung damage is induced by instilled human neutrophil elastase or human neutrophil elastase contained within cystic fibrosis sputum (Rees, D. D. and Brain, J. D. (1993) Ped. Pulmon. Suppl. 9:250). These systems are selected as particularly appropriate for evaluating the efficacity of rHEI because they specifically address damage to the lung that is induced by human neutrophil elastase. The distribution and clearance in the rat lung model is determined using the reagents described above (i.e., the antibodies directed to human EI). Consistent with the pre-clinical examination of other therapeutically useful proteins, preliminary evaluation of rHEI includes evaluation of its toxicity in animal models, examination of storage stability, and examination of the sensitivity of pure rHEI to various oxidants and its suitability to delivery by aerosolizing methodology.

Equivalents

It will be understood by those skilled in the art that there may be multiple related, but slightly different forms of naturally-occurring Human EI. Therefore, it further will be understood that there may be more than one mRNA sequence and more than one corresponding cDNA sequence encoding for naturally-occurring Human EI. However, each such DNA sequence may be isolated according to the procedures set forth above and each form of Human EI may be obtained by expression vectors carrying each such cDNA sequence. Likewise, the genomic DNA corresponding to the various forms of Human EI then may be isolated in a conventional manner.

It will be understood by those skilled in the art that there are many other equivalents to the foregoing description of the preferred embodiment. While the invention provides, among other things, a method for obtaining a cDNA copy of the mRNA for Human EI and the expression of that cDNA, various functional variations of the cDNA and the expressed product are contemplated as within the scope of the invention.

For example, cDNA sequences encoding Human EI may be changed at one or more base-pair positions or portions of the cDNA may be deleted while still retaining the ability of the expressed protein to act as an inhibitor of elastase or of other serine proteinases. The expressed protein therefore may include amino acid substitutions or deletions yet still be the functional equivalent of naturally occurring Human EI.

As an example, the degeneracy of the genetic code results in many amino acids being specified by more than one codon. Accordingly, a genetically engineered cDNA for Human EI, includes a DNA sequence corresponding to the naturally occurring gene, a sequence corresponding to a non-naturally occurring gene having nucleotide substitutions which do not affect the amino acid sequence of the translation product of the gene, and sequences corresponding to variations, derivatives or portions thereof that maintain the ability of the cDNA to be translated into a protein product having the ability to complex with and/or inhibit the activity of elastase. Thus, genetically engineered Human EI, includes naturally and non-naturally occurring Human EI, and functionally equivalent proteins, peptides and peptide analogs thereof that maintain their ability to complex with and/or inhibit the elastinolytic activity of elastase.

As another example, the polymerase chain reaction (PCR) can be used to produce DNA sequence changes by manipulating oligonucleotide primers rather than by manipulating DNA fragments with restriction and ligation enzymes. PCR products readily accept such sequence changes as 5' "add-on" sequences to the primers. Furthermore, the efficiency at which the modified product is produced is nearly 100%. A restriction site sequence is easily introduced into a DNA fragment produced by PCR merely by attaching these sequences to the 5' ends of the oligonucleotide primer (Scharf et al., 1986, Science 223:1076). Although these sequences are mismatched to the template DNA, in most cases they have little effect on the specificity or efficiency of the amplification because specificity is primarily imparted by the 3' end of the primer. As strands initiated by these "add-on" primers are themselves copied, the added restriction site sequence becomes fixed into the growing population of PCR product fragments. The principle of introducing DNA alterations by way of PCR primers can be used to help create DNA fragments altered in sequence at any position in, or to recombine DNA sequences at any desired junction.

Using PCR methodology, a generalized mutagenesis protocol is accomplished by developing oligonucleotide primers that are mismatched to the target sequence at at least a single base. This primer-introduced sequence modification is limited by length constraints on the chemical synthesis of the primer. Nevertheless, this process is used with PCR to combine PCR products from different sections of the sample DNA template such that the resulting fragments overlap in sequence. The overlapping PCR products, containing the site-directed mutation, are mixed, denatured and allowed to reanneal. This process of PCR fragment joining is useful for introducing a sequence alteration at any position in the fragment. (See generally, Mullis, K. et al, 1986, Cold Spring Harbors Symposium 51:263). A specific protocol for site-directed mutagenesis and recombination using PCR can be found in Higuchi, "Using PCR to Engineer DNA", pages 68–69, in PCR Technology ed. H. Erlich, Stockton Press (1989). Since the overlap necessary to effect the combination need not exist in the natural DNA template, but can be made as an add-on sequence to the primers, PCR is used to create specific site substitutions, deletions, and insertions at nearly any position in a DNA fragment as well as to combine previously unrelated sequences at precise junctions. These techniques have previously been used to place substitutions in the middle of a 300–800 bp PCR fragment, Higuchi, R. et al, 1988, Nucl. Acid Res. 16:7351. Insertions and deletions as add-on sequences have been demonstrated by Vallette et al., 1989, Nucl. Acid Res. 17:723, and the precise recombining of four different sequences to create a 970-bp DNA fragment coding for a chimeric protein has been shown by Horton et al., 1989, Gene 77:61.

The PCR method is an easy way of creating specific new DNA sequence combinations and can be used in conjunction with the above-disclosed assays to determine the presence or absence of elastase inhibitor activity to provide a method for creating functionally equivalent peptides and peptide analogs of a human elastase inhibitor.

Such a method includes the steps of cloning a human elastase inhibitor cDNA using the above-disclosed method; introducing restriction site sequences, insertions, deletions or other site-directed modifications into this DNA sequence using, for example PCR methods; inserting the resulting DNA product into an appropriate expression vector using the known restriction sites as discussed herein or, ultimately introducing known restriction sites into the DNA sequence with PCR methodology; expressing the modified DNA in an appropriate expression system, for which a wide variety of vectors are available; expressing the resulting human elastase inhibitor product and testing the ability of this product to form a covalent complex with elastase and/or inhibit the elastinolytic activity of elastase (Remold-O'Donnell, E. and K. Lewandrowski, J. Biol. Chem. 258:3251–3257 (1983); Remold-O'Donnell, E., J. Exp. Med. 162:2142–2155 (1985)). Subsequently, the expression product is purified for diagnostic, therapeutic or other applications.

Functionally equivalent peptides and peptide analogs of Human EI with altered active site sequences, particularly, but not limited to, the P1 residue adjacent to the cleavage bond, can be prepared which have altered inhibitory activity toward elastase and/or other serine proteases. The correlation between protease inhibitory activity and the nature of the P1 residue has been demonstrated for α1-antitrypsin using site-directed mutagenesis of the reactive site P1 residue (See, for example Matheson, N. R. et al., 1986, *J. Biol. Chem.*, 261: 10404–10409; Courtney, M. et al., 1985, *Nature* 313: 149–151). This approach, which has found applicability also for other Serpin molecules (e.g., antithrombin III) demonstrates that active site mutants of Serpin molecules, particularly P1 variants, can be generated which have increased or decreased inhibitory activity (measured as second order association rate constants) for particular serine proteases.

In a similar manner, active site variants can be produced with altered stability to oxidants, a feature that is believed to be important in the case of human EI, which like α1-antitrypsin, has an oxidation sensitive residue in the active site. Variants of human EI can be produced by techniques such as site-directed mutagenesis in which the active site P1 Cys residue is replaced by an oxidation resistant residue such as Val or Ala (which resemble Cys in size, hydrophobicity and lack of charge) in order to generate a variant EI molecule with similar inhibitory properties but which is resistant to inactivation by oxidants such as those produced by cigarette smoke and active phagocytic cells. Generation by site-directed mutagenesis of recombinant α1-antitrypsin variant molecules in which the oxidation sensitive Met residue was replaced by either Val or Ala did not greatly alter the elastase inhibitory activity; however, the mutant molecules were resistant to denaturation by oxidants (Matheson et al., supra). Thus, a modified Human EI can be formed in which Val or Ala is substituted for Cysteine as the P1 amino acid in HEI. The modified HEI then can be tested for functional EI activity and increased resistance to oxidation.

Variant human EI with increased resistance to oxidants may be preferred for some applications, since the amount needed for a pharmacologically desirable inhibitory function would be reduced. However, in most cases, human EI and functionally equivalent EI peptides and peptide analogs that are oxidation sensitive may be preferred. Both Serpin superfamily molecules, alpha1-antitrypsin and HEI, which function as effective elastase inhibitors, have P1 residues, which are oxidation-sensitive. This coincidence is not explained by a particularly close relatedness of the molecules because they have (only) 30.3% identical residues compared, for example, to 50.2% identical residues in human EI and plasminogen activator inhibitor II. Moreover, the oxidation sensitive P1 residue is not the same in the two inhibitors. Thus, oxidation sensitivity seems to have evolved independently in two of the Serpin elastase inhibitory molecules, perhaps reflecting the need for elastase inhibitory molecules to only act at specific locations and/or for restricted times.

By site directed mutagenesis or more recently developed methods such as PCR-based methods described above, recombinant functional equivalents of EI can be produced having one or more altered residues (particularly P1 and other active region residues), so as to alter the inhibitory properties of human EI and render the variant molecule useful in other applications. A mutant human EI recombinant molecule with Arg substituted in P1 position with or without additional substitutions can have greatly reduced elastase inhibitory activity and can function instead as an inhibitor of thrombin, as for example, an anti-clotting agent. Alternatively, recombinant human EI variants with P1 Arg can function to inhibit plasminogen activator or C1-esterase and function in different applications. Other variants and applications also are envisioned within the scope of the present invention.

In this regard it will be understood by those skilled in the art that a molecule may inhibit the activity of elastase without forming a covalent complex with elastase. Thus, peptides of Human EI, (preferably those including the sequence of the elastase binding region of Human EI) can have sufficient affinity for elastase so as to bind to and inhibit elastase, but not form a covalent complex with elastase. Such functionally equivalent peptides and peptide analogs are contemplated as being within the scope of the invention. These peptides may be prepared by conventional peptide synthesis or recombinant techniques.

The invention also contemplates functionally equivalent peptides and peptide analogs of Human EI that are coupled with moieties capable of reacting with the active site of a serine proteinase. In this instance, the peptides recognize the serine proteinase and deliver the active moiety for inhibitory interaction with the serine active site.

Human EI also can be useful in inhibiting other serine proteases in addition to elastase. For Serpin molecules, the spectrum of inhibited proteases is determined in a general way by the residues in the active site, particularly the P1 residue adjacent to the cleavage bond. Thus, a naturally occurring mutant of α1-antitrypsin in which the P1 residue had mutated from Met to Arg, functioned poorly as an inhibitor of elastase but was a very effective inhibitor of thrombin, which is not normally inhibited by α1-antitrypsin (Owen, M. C. et al., N. Engl. J. Med. 694–698). Although some Serpin molecules have sharply defined specificities, inhibiting primarily a single serine protease others, including α1-antitrypsin which has a Met residue in the P1 position, have somewhat broader specificity. The apparent counterpart molecule of Human EI in guinea pigs inhibits both elastase and trypsin (E. Remold-O'Donnell and Lewandrowski, 1983, *J. Biol. Chem.*, 258:3251). Moreover, a recombinant mutant of μl-antitrypsin with a Cys residue in the P1 site, as is found in the Human EI sequence, inhibited both elastase and chymotrypsin (Matheson et al., supra). Thus, functional studies can be carried out using recombinant human EI to reveal that human EI inhibits more than the one serine protease. As described above, Human EI can form a complex with proteinase 3 and also appears to form a complex with cathepsin G. Both of these proteinases are serine proteases found with elastase in the azurophil granules of neutrophils and also contribute to degradation of extracellular matrix proteins in disease states. Likewise, Human EI may function naturally or may have pharmacological application in the inhibition of the serine proteases (e.g. Hayes, M. P. et al., 1989, *J. Exp. Med.* 170:933–946) in granules of cytolytic T lymphocytes, natural killer cells and mast cells and may have application in preventing adverse action of these proteases.

Cleavage products (i.e., peptides, proteins) of Human EI also can be used as inhibitors of elastase. In a particularly preferred embodiment, such peptides form a complex with and inhibit the elastinolytic activity of elastase. However, peptides of Human EI that can form a complex with elastase but which cannot inhibit the elastinolytic activity of elastase also are useful. For example, peptides of Human EI that form a complex with elastase but that do not interfere with the activity of elastase, can be used to block the inhibitory action of Human EI in situ by preventing formation of the Human EI-elastase complex. Such peptides can be identified by performing screening assays which are based upon the above-described complex forming and/or elastinolytic inhibitory activities of Human EI. The screening assays are performed in the presence (and absence) of the putative functionally active peptide and the affect of the peptide on these activities is determined. For example, Human EI can be used as a positive control to establish a 100% complex forming and/or elastinolytic inhibitory activity. In this manner, the screening assays can be used to identify peptides of Human EI (or functionally equivalent peptide analogs) which are capable of inhibiting the formation of a complex between Human EI and elastase and/or inhibiting the elastinolytic activity of elastase. A peptide or protein (which is known not to form a complex with or inhibit the activity of elastase) can be used as a negative control in the screening assays. Thus, it will be understood by those skilled in the art that the products of the invention include functionally equivalent peptides of Human EI (as well as functionally equivalent peptide analogs thereof) that form a covalent complex with elastase (and oligonucleotides encoding such peptides) and/or inhibit the elastinolytic activity of elastase.

Thus, according to one aspect of the invention, an isolated peptide that is capable of inhibiting the elastinolytic activity of elastase and/or inhibiting complex formation between Human EI and elastase is provided. The isolated peptide specifically binds to elastase, thereby preventing interaction between elastase and the Human EI. The isolated peptides of the invention are related to, or derived from, the active site of Human EI which includes the amino acids which participate in HEI complex formation with elastase, e.g., the reactive center loop comprising amino acids 331–351 (inclusive) of Sequence I.D. Number 12.

The flanking regions (also referred to as the "hinge" regions) of the reactive center loop each contain approximately 10 amino acid residues. Interestingly, the reactive center loop is the most variable region in serpins, however, the flanking regions are conserved. The region between the reactive center loop and the C-terminus (amino acids 352–379) is well-conserved in Ov-serpins and its size in Ov-serpins is the minimal for serpin superfamily members.

As used herein in reference to a peptide, the term "isolated" refers to the cloned expression product of an isolated oligonucleotide (defined below); a peptide which is isolated following cleavage from a larger polypeptide (Human EI) or a peptide that is synthesized, e.g., using solution and/or solid phase peptide synthesis methods as disclosed in, for example, U.S. Pat. No. 5,120,830, the entire contents of which are incorporated herein by reference. Accordingly, the phrase "isolated peptides" embraces peptides derived (by chemical or enzymatic cleavage) from Human EI, as well as functionally equivalent peptide analogs (defined below) of the foregoing peptides, which form a complex with elastase and/or inhibit the elastinolytic activity of elastase.

As used herein, the term "isolated" in reference to an oligonucleotide, means an RNA or DNA polymer, portion of genomic nucleic acid, cDNA or synthetic nucleic acid which, by virtue of its origin or manipulation: (a) is not associated with all of a nucleic acid with which it is associated in nature (e.g., is present in a host cell as a portion of an expression vector); or (b) is linked to a nucleic acid or other chemical moiety other than that to which it is linked in nature; or (c) does not occur in nature. By "isolated" it is further meant a nucleic acid sequence: (i) amplified in vitro by, for example, the polymerase chain reaction (PCR); (ii) synthesized by, for example, chemical synthesis; (iii) recombinantly produced by cloning; or (iv) purified from a more complex molecule or from a mixture of molecules, such as by cleavage and size fractionation.

As used herein, the term "polypeptide analog" refers to a peptide/protein which shares a common structural feature with the molecule to which it is deemed to be an analog. A "functionally equivalent" polypeptide analog is a peptide/protein analog which further shares a common functional activity with the molecule to which it is deemed an analog. Thus, as used herein, the term "functionally equivalent polypeptide analog" refers to a peptide analog that is capable of inhibiting complex formation between Human EI and elastase and/or inhibiting the elastinolytic activity of elastase in vitro by, for example, competing with Human EI for binding to elastase. Functionally equivalent polypeptide analogs of Human EI are identified using the above-described complex forming and/or elastinolytic activity assays. Such assays are predictive of the ability of a molecule to inhibit these activities in vivo. Accordingly, a "functionally equivalent polypeptide analog" of Human EI includes the polypeptides included in the active site (i.e., that region of Human EI which participates in complex formation with elastase and/or which has elastinolytic inhibitory activity) of Human EI which contain conservative amino acid substitutions), provided that the peptide analogs are capable of inhibiting complex formation between Human EI and elastase and/or inhibiting the elastinolytic activity of elastase in vivo and/or in vitro. The active site of Human EI includes the active center loop (described above). Such peptides may be synthesized and/or selected from libraries containing peptides or peptide analogs according to standard library screening procedures. Alternatively, the sequence and relative positions of the amino acids of the active site of Human EI, including, e.g., the amino acids involved in elastase binding, may be used in computer-based modeling systems to predict the secondary and tertiary structure of the surface domain. Such computer-based systems are well-known to those of ordinary skill in the art of rational drug design. Based upon the tertiary structure of an enzyme inhibitor, it is possible to identify the binding region of the inhibitor that is involved in complex formation with its corresponding enzyme. In this manner, peptides and/or other compounds which include or mimic the structure and/or which are capable of binding to elastase can be rationally designed. Thus, new compounds may be designed which mimic the activity of Human EI or which act as a competitive inhibitor of Human EI binding to elastase.

The polypeptide analogs can include "conservative amino acid substitutions." As used herein, "conservative amino acids substitution" refers to an amino acid substitution which does not alter the relative charge or size characteristics of the peptide in which the amino acids substitution is made. Conservative substitutions of amino acids include substitutions made amongst amino acids within the following groups: (a) MILV; (b) FYW; (c) KRH; (d) AG; (e) ST; (f) QN; (g) ED.

The functionally equivalent polypeptides include "unique fragments" which are related to, or derived from, the active site of Human EI. A "unique fragment" of a protein or nucleic acid sequence is a fragment which is not currently known to occur elsewhere in nature (except in allelic or allelomorphic variants). Unique fragments act as a signature of the gene or protein from which they are derived. A unique fragment will generally exceed 15 nucleotides or 5 amino acids in length. One of ordinary skill in the art can readily identify unique fragments by searching available computer data-bases of nucleic acid and protein sequences such as Genbank, (Los Alamos National Laboratories, USA), EMBL, or SWISS-PROT. A unique fragment is particularly useful, for example, in generating monoclonal antibodies or in screening genomic DNA or cDNA libraries. Preferably, the peptides containing unique fragments include between about 3 and about 100 amino acids. More preferably, the peptides contain about 10 and about 25 amino acids.

It will be appreciated by those skilled in the art that various modifications of the foregoing functionally equivalent peptides and peptide analogs can be made without departing from the essential nature of the invention. Accordingly, it is intended that polypeptides which include conservative substitutions and coupled proteins in which a peptide of the invention is coupled to a solid support (such as polymeric bead), a carrier molecule (such as keyhole limpet hemocyanin), a toxin (such as resin) or a reporter group (such as a radiolabel or other tag), also are embraced within the teachings of the invention.

Because the primary physiological locations of HEI are tissue sites that have been infiltrated with neutrophils, monocytes and macrophages, it is believed that local application of recombinant HEI (or its functionally equivalent peptides) to the inflammatory site can be useful for treating inflammatory conditions that are mediated by the influx of these cells. Thus, according to another aspect of the invention, methods and compositions for modulating an inflammatory response in a subject are provided. The methods involve administering a pharmaceutical composition containing an agent that inhibits the elastinolytic activity of elastase or alternatively, an agent that upregulates HEI production in situ. For example, the agent may be an isolated Human EI, the above-described isolated peptides and/or the above-described isolated functionally equivalent peptide analogs. The pharmaceutical composition contains a therapeutically effective amount of agent for treating the condition (i.e., slowing the progression of, reducing or preventing the inflammatory response). In a particularly preferred embodiment, the pharmaceutical composition (which contains a polypeptide that inhibits the elastinolytic activity of a human elastase) is useful for treating an inflammatory response that is mediated by a serine protease (e.g., elastase, proteinase-III, cathepsin G).

In general, the therapeutically effective amount is between about 1 $\mu$g and about 100 mg/kg. The preferred amount can be determined by one of ordinary skill in the art in accordance with standard practice for determining optimum dosage levels of the agent. The Human EI, isolated functionally equivalent Human EI polypeptides, and/or functionally equivalent polypeptide analogs are formulated into a pharmaceutical composition by combination with an appropriate pharmaceutically acceptable carrier. For example, the polypeptides may be used in the form of their pharmaceutically acceptable salts, or may be used alone or in appropriate association, as well as in combination with other pharmaceutically active compounds. The polypeptides may be formulated into preparations in solid, semisolid, liquid or gaseous form such as liposomes, tablets, capsules, powders, granules, ointments, solutions, suppositories, inhalants, aerosols and injections, in usual ways for oral, parenteral, or surgical administration. Exemplary pharmaceutically acceptable carriers are described in U.S. Pat. No. 5,211,657, the entire contents of which patent are incorporated herein by reference. The invention also includes locally administering the composition as an implant.

Generally, they may be used for treatment of conditions involving destructive action by elastase and by other proteinases with which they react, including tissue destruction as a consequence of inflammation. Specific applications include bronchiectasis as a consequence of inflammation in the lung, intestinal tissue damage in chronic granulatomous disease and LAD (leukocyte adhesion deficiency), cystic fibrosis, pancreatitis, malignancies, blood damage vessel due to clotting, blistering skin disorders, reperfusion injury, and ulcerative colitis. Other applications include all conditions where the level of Human EI is abnormal, elastase or other proteinases reactive with Human EI or variants of human EI are in excess, or when there is excess phagocyte accumulation.

Antibodies to the Human EI can be used to detect the presence, absence or amount of Human EI. Such antibodies are useful in evaluating congenital or acquired deficiencies and also in evaluating disease states. For example, antibodies to Human EI may be used to evaluate the level of phagocytic cell response in infectious disease states such as tuberculosis and leprosy. Likewise, such antibodies may be used to diagnose inflammatory states such as rheumatological diseases (e. g., rheumatoid arthritis), immunological diseases (e.g., pemphigus), idiopathic diseases (e.g., sarcoidosis) and inflammatory diseases (e.g., adult respiratory distress syndrome.) Antibodies further may be used as a diagnostic tool in connection with neoplastic diseases (e.g., monitoring of malignancies by evaluation of host response, evaluating the metastatic capacity of malignant cells), in genetic diseases (e.g., cystic fibrosis or hereditary abnormalities in the elastase-elastase inhibitor system), in abnormal maturation of myelomonocytic cells (e.g., Chediak-Higashi syndrome), in pancreatitis and other disorders of the pancreas, and generally for evaluation of the genetic variability of the human EI-proteinase system in the population and its relationship to diseases.

Antibodies to Human EI also have therapeutic uses, including treatment of conditions in which elastase functions abnormally, elastase inhibitor is in excess over elastase, or phagocyte recruitment is defective. Such conditions include abnormality and susceptibility to infections or inadequate immune defense. Human EI or functionally equivalent peptides and peptide analogs can be administered with agents that decrease the rate of oxidation inactivation (e.g., glutathione and N-acetyl cysteine). Such agents could be mixed with human EI or EI variant or can be chemically incorporated in the form of a modified human EI molecule.

In order to target HEI or its functionally equivalent variants to particular physiological sites, altered sequences can be introduced at one or more sites in the overall sequence, for example by PCR based methodology. Alternatively, targeting moieties can be chemically incorporated into human EI or EI variants. Moreover, targeting of HEI or its functionally equivalent variants can be achieved by attaching the recombinant compound to antibodies or portions of antibodies, which are directed to an antigen located at a particular physiological site. Alternatively, the HEI can be incorporated into liposomes to which such targetting agents are attached to deliver HEI to a particular location. Additionally, such HEI functionally equivalent variants can be attached to insoluble substrates for facilitating the separation of elastase or other Serpin molecules from a solution by performing a chromatographic separation based on specific affinity of the insoluble recombinant EI variant for the Serpin molecule. Such affinity methods are useful for research applications, large scale production and isolation of the soluble molecule and are potentially useful for therapeutic applications (e.g. plasmaphoresis).

Likewise, oligonucleotides complementary to ribonucleotides encoding Human EI or a portion thereof can be useful for some of the above-noted diagnostic purposes. Further, the oligonucleotides encoding Human EI or a functionally equivalent variant thereof, alone or as part of a suitable expression vector or delivery system can be useful in gene replacement therapy relating to the conditions described above. Preparations containing effective amounts of such oligonucleotides, suitable expression vectors or delivery systems are made using conventional cloning and isolation techniques as described above or by other methods such as PCR (polymerase chain reaction). These and many other uses will be apparent to one of ordinary skill in the art.

Each of the above-cited patents, patent publications and references is incorporated in its entirety herein by reference. The foregoing description is intended to be taken in an illustrative, and not a limiting, sense.

A sequence listing is presented below and is followed by what is claimed:

I claim:

1. An antibody that selectively binds to the human monocyte elastase inhibitor encoded by Sequence I.D. No. 12 or an allelic variant of Sequence I.D. No. 12.

2. The antibody of claim 1, wherein the antibody is a monoclonal antibody.

3. An antibody that selectively binds to an isolated peptide encoded by Sequence ID No. 12 or an allelic variant of Sequence I.D. No. 12, wherein said peptide includes a single conservative amino acid substitution for cysteine at codon 344.

4. The antibody of claim 3, wherein the amino acid substitution is selected from the group consisting of valine, alanine, and arginine.

5. An antibody that selectively binds to an isolated peptide encoded by Sequence ID No. 12 or an allelic variant of Sequence I.D. No. 12, wherein said peptide includes a single conservative amino acid substitution in an amino acid between codon positions 331–351, inclusive.

6. The antibody of claim 4, wherein the conservative amino acid substitution consists of the replacement of the cysteine at codon position 344 by an amino acid selected from the group consisting of a valine, a serine, a leucine and a methionine.

7. An antibody that selectively binds to an isolated peptide encoded by Sequence ID No. 12 or an allelic variant of Sequence I.D. No. 12, wherein said peptide includes two conservative amino acid substitutions in amino acids between codon positions 331–351, inclusive.

8. The antibody of claim 7, wherein the second amino acid substitution is at a codon selected from the group of codon positions 346, 345, 343, 342, 337, 347, 348, and 349.

9. A method for detecting the presence, absence or amount of a human monocyte elastase inhibitor, comprising
  (1) contacting a diagnostically effective amount of an antibody of claim 1 with a sample suspected of containing a human monocyte elastase inhibitor under conditions that allow the antibody to selectively bind to the human monocyte inhibitor; and
  (2) detecting the amount of bound antibody.

10. The method of claim 9, wherein the antibody is used in an ELISA assay.

* * * * *